US011678944B1

(12) United States Patent
Azevedo et al.

(10) Patent No.: US 11,678,944 B1
(45) Date of Patent: Jun. 20, 2023

(54) MANIPULATORS AND CARTRIDGES FOR ROBOTIC-ASSISTED VASCULAR ACCESS

(71) Applicant: Hyperion Surgical, Inc., Miramar, FL (US)

(72) Inventors: Jonathan Azevedo, Fort Lauderdale, FL (US); Roman Devengenzo, San Jose, CA (US)

(73) Assignee: Hyperion Surgical, Inc., Miramar, FL (US)

( * ) Notice: Subject to any disclaimer, the term of this patent is extended or adjusted under 35 U.S.C. 154(b) by 0 days.

(21) Appl. No.: 17/893,534

(22) Filed: Aug. 23, 2022

(51) Int. Cl.
  *A61B 34/30* (2016.01)
  *A61M 25/09* (2006.01)
  *A61B 34/20* (2016.01)

(52) U.S. Cl.
  CPC ............. *A61B 34/30* (2016.02); *A61M 25/09* (2013.01); *A61B 2034/2051* (2016.02); *A61B 2034/301* (2016.02); *A61B 2034/303* (2016.02)

(58) Field of Classification Search
  CPC ............ A61B 34/30; A61B 2034/2051; A61B 2034/301; A61B 2034/303; A61M 25/09
  See application file for complete search history.

(56) References Cited

U.S. PATENT DOCUMENTS

| 5,246,426 A | 9/1993 | Lewis et al. |
| 6,068,599 A | 5/2000 | Saito et al. |
| 6,375,471 B1 | 4/2002 | Wendlandt et al. |
| 6,419,633 B1 | 7/2002 | Robinson et al. |
| 6,709,394 B2 | 3/2004 | Frisa et al. |
| 7,494,494 B2 | 2/2009 | Stoianovici et al. |
| 8,308,741 B2 | 11/2012 | Hyde et al. |
| 8,348,861 B2 | 1/2013 | Glozman et al. |
| 8,715,233 B2 | 5/2014 | Brewer et al. |

(Continued)

FOREIGN PATENT DOCUMENTS

| CN | 104398306 A | 3/2015 |
| WO | WO-2015179505 A1 | 11/2015 |

(Continued)

OTHER PUBLICATIONS

Chen, A. et al., "Portable robot for autonomous venipuncture using 3D near infrared image guidance," Technology (Singap World Sci), 1(1):72-87 (2013); doi:10.1142/S2339547813500064.

(Continued)

*Primary Examiner* — Richard G Louis
(74) *Attorney, Agent, or Firm* — Cooley LLP

(57) ABSTRACT

Manipulators and cartridges for robotic-assisted vascular access are described herein. In some embodiments, an apparatus includes a cartridge including a guidewire, a needle, and a catheter that are coaxially disposed with respect to each other; and a plurality of guides coupled to the guidewire, the needle, and the catheter; a manipulation device including a plurality of actuators each configured to couple to a different guide member of the plurality of guides, the plurality of actuators being configured to linearly advance and retract the plurality of guides to move the needle, the guidewire, and the catheter; and a control unit operatively coupled to the manipulation device, the control unit configured to control the plurality of actuators to selectively move the needle, the guidewire, and the catheter to gain access via the catheter to a target vessel of a patient.

15 Claims, 47 Drawing Sheets

(56) References Cited

U.S. PATENT DOCUMENTS

| | | | |
|---|---|---|---|
| 8,758,256 | B2 | 6/2014 | O'Laughlin et al. |
| 8,945,011 | B2 | 2/2015 | Sheldon et al. |
| 8,951,195 | B2 | 2/2015 | Sheldon et al. |
| 9,033,880 | B2 | 5/2015 | Sheldon et al. |
| 9,364,171 | B2 | 6/2016 | Harris et al. |
| 9,743,875 | B2 | 8/2017 | Maguire et al. |
| 9,861,739 | B2 | 1/2018 | Sheldon et al. |
| 10,232,146 | B2 | 3/2019 | Braithwaite et al. |
| 10,384,039 | B2 | 8/2019 | Ribelin et al. |
| 10,493,262 | B2 | 12/2019 | Tran et al. |
| 10,687,784 | B2 | 6/2020 | Shoham |
| 2003/0060716 | A1 | 3/2003 | Heidrich |
| 2006/0095022 | A1 | 5/2006 | Moll et al. |
| 2006/0293643 | A1 | 12/2006 | Wallace et al. |
| 2007/0055152 | A1 | 3/2007 | Ukubo et al. |
| 2008/0146915 | A1 | 6/2008 | McMorrow |
| 2008/0275396 | A1 | 11/2008 | Neerken et al. |
| 2009/0005687 | A1 | 1/2009 | Kawae |
| 2009/0275823 | A1 | 11/2009 | Ayati et al. |
| 2010/0010505 | A1 | 1/2010 | Herlihy et al. |
| 2012/0259220 | A1* | 10/2012 | Sheldon .............. A61B 8/14 600/439 |
| 2013/0172713 | A1 | 7/2013 | Kirschenman |
| 2015/0065916 | A1 | 3/2015 | Maguire et al. |
| 2017/0080166 | A1 | 3/2017 | Bagwell et al. |
| 2018/0256267 | A1 | 9/2018 | Cohen et al. |
| 2018/0311473 | A1 | 11/2018 | Laby et al. |
| 2019/0000568 | A1 | 1/2019 | Connolly et al. |
| 2019/0290372 | A1 | 9/2019 | Arnold et al. |
| 2020/0170724 | A1 | 6/2020 | Flatt et al. |
| 2020/0188041 | A1 | 6/2020 | Toporek et al. |
| 2020/0253670 | A1 | 8/2020 | Doisneau et al. |

FOREIGN PATENT DOCUMENTS

| | | |
|---|---|---|
| WO | WO-2019213647 A1 | 11/2019 |
| WO | WO-2020076942 A2 | 4/2020 |
| WO | WO-2020142338 A1 | 7/2020 |
| WO | WO-2020142340 A1 | 7/2020 |

OTHER PUBLICATIONS

International Search Report and Written Opinion for International Application No. PCT/US2022/041392, dated Dec. 6, 2022, 16 pages.

Leipheimer, J. M. et al., "First-in-human evaluation of a hand-held automated venipuncture device for rapid venous blood draws," Technology (Singap World Sci), 7(3-4):98-107 (2019); doi:10.1142/S2339547819500067.

Non Final Rejection for U.S. Appl. No. 17/700,391, dated Sep. 23, 2022, 16 pages.

Final Office Action dated Jan. 27, 2023 for U.S. Appl. No. 17/700,391, 15 pages.

* cited by examiner

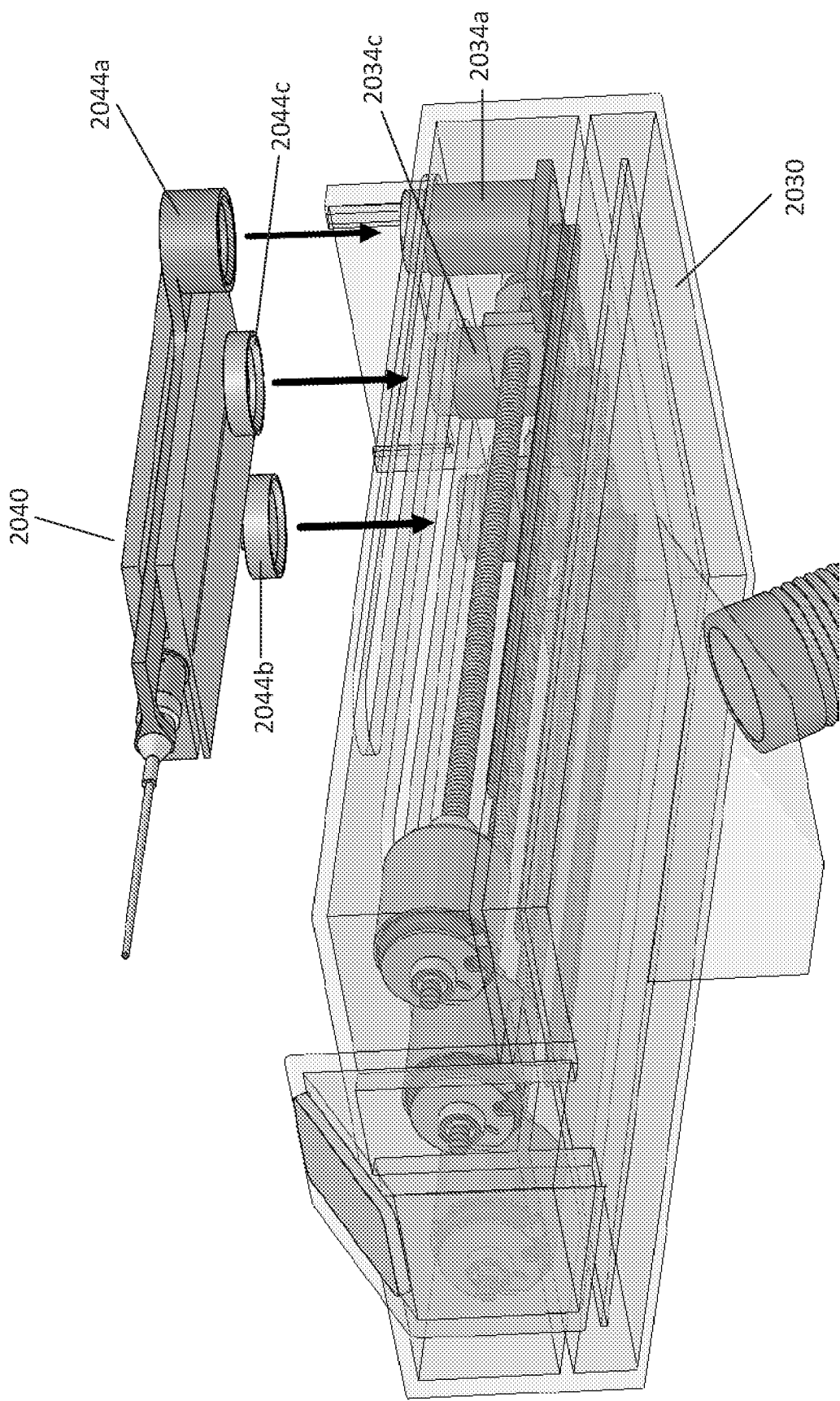

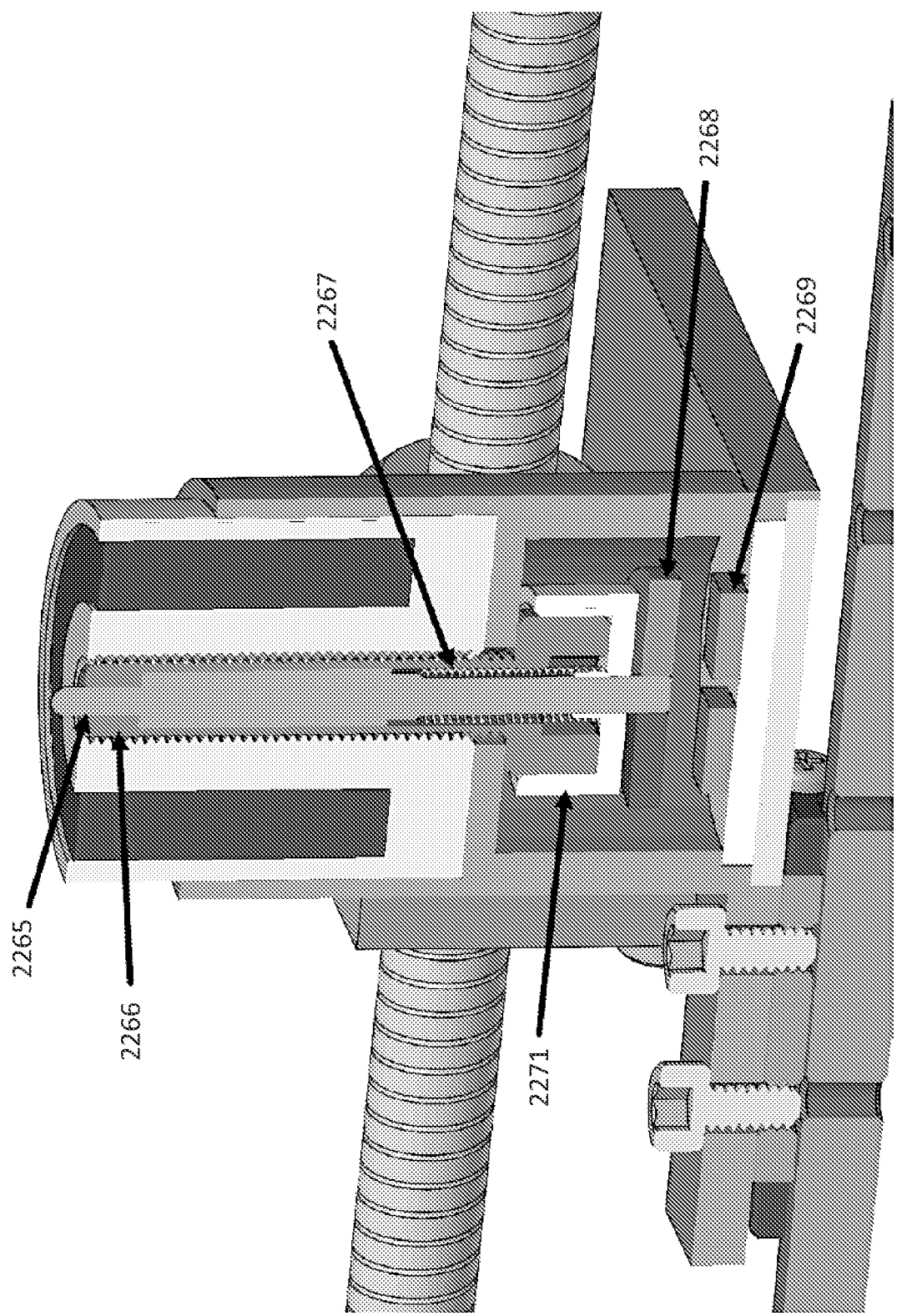

| Seldinger Step | Description | Wire Guide | Needle Guide | Catheter Guide | Wire Puck | Needle Puck | Catheter Puck |
|---|---|---|---|---|---|---|---|
| 1 | Align needle end with catheter tip | Dynamic | Dynamic | Static | Unpowered | Unpowered | Unpowered |
| 2 | Insert needle tip into artery | Dynamic | Dynamic | Dynamic | Unpowered | Unpowered | Unpowered |
| 3 | Advance wire into artery | Dynamic | Static | Static | Unpowered | Unpowered | Unpowered |
| 4 | Advance catheter into artery | Static | Static | Dynamic | Unpowered | Unpowered | Unpowered |
| 5 | Retract needle and wire | Dynamic | Dynamic | Static | Unpowered | Unpowered | Unpowered |
| 6 | Release Catheter Guide | Static | Static | Static | Unpowered | Unpowered | Powered |
| 7 | Move the robot to get catheter access | Static | Static | Static | Unpowered | Unpowered | Unpowered |
| 8 | Remove the guide from the catheter | Static | Static | Static | Unpowered | Unpowered | Unpowered |
| 9 | Remove the cartridge from the robot | Static | Static | Static | Powered | Powered | Unpowered |

FIG. 25

MANIPULATORS AND CARTRIDGES FOR ROBOTIC-ASSISTED VASCULAR ACCESS

CROSS-REFERENCE TO RELATED APPLICATIONS

This application is a division of U.S. patent application Ser. No. 17/700,391, filed Mar. 21, 2022, which claims priority to U.S. Provisional Patent Application No. 63/236,537, filed Aug. 24, 2021.

TECHNICAL FIELD

The present disclosure relates generally to robotic systems, devices, and methods for vascular access. More specifically, the present disclosure relates to robotic systems, devices, and methods for positioning a needle and/or catheter into a blood vessel of a subject.

BACKGROUND

Interventional medical procedure is a popular procedure that can diagnose and treat diseases in various organs of a patient. Interventional medical procedures are minimally-invasive image guided medical procedures that minimize risk to the patient in comparison to open surgeries.

In order to perform an interventional medical procedure on the vascular system, an operator may need to gain safe access to one or more blood vessels. Traditionally, sharp trocars were used access blood vessels. Trocars can be used to create lumens through which a catheter can be eventually inserted. However, there are several drawbacks associated with trocars. For instance, improperly placed trocars can lead to various complications such as organ injury, hemorrhage, failed access, catheter malposition, infection, etc.

More recently, the Seldinger technique has been widely employed in order to gain safe access to the vascular system. The Seldinger technique involves puncturing a desired blood vessel with a needle. A guidewire is inserted through the needle such that the guidewire is placed into the blood vessel. Once the guidewire has advanced to the desired length and/or location in the blood vessel, the needle is removed. A catheter is then advanced into the blood vessel over the guidewire. Once the catheter is in the blood vessel, the guidewire is pulled out. The Seldinger technique has fewer complications in comparison to using trocars.

However, the Seldinger technique often requires an experienced surgeon and/or operator to perform the technique on a patient. For instance, human errors made by a surgeon and/or an operator while inserting the guidewire through the needle, or advancing the guidewire to the desired location in the blood vessel can cause complications such as vessel perforation, pseudo aneurysm formation, hemorrhage, infection, etc. Therefore, human errors and inconsistencies while performing the Seldinger technique can cause failures and lead to complications.

Accordingly, there is an unmet need to provide guidance to operators while inserting a needle and/or catheter into a patient to gain safe vascular access and to improve consistency and reduce complications that may arise due to human errors.

SUMMARY

Robotic system, devices, and methods for vascular access are described herein. In some embodiments, an apparatus comprises a cart, a manipulation device, and a robotic arm. The cart can be movable from a first location to a second location near a patient. The cart can have a platform configured to support an arm of the patient. The manipulation device can be configured to releasably couple a cartridge including a needle, a catheter, and a guidewire that are coaxially disposed with respect to each other. The manipulation device can include a plurality of actuation mechanism configured to selectively advance the needle, the catheter, and the guidewire when the manipulation device is coupled to the cartridge. The robotic arm can have a first end mounted on the cart and a second end coupled to the manipulation deice. The robotic arm can include a plurality of joints that are configured to rotate about a plurality of axes to position the cartridge relative to the arm of the patient such that the needle, the catheter, and the guidewire can be inserted into a target blood vessel of the patient.

In some embodiments, an apparatus comprises a cartridge including a guidewire, a needle, and a catheter. The guidewire can be configured to couple to a first linear actuator moveable along a first axis to advance the guidewire. The needle can be configured to couple to a second linear actuator moveable along a second axis to advance the needle. The catheter can be configured to couple to a third linear actuator moveable along a third axis to advance the catheter. The guidewire, the needle, and the catheter can be arranged coaxially with the guidewire disposed within a lumen of the needle and the needle being disposed within a lumen of the catheter.

In some embodiments, a method comprises advancing a tip of a needle into a target vessel using a first linear actuator of a manipulating device. The method also includes advancing a tip of a guidewire using a second linear actuator of the manipulation device such that the tip of the guidewire extends distally from the tip of the needle. After advancing the tip of the guidewire, the method comprises advancing a tip of a catheter using a third linear actuator of the manipulation device such that the tip of the catheter extends distally from the tip of the needle. The catheter can include a catheter hub that is releasably coupled to the manipulation device. After advancing the tip of the catheter the method comprises releasing the catheter from the manipulating device.

In some embodiments, an apparatus comprising a cart movable from a first location to a second location near a patient, a manipulation device configured to releasably couple to a cartridge including a needle, a catheter, and a guidewire that are coaxially disposed with respect to each other, and a robotic arm having a first end mounted to the platform and a second end coupled to the manipulation device. The cart can have a platform and a vertical adjustment element configured to adjust a distance between the platform and a ground supporting the cart. The manipulation device can include a plurality of actuators each configured to couple to a different one of the needle, the catheter, and the guidewire to selectively advance the needle, the catheter, and the guidewire, when the manipulation device is coupled to the cartridge. The robotic arm can have a plurality of segments joined together via a plurality of joints such that the robotic arm can be moved to position the needle, the catheter, and the guidewire for insertion into a target vessel.

In some embodiments, the apparatus can further comprise an imaging system coupled to a distal end portion of the manipulation device. The imaging system can be configured to capture a traverse view and a longitudinal view each including the target vessel. In some embodiments, the imaging system can be configured to change the traverse view as a tip of the needle is advanced into the target vessel to show the transverse view that corresponds to a transverse plane of the tip of the needle. In some embodiments, the imaging system can include an ultrasound array.

In some embodiments, the manipulation device can include a coupling mechanism coupled to one of the plurality of actuators. The coupling mechanism can be configured to releasably couple to a coupling element in the cartridge that is coupled to at least one of the needle, the catheter, or the guidewire, such that, upon the coupling mechanism being coupled to the coupling element, movement of the actuator causes a respective movement of the at least one of the needle, the catheter, and the guidewire. In some embodiments, the coupling mechanism can include at least one magnet, and the coupling element can include at least one magnetic element. The at least one magnet can be configured to magnetically couple to the at least one magnetic element. In some embodiments, the manipulation device can include at least one sensor to detect the coupling between the coupling mechanism of the manipulation device and the coupling element in the cartridge. In some embodiments, the at least one sensor can include a Hall Effect sensor, and the manipulation device can further include a permanent magnet that is configured to displace in response to the coupling between the coupling mechanism and the coupling element. The Hall Effect sensor can be configured to measure a change in a magnetic field intensity caused by the movement of the permanent magnet.

In some embodiments, the manipulation device can be pivotably supported by a joint of the plurality of joints with respect to a distal most segment of the robotic arm such that an angle of insertion of the needle, the catheter, and the guidewire into the target vessel can be adjusted via the joint. In some embodiments, a center of mass of the manipulation element can be disposed near the joint to reduce torque due to gravity on the joint. In some embodiments, each joint of the plurality of j joints of the robotic arm can include a failsafe brake configured to lock movement about the joint until electrically released.

In some embodiments, the apparatus can further comprise an imaging system configured to capture a view including at least a part of the manipulating device and a portion of the patient including the target vessel, and a communication interface configured to send image data of the view to a remote compute device such that a position of the cartridge relative to the portion of the patient can be confirmed by a user at the remote compute device.

In some embodiments, an apparatus can comprise a cartridge including a guidewire, a needle, and a catheter that are coaxially disposed with respect to each other, and a plurality of guides coupled to the guidewire, the needle, and the catheter. The apparatus can also comprise a manipulation device including a plurality of actuators each configured to couple to a different guide member of the plurality of guides. The plurality of actuators can be configured to linearly advance and retract the plurality of guides to move the needle, the guidewire, and the catheter. The apparatus can also comprise a control unit operatively coupled to the manipulation device. The control unit can be configured to control the plurality of actuators to selectively move the needle, the guidewire, and the catheter to gain access via the catheter to a target vessel of a patient.

In some embodiments, the plurality of actuators can include: a first linear actuator configured to linearly advance and retract a first guide of the plurality of guides to move the guidewire, a second linear actuator configured to linearly advance and retract a second guide of the plurality of guides to move the needle, and a third linear actuator configured to linearly advance and retract a third guide of the plurality of guides to move the catheter. In some embodiments, the manipulation device further can include a plurality of shafts supporting the first linear actuator, the second linear actuator, and the third linear actuator. In some embodiments, the plurality of shafts can include a first shaft supporting the first linear actuator and the second linear actuator, and a second shaft supporting the third linear actuator. In some embodiments, the plurality of shafts can include a first shaft supporting the first linear actuator, a second shaft supporting the second linear actuator, and a third shaft supporting the third linear actuator.

In some embodiments, the manipulation device can include a plurality of recessed portions. Each recessed portion of the plurality of recessed portions can be configured to receive a respective guide member of the plurality of guides. In some embodiments, each actuator of the plurality of actuators can include a magnet configured to magnetically couple that actuator with a respective one of the plurality of guides. In some embodiments, each guide of the plurality of guides can include a magnetic portion configured to magnetically couple to the magnet of the respective actuator coupled to that guide. In some embodiments, each actuator of the plurality of actuators can include a sensor configured to detect a coupling between the magnet of that actuator with the respective coupling element. In some embodiments, the cartridge can be configured to store the guidewire in a linear state.

In some embodiments, an apparatus can comprise a cartridge configured to couple to a manipulation device of a robotic system for providing access to a target vessel of a patient. The cartridge can include: a housing, a guidewire disposable at least partially within the housing and configured to couple to a first linear actuator of the manipulation device that is moveable along a first axis to advance the guidewire, a needle disposable at least partially within the housing and configured to couple to a second linear actuator of the manipulation device that is moveable along a second axis to advance the needle, and a catheter configured to couple to a third linear actuator of the manipulation device that is moveable along a third axis to advance the catheter. The guidewire, the needle, and the catheter can be arranged coaxially with the guidewire being disposed within a lumen of the needle and the needle can be disposed within a lumen of the catheter.

In some embodiments, the cartridge can further comprise a first guide coupled to the guidewire and configured to couple to the first linear actuator, a second guide coupled to the needle and configured to couple to the second linear actuator, and a third guide releasably coupled to the catheter and configured to couple to the third linear actuator. In some embodiments, the first guide can include a first coupling element configured to couple the first guide to the first linear actuator, the second guide can include a second coupling element configured to couple the second guide to the second linear actuator, and the third guide can include a third coupling element configured to couple the third guide to the third linear actuator.

In some embodiments, the first, second, and third coupling elements can include magnetic portions that are configured to engage with a magnet of respective ones of the first, second, and third linear actuators. In some embodiments, the housing can include features configured to fit in slots in the manipulation device to mechanically couple the housing to the manipulation device.

In some embodiments, a method can comprise advancing, using a first linear actuator of a robotic system, a tip of a needle into a target vessel. The needle can be coaxially disposed with a catheter and a guidewire. The method can also comprise advancing, using a second linear actuator of a robotic system, a tip of the guidewire through a lumen of the needle such that the tip of the guidewire extends distally from the tip of the needle. After advancing the tip of the guidewire, the method can comprise advancing, using a third linear actuator of the robotic system, a tip of the catheter over at least a portion of the guidewire such that the tip of the catheter extends into the target vessel. The catheter can include a catheter hub that is releasably coupled to the third linear actuator via a guide. After advancing the tip of the catheter, the method can also comprise retracting, using the first and second linear actuators, the needle and the guidewire from the target vessel.

In some embodiments, the method can further comprise decoupling, after advancing the tip of the catheter hub from the guide so that the catheter is decoupled from the robotic system. In some embodiments, the first, second, and third linear actuators are disposed in a manipulation device mounted to a robotic arm of the robotic system. The method can further comprise rotating at least one joint of the robotic arm to position the manipulation device at a predetermined acute angle relative to a longitudinal axis of a target vessel.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 20A and 20B illustrate attaching and/or coupling a cartridge assembly to a manipulation device, in accordance with some embodiments.

FIGS. 22A and 22B illustrate a mechanism to detect a coupling between a permanent electromagnet in a manipulation device and a puck in a cartridge assembly, in accordance with some embodiments.

FIG. 25 is a table illustrating the states of the needle actuator, catheter actuator, and guidewire actuator for the Seldinger technique, in accordance with some embodiments.

DETAILED DESCRIPTION

Robotic systems, devices, and methods for vascular access are described herein. In some embodiments, the robotic systems, devices, and methods described herein automate or semi-automate vascular access (e.g., the procedure of the Seldinger technique) in order to provide safe access to blood vessel(s) and/or organ(s). The blood vessel(s) can be any suitable type of blood vessel(s) such as arteries (e.g., radial artery, femoral artery, etc.), veins (e.g., brachial vein, basilic vein, cephalic vein, femoral vein, internal jugular vein, median cubital vein, median antebrachial vein, etc.).

In some embodiments, the technology described herein includes a robotic system for facilitating vascular access. The robotic system can include a manipulation device. The manipulation device can comprise or otherwise be attached to a guidewire, a needle, and a catheter that is to be positioned in a blood vessel of a subject. The robotic system and the manipulation device can be controlled by a user (e.g., an operator, a surgeon, etc.) using one or more input/output (I/O) devices. In some embodiments, the manipulation device can include an imaging device (e.g., an ultrasound array). The imaging device can provide the user with visual aid (e.g., ultrasound images of the blood vessel) of the procedure such as the guidewire, the needle, and/or the catheter being inserted into a blood vessel. In some embodiments, the I/O device(s) can include a sensor (e.g., camera) that provides feedback (e.g., image data of the robotic system, manipulation device, and/or portion of a subject's body) to the robotic system as the manipulation device accesses a blood vessel. The robotic system can adjust the movement, position, and/or orientation of the guidewire, needle, and/or catheter based on data from the sensor so as to automate the procedure of vascular access. In some embodiments, the user can remotely control the robotic system and/or the manipulation device to perform the procedure based on the data from the sensor and the visual aid from the imaging device. Further details of such a system are described below with reference to the figures.

Vascular Access System and Components

Figure 1:
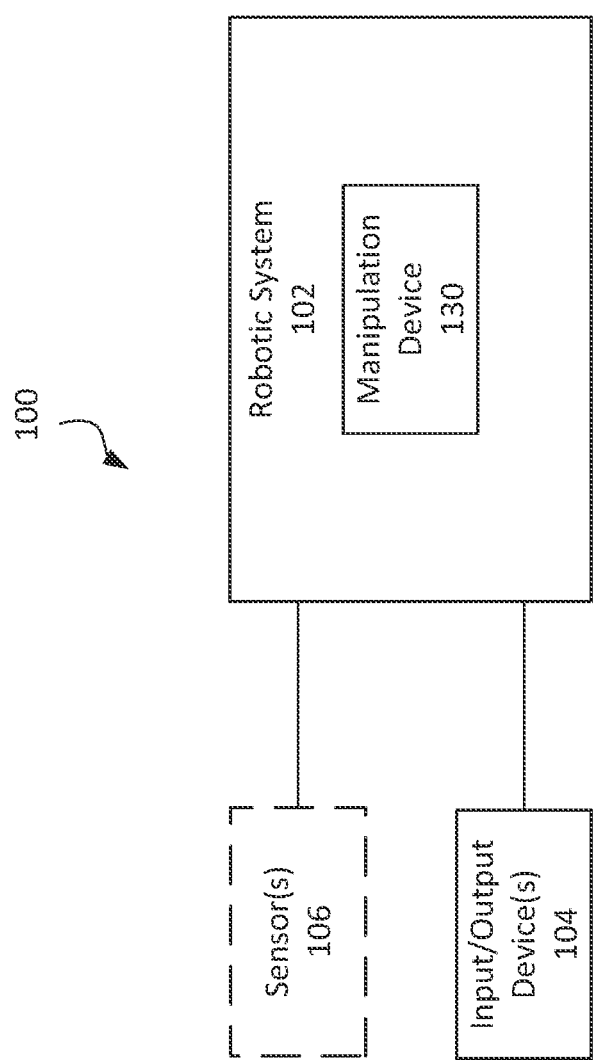
FIG. 1 is a block diagram that illustrates a system for facilitating vascular access, according to some embodiments.

FIG. 1 is a high-level block diagram that illustrates a system 100, according to some embodiments. System 100 can be configured to automate and/or semi-automate a medical procedure for vascular access. System 100 includes a robotic system 102 including a manipulation device 130. The robotic system 102 and/or the manipulation device 130 can be communicably coupled to one or more I/O device(s) 104 (e.g., external and/or remote I/O devices). In some embodiments, the robotic system 102 and/or the manipulation device 130 can be optionally communicably coupled to one or more sensor(s) 106 (e.g., external and/or remote sensors).

In some embodiments, the robotic system 102 can be any suitable robot. For instance, the robotic system 102 can include a robotic arm that can form a part of a robotic device. The robotic device itself can be an autonomous and/or a semi-autonomous cart coupled to and/or integrated with the manipulation device. In some embodiments, the robotic device can include a base with a flat portion that is configured to support a patient on whom the medical procedure is to be performed as further described herein. Alternatively, the robotic device can be an autonomous robot with humanoid features (e.g., arms, transport elements, head, base, etc.).

The robotic system 102 can include a robotic arm with two or more segments coupled together via joints, as further detailed with reference to FIG. 3. Joints can allow one or more degrees of freedom. For example, joints can provide for translation along and/or rotation of the robotic arm about one or more axes. In some embodiments, one end segment of the robotic arm can include a coupling element. The coupling element can couple the robotic arm to the manipulation device 130. The other end segment of the robotic arm can be disposed on, affixed to, mounted on, and/or integrated with at least a portion of the robotic system 102.

In some embodiments, the robotic arm can be disposed on, affixed to, mounted on, and/or integrated with a base (e.g., base of an autonomous and/or semi-autonomous cart) of the robotic system 102, as further detailed with reference to FIG. 2. In some embodiments, the base can carry the robotic arm, one or more I/O device(s) 104, and one or more sensor(s) 106. The base can be a movable base with one or more transport elements that can provide for translation along and/or rotation of the robotic system 102 along one or more axes. Additionally or alternatively, the base can be configured to be stationary. In some embodiments, the base can be configured to raise vertically so as to position the robotic arm at an appropriate height with respect to a subject (e.g., a patient on whom the medical procedure is to be performed). In some embodiments, the base can include a locking mechanism to lock the movement of the transport elements and/or the movement of the base itself.

In some embodiments, the robotic system 102 can include a communication interface to enable communication with the I/O device(s) 104 and/or the sensor(s) 106. In some embodiments, the robotic system 102 can include a control unit to control the robotic system 102 (e.g., to control the base, robotic arm, etc.).

The robotic system 102 is described as a robotic arm disposed on, affixed to, mounted on, and/or integrated with a base solely for illustrative purposes. It should be readily understood that the robotic system 102 can be any suitable robotic component (e.g., robotic cart, humanoid robot, etc.) that can be coupled to one or more manipulation devices 130. For instance, the robotic system 102 can include multiple robotic arms that form a part of the robotic system 102. Each robotic arm can be coupled to a respective manipulation device. In such a scenario, the robotic system 102 may be configured to perform the medical procedure on multiple subjects substantially simultaneously. Additionally or alternatively, the robotic system 102 may include a robotic arm without a base. Additionally or alternatively, the robotic system 102 can be an autonomous humanoid robot (e.g., a robot with humanoid features such as head, transport elements, manipulation elements, etc.) with a robotic arm for facilitating vascular access.

In some embodiments, the manipulation device 130 can be coupled to the robotic system 102 via a coupling element. The manipulation device 130 can be configured to drive movement of one or more components (e.g., a catheter, a needle, and/or a guidewire) to facilitate vascular access. The coupling element can include any type of mechanism that can couple the manipulation device 130 to the robotic system 102, such as, for example, a mechanical mechanism (e.g., a fastener, a latch, a mount, a joint), a magnetic mechanism, a friction fit, etc. The manipulation device 130 can be attached to a cartridge assembly (further described with reference to FIG. 5) that can include a needle, a catheter, and/or a guidewire to perform the medical procedure. In some embodiments, the manipulation device 130 can include one or more actuators that can actuate each of the needle, the catheter, and the guidewire. The actuators can enable the manipulation device 130 to perform the medical procedure. The one or more actuators can be any suitable type of actuator. For instance, the one or more actuators can include linear actuators with magnetic encoders.

In some embodiments, the robotic system 102 can include an imaging device (e.g., ultrasound array) to provide a user (e.g., an operator, a surgeon, etc.) with visual aid (e.g., ultrasound images showing traverse view and/or longitudinal view) as the medical procedure is performed (e.g., ultrasound images of the needle, the catheter, and/or the guidewire being inserted into a blood vessel of a subject). In some embodiments, the imaging device can be integrated and/or form part of the manipulation device, as further detailed with reference to FIG. 5.

The manipulation device 130 and/or the robotic system 102 can be communicably coupled to one or more I/O device(s) 104. An I/O device(s) 104 can be any suitable input device that can be configured to receive inputs from the user and/or any suitable output device that can be configured to send outputs to other devices and/or the user operating the robotic system 102. In some embodiments, the I/O device(s) 104 can be an integrated computing device that includes one or more components to both receive inputs and send outputs. Some non-limiting examples of integrated computing device that can receive inputs from the user and send outputs to the user and/or to other devices can include computers (e.g., desktops, personal computers, laptops etc.), tablets and e-readers (e.g., Apple iPad®, Samsung Galaxy® Tab, Microsoft Surface®, Amazon Kindle®, etc.), mobile devices and smart phones (e.g., Apple iPhone®, Samsung Galaxy®, Google Pixel®, etc.), etc.

In some embodiments, the I/O device(s) 104 can be a user control such as a joystick, a remote user control, keyboard, trackball, etc. that can receive input from the user. In some embodiments, the I/O device(s) 104 can be an audio device such as a microphone and/or a speaker that receives audio input from the user. In such embodiments, the I/O device(s) 104 can additionally include a display device (e.g., a display, a touch screen, etc.) that displays output to the user.

The manipulation device 130 and/or the robotic system 102 can be optionally coupled to one or more sensor(s) 106. The sensor(s) 106 can be configured to capture image data of the at least a part of the robotic system 102, the manipulation device 130, and/or at least a part of the subject as the robotic system 102 performs the medical procedure on the subject. The sensor(s) 106 can be an image sensor such as visual camera, stereo camera array, etc. The sensor(s) 106 can be operable to capture two-dimensional and/or three-dimensional images of the robotic system 102, the manipulation device 130, and/or the subject. In some embodiments, the sensor(s) 106 can be operated remotely by the user. For instance, the user can be in a location away from the system 100, and the sensor(s) can be configured to be controlled remotely using one of the I/O device(s) 104. Alternatively, in some embodiments, the user can be in a location proximate to the system 100 and may not require any sensor(s) 106. In some embodiments, a user proximate to the system 100 can also operate and/or adjust one or more sensor(s) 106 of the system 100, e.g., one or more image sensors, to capture views of the environment for one or more remote users and/or for tracking/monitoring purposes.

In some embodiments, the sensor(s) 106 can be mounted on and/or can otherwise be an integral part of the I/O device(s) 104. For instance, the sensor(s) 106 can be attached to, coupled to, and/or otherwise be a part of the I/O device(s) 104. In some embodiments, the sensor(s) 106 can be mounted on the robotic system 102 itself The sensor(s) 106 can be operable to move (e.g., rotational and/or translational motion) such that the sensor(s) 106 can capture image data from various angles. For instance, the sensor(s) 106 can be mounted on a pan/tilt mechanism to capture the image data. In some embodiments, the sensor(s) 106 can be a portable device such as a handheld computer tablet, a smartphone with camera, or a digital camera that is attached to, mounted on, and/or otherwise a part of the system 100.

In order to perform the medical procedure, the I/O device(s) 104 (e.g., user control such as joystick, keyboard, remote control, trackball, etc.) can receive an input from the user. The input can be transmitted to the robotic system 102 and/or the manipulation device 130. For instance, the I/O device(s) 104 can receive an input to advance the needle, catheter, and/or guidewire into a blood vessel. The input can be transmitted from the I/O device(s) to the robotic system 102 via a communications interface. The robotic system 102 can cause the actuators in the manipulation device 130 to actuate the needle, catheter, and/or guidewire (e.g., included in a cartridge assembly) based on the input. The imaging device (e.g., ultrasound array) included in the manipulation device can provide a visual aid of the movement (e.g., the advancement) of the needle, catheter, and/or guidewire into the blood vessel. The visual aid (e.g., ultrasound images showing traverse view and/or longitudinal view) may be displayed on the I/O device(s) 104 (e.g., display device). Subsequent input representing subsequent movement of the manipulation device 130 or one or more components in the manipulation device 130 (e.g., actuators actuating needle, catheter, and/or guidewire) can be provided to the I/O device(s) 104 based on the visual aid. For example, if the position of the needle, catheter, and/or guidewire in the blood vessel is incorrect, the visual aid (e.g., ultrasound images showing traverse view and/or longitudinal view) can guide the user to modify the input so that such component(s) advance to an appropriate location in the blood vessel.

In some embodiments, the sensor(s) 106 (e.g., camera) can provide image data of the robotic system 102, the manipulation device 130, and the subject to the user. The user can remotely control the manipulation device 130 based on the image data. For example, the image data may include images of the portion of the body of the subject that includes the blood vessel and the orientation and/or position of the manipulation device 130 with respect to the portion of the body. If the orientation and/or position of the manipulation device 130 with respect to the portion of the body is incorrect, the user can remotely control the manipulation device 130 (e.g., by sending instructions to the robotic system 102 via the I/O device(s) 104) so as to orient and/or position the manipulation device 130 as desired.

In some embodiments, the user can control the sensor(s) 106 remotely using the I/O device(s) 104. For instance, if the captured image data does not include images of the manipulation device 130 or the portion of the body, then the sensor(s) 106 can be remotely controlled by the user such that the angle of the sensor(s) 106 can be changed so as to capture the images of both the manipulation device 130 and the portion of the body. For example, the pan/tilt mechanism on which the sensor(s) is mounted can be remotely controlled by the I/O device(s) so as to capture the images as desired.

Subsequent inputs such as input to advance the needle, catheter, and/or guidewire can be provided remotely through the I/O device 104 based on the image data and the visual aid (e.g., ultrasound images) obtained from the imaging device (e.g., ultrasound array). In some embodiments, the robotic system 102 can be configured to automatically (e.g., via the control unit in the robotic system 102) adjust the position and/or orientation of the manipulation device 130 or one or more components of the manipulation device 130 based on the image data and the visual aid. In this manner, the robotic system 102 along with the manipulation device 130 can perform the vascular access procedure (e.g., the Seldinger technique) in an automated and/or a semi-automated manner such as with the user controlling the I/O device(s) 104 that in turn controls and actuates the robotic system 102 and/or the manipulation device 130.

Robotic System

Figure 2:
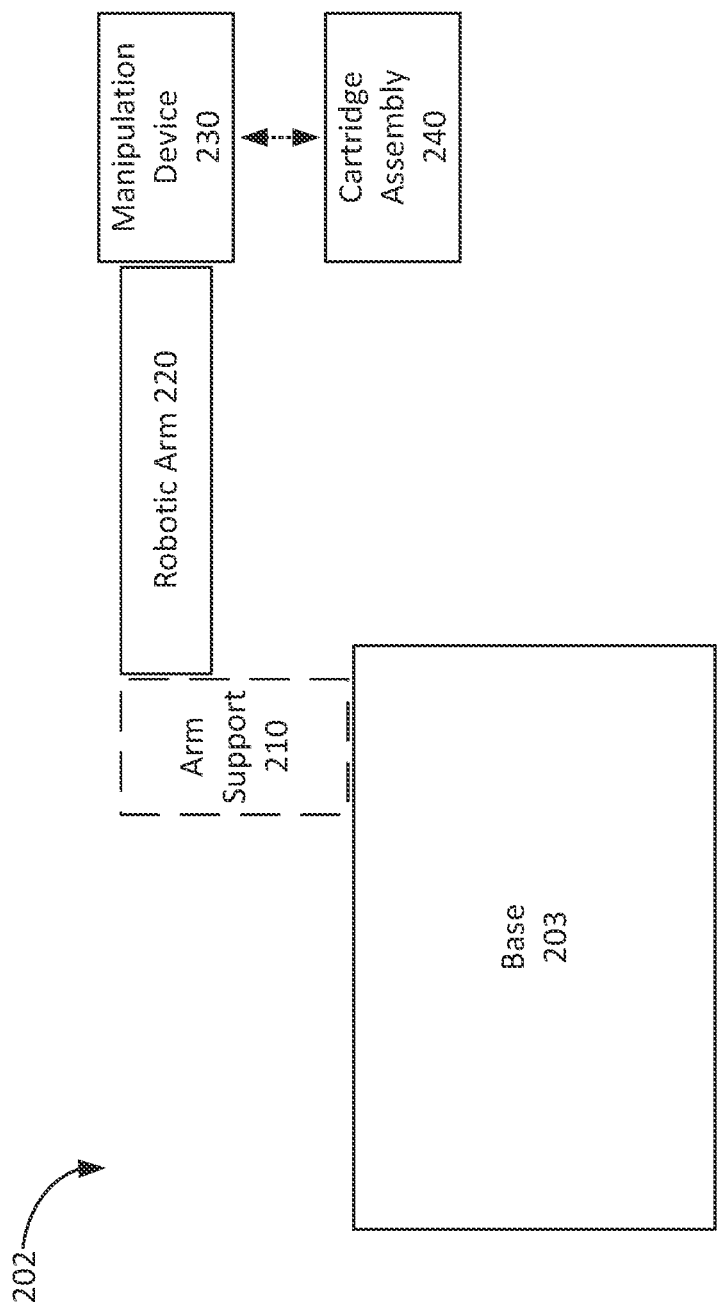
FIG. 2 a block diagram that illustrates a system for facilitating vascular access, according to some embodiments.

FIG. 2 is a block diagram that illustrates a robotic system 202 of a vascular access system, according to some embodiments. The robotic system 202 can be functionally and/or structurally similar to other robotic systems described herein, such as, for example, robotic system 102 in FIG. 1. The robotic system 202 can include a base 203. The base 203 can be mechanically coupled to a robotic arm 220 (e.g., similar to the robotic arm as described with reference to FIG. 1) via an arm support 210. The robotic arm 220 can be coupled to and/or integrated with a manipulation device 230. In some embodiments, a cartridge assembly 240 can be attached to the manipulation device 230.

Base

The base 203 can be any suitable base for positioning a manipulation device 230 of the vascular access system. For example, the base 203 can be a chassis supporting the robotic arm 220 and the manipulation device 230. In such scenarios, one or more electronic components such as a control unit, a communications interface, etc. can be attached to and/or coupled to the base 203 (e.g., chassis). Alternatively, the base 203 can be a structure supporting the robotic arm 220 and the manipulation device 230 that houses one or more electronic components such as a control unit, a communications interface, etc. within the base 203. Put differently, the outer structure of the base 203 can be a housing that encloses one or more electronic components. The robotic arm 220 and the manipulation device 230 can be supported on the outer structure. In some embodiments, the base 203 can be a surface with a flat portion configured to support a patient on whom the medical procedure is to be performed. For example, the base 203 can be a bed configured to support the patient. Additionally or alternatively, the base 203 can be a platform configured to support the patient. A first portion of the robotic arm 220 can be coupled to the base 203 (e.g., bed, chassis, etc.). A second portion of the robotic arm (e.g., a second portion opposite the first portion) can be coupled to the manipulation device 230. In some embodiments, the second portion of the robotic arm 220 coupled to the manipulation device 230 can be movable relative to the base 203 to position the needle, the guidewire, and the catheter for insertion into the target vessel of the patient.

Figure 4:
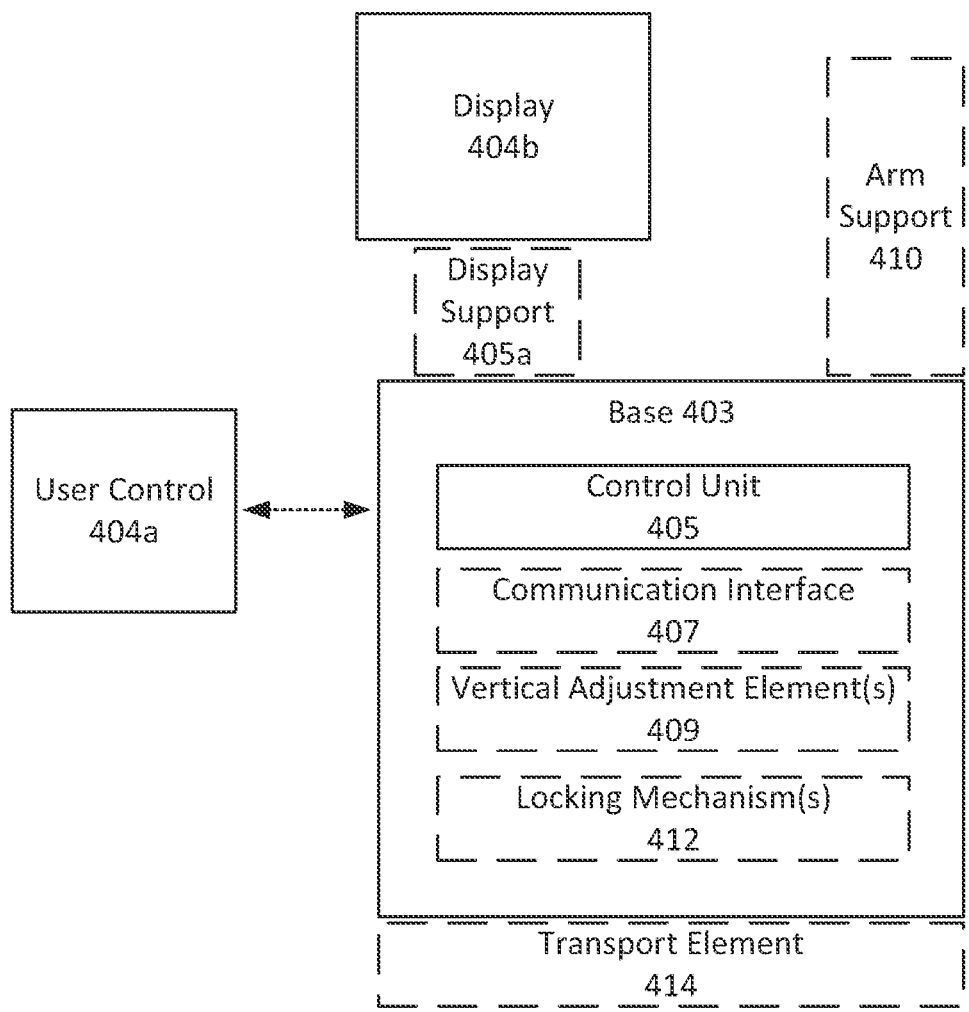
FIG. 4 is a block diagram the illustrates a base of a system for facilitating vascular access, according to some embodiments.

FIG. 4 is a block diagram the illustrates a base 403 (e.g., structurally and/or functionally similar to base 203 in FIG. 2 and/or other bases described herein), according to some embodiments. In some embodiments, the bottom surface of the base 403 can include transport elements 414 that can provide for translation along and/or rotation of the robotic system (e.g., robotic system 202 in FIG. 2) along one or more axes. Transport elements 414 can be any suitable components configured for movement such as, for example, a wheel, a swivel caster, a track, etc. Transport elements can enable the robotic system 202 to move around.

For instance, the transport elements 414 can be swivel casters (e.g., 4 swivel casters coupled to 4 corners of the base 403) that provide three degrees of freedom to the robotic system 202. The swivel casters can allow for linear translations of the robotic system 202 along two axes and rotation of the robotic system 202 along one axis. These three degrees of freedom can enable a user (e.g., a surgeon and/or an operator) to achieve planar and rotational positioning of the base 403 and thereby planar and rotational positioning of the robotic system 202 relative to a portion of a subject's body (e.g., arm, etc., on which the medical procedure is to be performed).

In some embodiments, the base 403 can include vertical adjustment elements 409 to move (e.g., raise or drop) the base vertically so as to position the robotic arm 220 and the manipulation device 230 at an appropriate height with respect to a subject (e.g., a patient on whom the medical procedure is to be performed). This can provide the robotic system 202 with a fourth degree of freedom. In some embodiments, the vertical adjustment elements 409 can include mechanical features to lift a top surface of the base 403 and/or drop the top surface of the base 403 to a specific height. For example, the vertical adjustment elements 409 can include linear rails with recirculating balls to adjust a height of the top surface of the base 403. In some embodiments, the vertical adjustment elements 409 can include an actuator such as ball screw actuator to move the base vertically. For instance, the ball screw actuator can move the top surface of the base 403 vertically to a desired height. Once the desired height is reached, a fail-safe brake can hold the position of the top surface while the linear rails with recirculating balls can constraint the movement of the base 403. In other embodiments, the top surface of the base 403 can be moved manually by manually adjusting the linear rails and the recirculating balls.

In some embodiments, the base 403 can include a locking mechanism 412 to lock the movement of the base 403. For instance, once a user positions the robotic system 202 at an appropriate position (e.g., distance and/or height) with respect to the subject, the locking mechanism can be engaged to lock the position of the base 403 and the robotic system 202. The locking mechanism 412 can lock the transport elements 414 (e.g., swivel casters) preventing the transport elements 414 from moving further. In some embodiments, the locking mechanism 412 can automatically engage a lock. For instance, the locking mechanism 412 can automatically lock the transport elements 414 as soon as the robotic system 202 is positioned at a desired location.

In some embodiments, the base 403 can include a communications interface 407. The communication interface 407 can be any suitable component that enables the base 403 and/or the robotic system 202 to communicate with I/O device(s) (e.g., I/O device(s) 104 in FIG. 1), sensor(s) (e.g., sensor(s) 106 in FIG. 1), or other suitable devices. In some embodiments, communication interface 407 can further enable the I/O device(s) to communicate with the transport elements 414, vertical adjustment elements 409, and locking mechanism 412. In some embodiments, the I/O device(s) can include a user control 404a and/or a display 404b, as further detailed below.

In some embodiments, the base 403 can include a control unit 405 to control one or more components of the robotic system (e.g., robotic system 202 in FIG. 2) such as the base 403, the robotic arm (e.g., robotic arm 220 in FIG. 2), the manipulation device (e.g., manipulation device 230 in FIG. 2), the cartridge assembly (e.g., cartridge assembly 240 in FIG. 2), and/or a combination thereof. Control unit 405 can be any suitable processing device configured to run and/or execute functions associated with controlling one or more components of the robotic system. Control unit 405 can include any suitable processor(s) that can be configured to execute modules, functions, and/or processes. In some embodiments, the processor(s) can be a general purpose processor, a Field Programmable Gate Array (FPGA), an Application Specific Integrated Circuit (ASIC), a Digital Signal Processor (DSP), and/or the like.

As discussed above, the base 403 can support the robotic arm (e.g., robotic arm 220 in FIG. 2) and/or one or more I/O device(s) (e.g., I/O device(s) 104 in FIG. 1). For example, the base 403 can be coupled to the robotic arm via arm support 410. One or more I/O device(s) such as, for example, user control 404a and display 404b can be communicably coupled to the base 403. In some embodiments, the display 404b can additionally be mechanically coupled to the base 403 via the display support 405a. Display support 405a can be any suitable support that can attach and/or couple display 404b to the base 403 such that the base 403 supports the display 404b. In some embodiments, display support 405a can enable adjustment(s) to be made to the position and/or orientation of the display 404a. Display 404b can be any suitable display device such as touch screen, device displaying a graphical user interface, audio device (e.g., microphone, speaker, etc.), a combination thereof, and/or the like.

In some embodiments, the user control 404a can additionally be attached to and/or integrated with the base 403. For instance, user control 404a can be integrated with the base 403 such that the base 403 supports the user control 404a. User control 404a can be any suitable device that can receive input from the user such as a joystick, a remote user control, keyboard, trackball, etc.

Robotic Arm

Referring back to FIG. 2, the base 203 can be coupled to the robotic arm 220 via an arm support 210. The robotic arm 220 can comprise of two or more segments coupled together via joints. One end segment can be coupled via a joint to the arm support 210. The other end segment can be integrated with and/or coupled to the manipulation device 230. In some embodiments, the robotic arm 220 can be actuated by one or more motors. In some embodiments, the robotic arm 220 can include one or more sensors to measure sensory information, including information relating to the robotic arm 220. Examples of sensors include position encoders, torque and/or force sensors, touch and/or tactile sensors, etc. The sensors can be disposed on or integrated with either the segments, or the joints, or a combination of both. The sensory information can be transmitted to a control unit (e.g., control unit 405 in FIG. 4) included in or attached to the base 203. Additionally or alternatively, the sensory information can be transmitted to one or more I/O device(s) (e.g., I/O device(s) 104 in FIG. 1).

Figure 3:
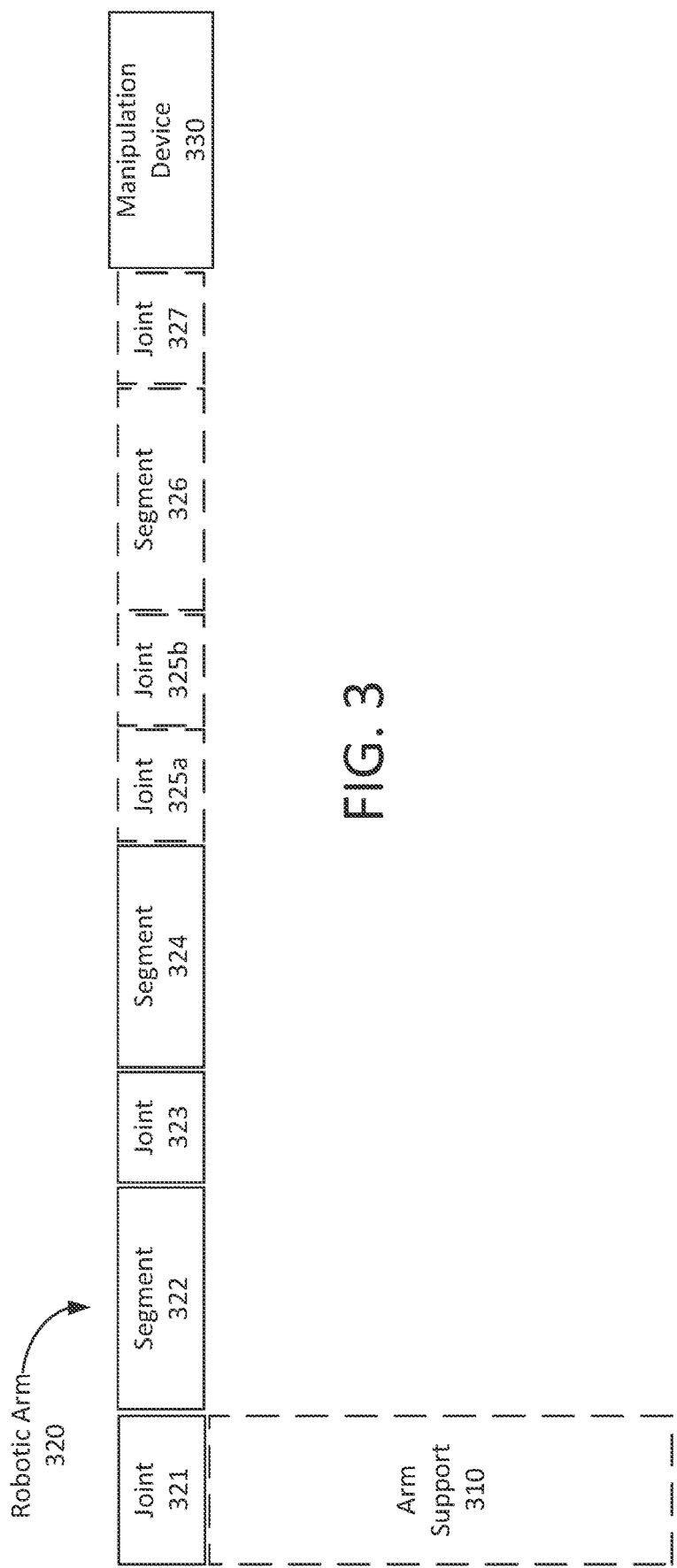
FIG. 3 is a block diagram the illustrates a robotic arm of a system for facilitating vascular access, according to some embodiments.

FIG. 3 is a block diagram the illustrates a robotic arm 320 (e.g., structurally and/or functionally similar to robotic arm 220 in FIG. 2 and/or other robotic arms described herein), according to some embodiments. In some embodiments, robotic arm 320 can be implemented as an arm that includes two segments 322 and 324. Arm support 310 (e.g., similar to arm support 210 in FIG. 2) and segment 322 can be coupled together via joint 321. Segments 322 and 324 are coupled together via joint 323. In some embodiments, the robotic arm can optionally include segment 326. Segments 326 and segment 324 can be coupled together via joints 325a and 325b. In some embodiments, the manipulation device 330 (e.g., manipulation device 230 in FIG. 2) and segment 326 can be coupled together via joint 327. In other embodiments (e.g., embodiments that may not include segment 326), the manipulation device 330 and segment 324 can be coupled together via joint 325a. In yet other embodiments, the manipulation device 330 can be integrated with segment 324 or segment 326.

In some embodiments, the robotic arm 320 can have three proximal axes. A first proximal axis can be along arm support 310 that enables vertical translation of the robotic arm 320 along the arm support 310. A second proximal axis can be along joint 321. A third proximal axis can be along joint 323. The three proximal axes can allow translation of the robotic arm 320 along the three-dimensional space. In some embodiments, the robotic arm can have three distal axes. A first distal axis can be along joint 325a, a second distal axis can be along joint 325b, and a third distal axis can be along joint 327. The three distal axes can allow rotation of the robotic arm 320 along the three-dimensional space (e.g., pitch, yaw, and roll). In this manner, the robotic arm can have six degrees of freedom. In some embodiments, the second proximal axis along joint 321, the third proximal axis along joint 323, and the first distal axis along 325a can comprise a planar Selective Compliance Articulating Robot Arm (SCARA) linkage. While three segments and five joints are depicted in FIG. 3, one of ordinary skill in the art would understand that a robotic arm can include a different number of segments and/or joints.

In some embodiments, the robotic arm 320 can include locking mechanisms for locking one or more components of the robotic arm 320. For example, the robotic arm can include one or more pulleys, magnets, etc. for locking one or more joints and/or a height of the robotic arm 320 relative to a base of a robotic system (e.g., base 403).

Manipulation Device and Cartridge Assembly

Referring back to FIG. 2, an end segment of the robotic arm 220 can be coupled to the manipulation device 230. The manipulation device 230 can be attached to a cartridge assembly 240. Further details of the components of an example manipulation device and an example cartridge assembly are described below.

Figure 5:
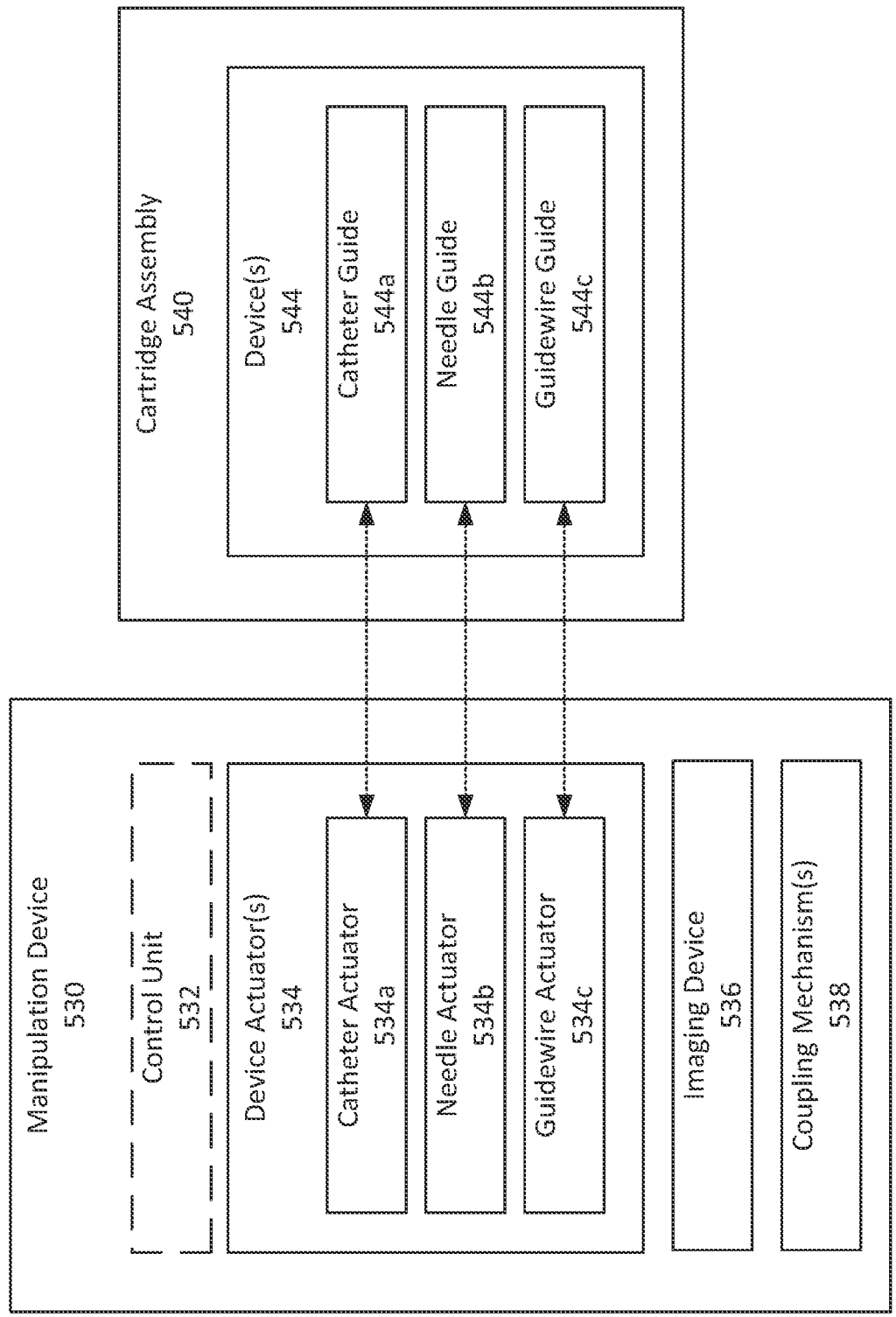
FIG. 5 is a block diagram the illustrates components of a manipulation device and a cartridge assembly and interactions therebetween, according to some embodiments.

FIG. 5 is a block diagram that illustrates a manipulation device 530 (e.g., similar to manipulation device 230 in FIG. 2 and/or other manipulation devices described herein) and a cartridge assembly 540 (e.g., similar to cartridge assembly in FIG. 2 and/or other cartridge assemblies described herein), according to some embodiments. In some embodiments, the manipulation device 530 can include a coupling mechanism 538, an imaging device 536, a portion of one or more device actuator(s) (e.g., catheter actuator 534a, needle actuator 534b, and guidewire actuator 534c), collectively referred to as device actuator(s) 534, and optionally a control unit 532.

In some embodiments, the cartridge assembly 540 can include the device(s) 544 such as a catheter, a needle, and/or a guidewire. Alternatively, the manipulation device 530 can include some of the device(s) 544 while the cartridge assembly 540 can include other device(s) 544. For instance, the manipulation device 530 can include a catheter and a guidewire while the cartridge assembly 540 can include the needle. Similarly, the manipulation device 530 can include the guidewire and the needle while the cartridge assembly 540 can include the catheter. In a similar manner, any suitable permutation of the catheter, the needle, and the guidewire in the manipulation device 530 and/or the cartridge assembly 540 can be possible. In some embodiments, the guidewire, the needle, and the catheter can be arranged coaxially in the manipulation device 530. For example, the guidewire can be disposed within a lumen of the needle and the needle can be disposed within a lumen of the catheter. In some embodiments, a length of the catheter can be about 40 mm. In some embodiments, a length of the needle can be a little more than 40 mm (40 mm plus bevel length) such that the needle can extend past the catheter. In some embodiments, the guidewire can be 142 mm long such that at least 50 mm of the guidewire can extend past the needle tip. In some embodiments, the cartridge assembly 540 can be configured to store the guidewire in a linear state.

In some embodiments, the cartridge assembly can also include another portion of the one or more device actuator(s) (e.g., catheter actuator 534a, needle actuator 534b, and guidewire actuator 534c), collectively referred to as device actuator(s) 534.

The imaging device 536 in the manipulation device 530 can provide the user with a visual aid of a blood vessel as the medical procedure is being performed. For example, the imaging device can be any suitable imaging device that can capture a visual representation of the blood vessel. Some non-limiting example of the imaging device 536 can include ultrasound imaging device, fluoroscopes, cameras, etc.

In some embodiments, the imaging device 536 can be an ultrasound array located on the manipulation device 230. The ultrasound array can provide two-dimensional ultrasound images along a longitudinal plane and a transverse plane. The ultrasound images with the transverse view of a blood vessel can show the radial cross section of the blood vessel and the longitudinal view of the blood vessel can show the axial cross section of the blood vessel. In some embodiments, the imaging device 536 can be configured to obtain three-dimensional ultrasound images of the blood vessel.

The manipulation device 530 can include a portion of one or more device actuator(s) 534. The device actuator(s) 534 can be configured to actuate the needle, the catheter, and/or the guidewire. For example, the manipulation device 530 can include linear actuators to actuate the device(s) 544. The linear actuators can include a motor such as a brushless DC motor fixed to a ball screw shaft supported by ball screw bearings. A magnetic encoder coupled to the motor can sinusoidally commutate the motor. A linear circulating ball bearing can be coupled to a ball screw nut that is fixed on the ball screw shaft. For instance, the linear circulating ball bearing can be coupled to the ball screw nut on the ball screw shaft via a carriage block. As the ball screw shaft rotates (e.g., owing to the rotation of the motor's rotor), the ball screw nut translates as it is constrained by the linear circulating ball bearing through the carriage block. The translation of the ball screw nut can in turn actuate a device(s) 544 along a linear axis. Accordingly, each of the needle, catheter, and guidewire can be actuated along a linear axis by a respective linear actuator.

Each of the needle, catheter, and guidewire can be attached to a respective guide that guides the device(s) 544 along the linear axis as the device(s) are being actuated by the linear actuators (e.g., device actuator(s) 534 included in manipulation device 530). Therefore, the guides form another portion of the one or more device actuator(s) 534. In some embodiments, the guides can be included in the cartridge assembly 540 and can be attached to the respective device(s) 544. For example, a needle guide 544b included in the cartridge assembly 544 can be attached to the needle, a catheter guide 544a included in the cartridge assembly 544 can be attached to the catheter, and a guidewire guide 544c included in the cartridge assembly 544 can be attached to the guidewire. In some embodiments, the catheter guide 544a, the needle guide 544b, and the guidewire guide 544c can each include a coupling element that can couple with the coupling mechanism 538 in the manipulation device 530. For example, the catheter guide 544a, the needle guide 544b, and the guidewire guide 544c can each include a puck. In some embodiments, the puck can comprise a magnetic element and/or a magnetic portion (e.g., embedded steel disk).

The manipulation device 530 can include coupling mechanism 538 that couples the cartridge assembly 540 (e.g., the coupling element in the cartridge assembly 540) to the manipulation device 530, such as, for example, a mechanical mechanism (e.g., a fastener, a latch, a mount), a magnetic mechanism, a friction fit, etc. In some embodiments, the coupling mechanism can be a magnetic mechanism. For instance, consider the example embodiment described above with the portion of device actuator(s) 534 included in the manipulation device 530 being linear actuators. The ball screw shaft in the linear actuator can be coupled to a carriage block. A magnet (e.g., ferromagnet, permanent electromagnet, etc.) can be fixed to the carriage block. The coupling element (e.g., puck) included in the guide(s) 544a, 544b, 544c can be aligned with the carriage block. The magnet in the carriage block engages the coupling element (e.g., puck) in the cartridge assembly 540 with the carriage block in the manipulation device 530. In some embodiments, the magnetic portion in the coupling element (e.g., puck) can act as an armature to close the magnetic circuit in the magnet, thereby engaging the coupling element in the cartridge assembly 540 with the manipulation device 530.

In some embodiments, the coupling mechanism 538 can be a mechanical mechanism. For example, the coupling mechanism 538 can include slots (e.g., recessed portions in the manipulation device 530) such that the catheter guide 544a, the needle guide 544b, and the guidewire guide 544c included in the cartridge assembly 540 can fit within the slots. In some embodiments, the coupling mechanism 538 can be a combination of the magnetic mechanism and the mechanical mechanism.

In some embodiments, the manipulation device 530 can optionally include a control unit 532 to control the actuation of the device actuator(s) 534. Control unit 532 can be any suitable processing device configured to run and/or execute functions associated with controlling the device actuator(s) 534. Control unit 532 can include any suitable processor(s) that can be configured to execute modules, functions, and/or processes. In some embodiments, the processor(s) can be a general purpose processor, a Field Programmable Gate Array (FPGA), an Application Specific Integrated Circuit (ASIC), a Digital Signal Processor (DSP), and/or the like.

Methods

Figure 6:
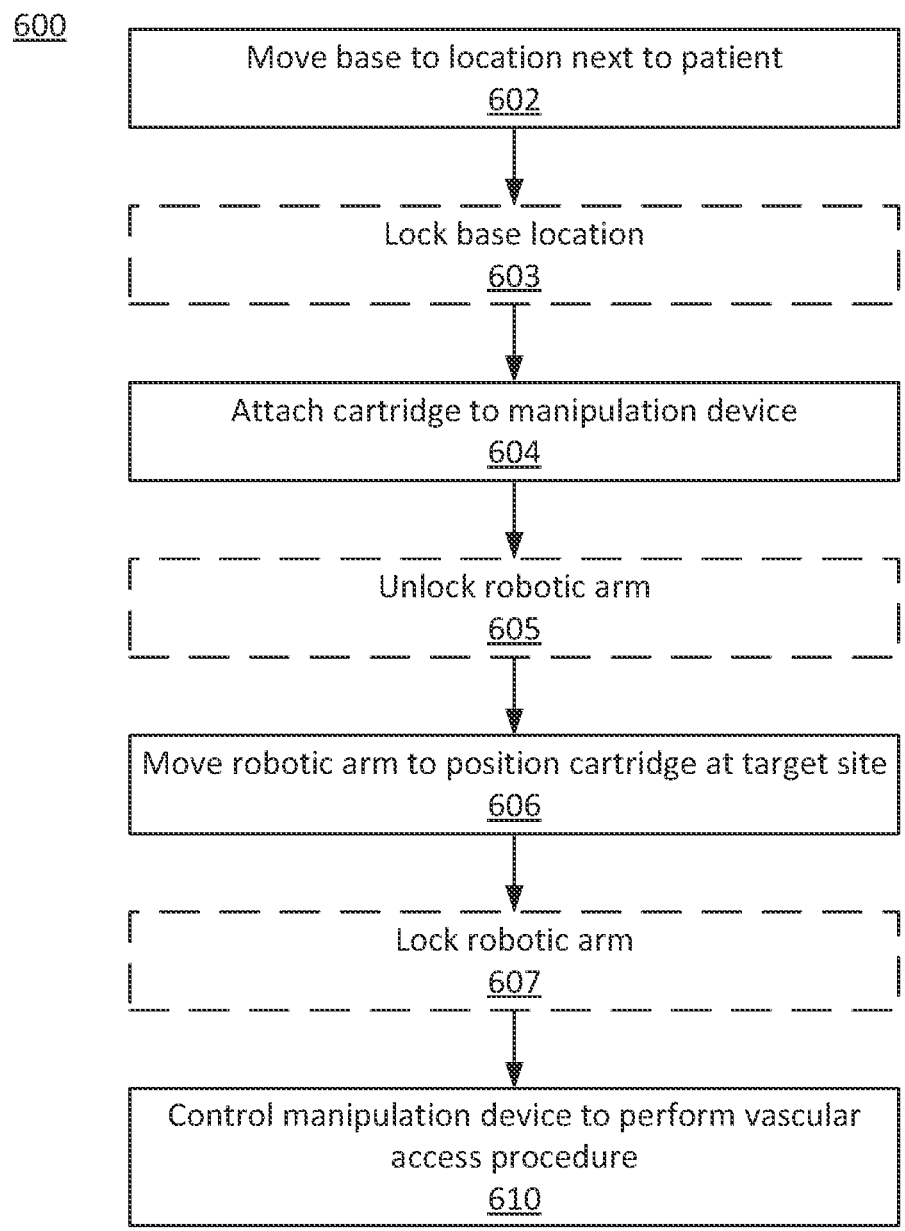
FIG. 6 is a flow diagram illustrating a method of performing a vascular access procedure, in accordance with some embodiments.

FIG. 6 is a flow diagram illustrating a method 600 of performing a medical procedure (e.g., using system 100 in FIG. 1), in accordance with some embodiments. A robotic system, such as, for example, robotic system 102 in FIG. 1 and/or any of the other robotic systems described herein, can perform the medical procedure (e.g., vascular access procedure) in an automated and/or semi-automated manner. At 602, a base (e.g., base 203 in FIG. 2 or base 403 in FIG. 4) can be moved to a location next to a subject (e.g., a patient). As discussed above, the base can include transport elements (e.g., swivel casters) that can allow for translational and rotational movement of the robotic system. The base can be moved to a suitable position from the subject such that the medical procedure can be performed on the subject. For example, the base can be moved to a position that allows a robotic arm (e.g., robotic arm 220 in FIG. 2 or robotic arm 320 in FIG. 3) access a portion of the subject's body (e.g., patient's arm on which the medical procedure is to be performed). In some embodiments, the base can be moved to position the robotic arm such that at least a portion of the manipulation device and/or the cartridge assembly touches the skin of the subject. In some embodiments, an I/O device (e.g., I/O device(s) 104 in FIG. 1 or user control 404a in FIG. 4) communicably coupled to the base and/or communicably coupled to the transport elements included in the base can transmit instructions to move the base. For example, the I/O device can be configured to transmit instructions to an actuator controlling the movements of the swivel caster. In other embodiments, the base can be moved manually by a user.

In some embodiments, the base can be moved up or dropped down in a vertical manner so as to position the base and/or the robotic arm suitably in order to perform the medical procedure. As discussed above, the base can include vertical adjustment element(s) (e.g., vertical adjustment element(s) 409 in FIG. 4) to adjust a height of a top surface of the base. In some embodiments, an I/O device (e.g., I/O device(s) 104 in FIG. 1 or user control 404a in FIG. 4) communicably coupled to the base and/or communicably coupled to the vertical adjustment element(s) can transmit instructions to adjust the height of the top surface of the base. For example, the I/O device can be configured to transmit instructions to an actuator controlling the vertical adjustment element(s). In other embodiments, the vertical adjustment element(s) can be manipulated manually by a user so as to adjust the height of the top surface of the base. Once the base is moved to a suitable location from the subject (e.g., suitable distance and/or suitable height), the base can be locked (e.g., using locking mechanism(s) 412 in FIG. 4) to lock the location of the base (at 603 in FIG. 6).

At 604, a cartridge assembly (e.g., cartridge assembly 240 in FIG. 2 or cartridge assembly 540 in FIG. 5) can be attached to a manipulation device (e.g., manipulation device 130 in FIG. 1, manipulation device 230 in FIG. 2, manipulation device 330 in FIG. 3, or manipulation device 530 in FIG. 5). The manipulation device can be coupled to or otherwise be a part of the robotic arm. In some embodiments, the manipulation device can include coupling mechanism(s) (e.g., coupling mechanism(s) 538 in FIG. 5) to couple the cartridge assembly to the manipulation device. For example, the manipulation device can include a permanent electromagnet that magnetically couples the manipulation device to the cartridge assembly. A coupling element (e.g., puck) in the cartridge assembly can comprise a magnetic portion (e.g., an embedded stainless steel disk) that can close a magnetic circuit with the magnet (e.g., permanent electromagnet). In this manner, the cartridge assembly can be attached to the manipulation device. Additionally or alternatively, the manipulation device can include recessed portions (e.g., slots) to receive portions of the cartridge assembly. For instance, the device(s) (e.g., device(s) 544 in FIG. 5) along with guide(s) (e.g., device actuator(s) 534 in FIG. 5) can be configured to fit within the recessed portions of the manipulation device. In this manner, the cartridge assembly can be mechanically coupled to the manipulation device.

In some embodiments, the robotic arm can include locking mechanisms to lock and unlock the robotic arm. Locking the robotic arm can prevent further movement of the robotic arm. Unlocking the robotic arm can enable the robotic arm to move as desired. In some embodiments, at 605, the method 600 can include unlocking the robotic arm if the robotic arm is in locked position.

At 606, the method 600 can include moving the robotic arm to position the cartridge assembly at target site. The target site can be a portion of a subject's body on which the medical procedure is to be performed. For example, the target site can be an arm of a patient's body on which the Seldinger technique is to be performed. Moving the robotic arm can include positioning the cartridge assembly at a desired location relative to the target site. For instance, the cartridge assembly can be positioned at an angle with respect to a blood vessel in the target site (e.g., patient's arm). In some embodiments, the angle can be between about 0 degrees and about 90 degrees, between about 10 degrees and about 80 degrees, between about 20 degrees and about 70 degrees, between about 30 degrees and about 60 degrees, between about 40 degrees and about 50 degrees with respect to the blood vessel. In some embodiments, the angle can be between about 20 degrees and about 60 degrees. Additionally or alternatively, the cartridge assembly can be positioned at a specific distance from the blood vessel. In some embodiments, the robotic arm can be moved to position the cartridge assembly such that at least a portion of the cartridge assembly touches the skin of the subject. In some embodiments, moving the robotic arm can include transmitting instructions from an I/O device to the robotic system and/or the robotic arm. For instance, a user can transmit instructions to move the robotic arm via an input device such as joystick, mouse, keyboard, buttons, etc. Once the robotic arm is moved to position the cartridge assembly at the target site, at 607, the robotic arm can be locked to prevent further movement.

At 610, the method 600 can include controlling the manipulation device to perform a vascular access procedure, e.g., the Seldinger technique. In some embodiments, an I/O device (e.g., I/O device(s) 104 in FIG. 1 or user control 404a in FIG. 4) communicably coupled to the robotic system can transmit instructions to the robotic system (e.g., a control unit included in the robotic system) so as to control the movement of the robotic arm. For instance, a control unit (e.g., control unit 405 in FIG. 4) included in the robotic system (e.g., control unit in the base, control unit in the robotic arm, etc.) can process instructions (e.g., instructions from the I/O device) to control the manipulation device. For example, the needle, the catheter, and/or the guidewire can be actuated based on the instructions. Feedback from sensor(s) (e.g., sensor(s) 106 in FIG. 1) and/or imaging device (e.g., imaging device 536 in FIG. 5) can be used for further subsequent control of the manipulation device. For instance, subsequent control of the actuation of the needle, the catheter, and/or the guidewire can be based on feedback from sensor(s) and/or the imaging device.

Figure 7:
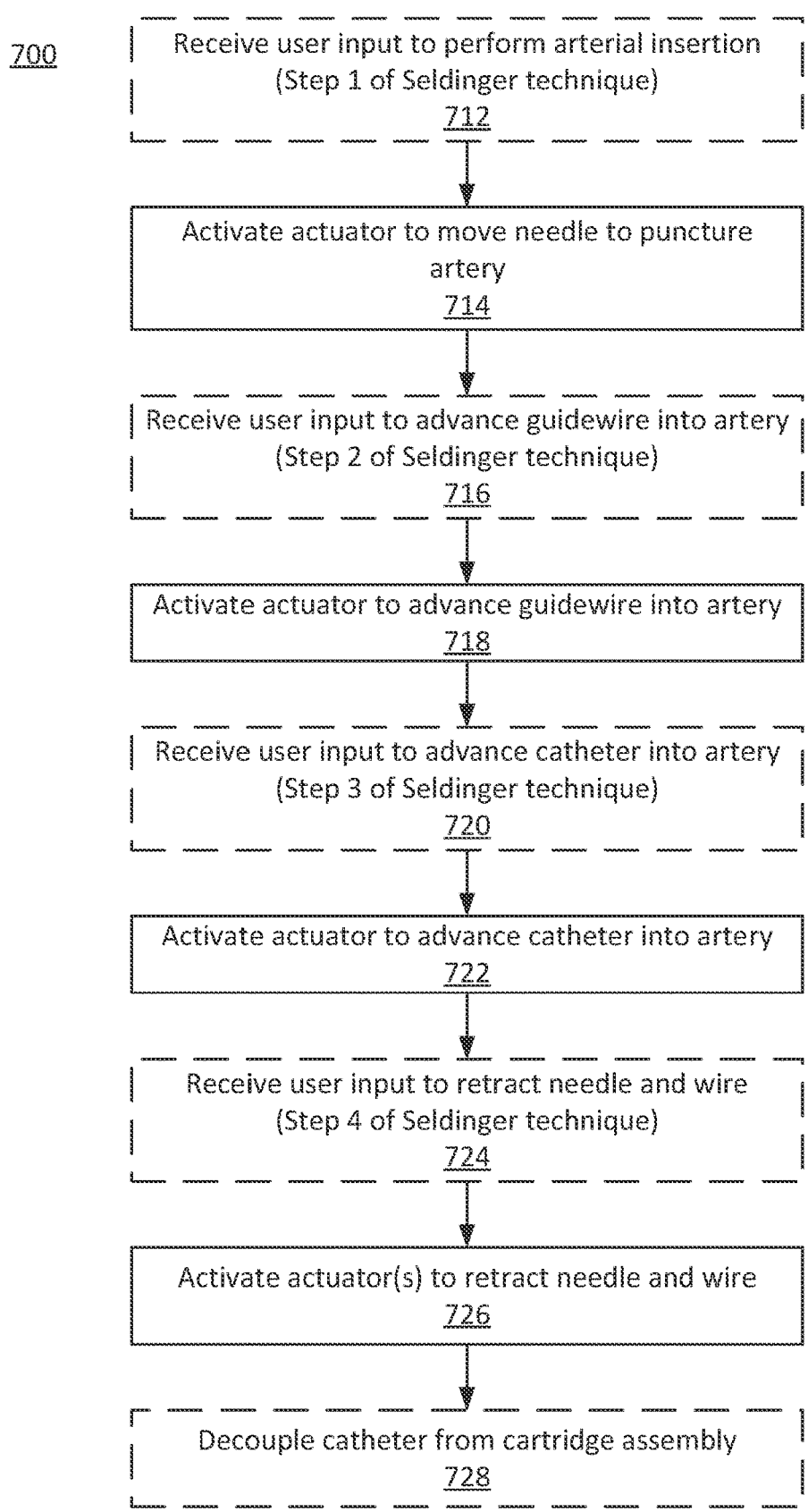
FIG. 7 is a flow diagram illustrating a method of using a vascular access system to perform the Seldinger technique, in accordance with some embodiments.

FIG. 7 is a flow diagram illustrating a method 700 of gaining vascular access, for example, by performing the Seldinger technique (e.g., using system 100 in FIG. 1 or any of the other systems and/or components described herein), in accordance with some embodiments. At 712, the method 700 can include receiving user input to access a blood vessel. For instance, the user input can include instructions to perform arterial insertion. In some embodiments, a user can transmit an input to perform the arterial insertion to a robotic system (e.g., robotic system 102 in FIG. 1, robotic system 202 in FIG. 2, etc.) via an I/O device (e.g., I/O device(s) 104 in FIG. 1 or user control 404a in FIG. 4) that is communicably coupled to the robotic system. The robotic system can be controlled based on the input so as to position and/or orient the robotic system to perform the arterial insertion. For example, the base (e.g., base 203 in FIG. 2), the manipulation device (e.g., manipulation device 230 in FIG. 2), and/or the cartridge assembly (e.g., cartridge assembly 240 in FIG. 2) can be positioned and/or oriented based on the user input such that the cartridge assembly is at a specific distance and/or orientation from the desired artery.

At 714, the method 700 can include activating an actuator (e.g., needle actuator 534*b* in FIG. 5) to move a needle to puncture the artery. In some embodiments, the needle can be included in the cartridge assembly. The needle can be coupled to a needle guide (e.g., a portion of the needle actuator 534*b* included in the cartridge assembly) that can include a coupling element such as a puck comprising a magnetic portion (e.g., an embedded steel disk). A recessed portion in the manipulation device can be configured to fit the needle guide along with the needle. The cartridge assembly can be attached to the manipulation device via a magnet (e.g., permanent electromagnet) included in a carriage block (e.g., coupling mechanism 538 in FIG. 5) that completes a magnetic circuit with the magnetic portion.

In response to the input from the user (e.g., via an I/O device) to perform arterial insertion, a linear actuator (e.g., portion of the needle actuator 534*b* included in the manipulation device) to actuate the needle can be activated. The linear actuator can move along a linear axis. This in turn can cause the needle guide along with the needle to move along the linear axis. Accordingly, the needle can be moved and positioned so as to puncture the desired artery. In some embodiments, performing the arterial insertion can include aligning a tip of the needle to a catheter tip. As the tip of the needle is advanced into the desired artery, the tip of the needle may remain in the same longitudinal plane. However, the transverse plane of the tip of the needle may change as the needle advances.

In some embodiments, the user can visualize the movement of the needle using visual aid (e.g., ultrasound images) captured by an imaging device (e.g., imaging device 536 in FIG. 5). For example, the absolute position of the tip of the needle can be determined in order to determine the transverse plane that is to be captured through the visual aid. The visual aid can provide the user with information on the movement of the needle. In some embodiments, the user can visualize the movement of the robotic arm, manipulation device, and/or the cartridge assembly as the needle is being actuated using sensor data obtained from sensor(s) (e.g., sensor(s) 106 in FIG. 1). The user can modify the input to perform arterial insertion based on the visual aid and/or the sensor data.

At 716, the method 700 can include receiving user input (e.g., via an I/O device) to advance the guidewire into the artery. Once the artery has been punctured and the needle positioned in the artery, the user can transmit instructions (e.g., similar to step 712) to advance the guidewire into the artery.

At 718, in response to the instructions at 716, the method 700 can include activating an actuator (e.g., guidewire actuator 534*c* in FIG. 5) to advance the guidewire into the artery. Similar to the needle, the guidewire can be included in the cartridge assembly. The guidewire coupled to a guidewire guide (e.g., a portion of the guidewire actuator 534*c* included in the cartridge assembly) can be attached to the manipulation device via a permanent electromagnet in a carriage block. Additionally and/or alternatively, a recessed portion in the manipulation device can be configured to fit the guidewire guide along with the guidewire.

In response to the user input (e.g., via an I/O device) to advance the guidewire, a linear actuator (e.g., portion of the guidewire actuator 534*c* included in the manipulation device) to actuate the guidewire can be activated. The linear actuator can move along a linear axis. This in turn can cause the guidewire guide along with the guidewire to move along the linear axis. Accordingly, the guidewire can be advanced to the desired location in the artery. The needle and the catheter can be held stationary as the guidewire is advanced into the artery. In some embodiments, the user can visualize the movement of the guidewire using visual aid captured by the imaging device. The transverse plane that is to be captured via the visual aid can be updated based on the absolute position of a tip of the guidewire. In some embodiments, the user can visualize the movement of the robotic arm, manipulation device, and/or the cartridge assembly as the guidewire is being advanced using sensor data obtained from the sensor(s). The user can modify the input to advance the guidewire based on the visual aid and/or the sensor data.

At 720, the method 700 can include receiving user input (e.g., via an I/O device) to advance the catheter into the artery. In some embodiments, the user can transmit instructions (e.g., similar to step 712) to advance the catheter into the artery.

At 722, in response to the instructions at 720, the method 700 can include activating an actuator (e.g., catheter actuator 534*a* in FIG. 5) to advance the catheter into the artery. Similar to the needle, the catheter can be included in the cartridge assembly. The catheter coupled to a catheter guide (e.g., a portion of the catheter actuator 534*a* included in the cartridge assembly) can be attached to the manipulation device via a permanent electromagnet in a carriage block. Additionally and/or alternatively, a recessed portion in the manipulation device can be configured to fit the catheter guide along with the catheter.

In response to the user input (e.g., via an I/O device) to advance the catheter, a linear actuator (e.g., portion of the catheter actuator 534*a* included in the manipulation device) to actuate the catheter can be activated. The linear actuator can move along a linear axis. This in turn can cause the catheter guide along with the catheter to move along the linear axis. Accordingly, the catheter can be advanced to the desired location in the artery. In some embodiments, the user can visualize the movement of the catheter using visual aid captured by the imaging device. In some embodiments, the user can visualize the movement of the robotic arm, manipulation device, and/or the cartridge assembly as the catheter is being advanced using sensor data obtained from the sensor(s). The user can modify the input to advance the catheter based on the visual aid and/or the sensor data.

At 724, the method 700 can include receiving user input (e.g., via an I/O device) to retract the needle and the guidewire. At 726, in response to the instructions at 724, the method 700 can include activating the needle actuator and the guidewire actuator to retract the needle and the guidewire. For example, the linear actuators to actuate the needle and the guidewire respectively can be activated such that the linear actuators retract back into the manipulation device along the linear axis. Therefore, the needle guide along with the needle and the guidewire guide along with the guidewire retract into the cartridge assembly along the linear axis (since the needle guide along with the needle and the guidewire guide along with the guidewire are attached to their respective linear actuators). In some embodiments, the user can visualize the movement of the retraction of the needle and the guidewire using visual aid captured by the imaging device. In some embodiments, the user can visualize the movement of the robotic arm, manipulation device, and/or the cartridge assembly as the needle and/or the guidewire is being retracted using sensor data obtained from the sensor(s). The user can modify the input to retract the needle and/or the guidewire based on the visual aid and/or the sensor data.

At 728, the method 700 can include decoupling the catheter from the cartridge assembly. In some embodiments, decoupling the catheter can include decoupling the catheter guide along with the catheter from the cartridge assembly. For example, as discussed above, the catheter guide can be attached to a linear actuator via a permanent electromagnet in the manipulation device. The catheter guide can include a puck comprising a magnetic portion (e.g., an embedded steel disk). The magnetic portion can act as an armature to close the magnetic circuit in the magnet (e.g., permanent electromagnet). Accordingly, the puck can be attached to the magnet in power-on and power-off scenarios. In order to release the puck, current can be applied to the magnet. In this manner, by energizing the magnet, the puck and thereby the catheter guide can be released from the cartridge assembly. Alternatively, the catheter can be detached from the catheter guide without releasing the catheter guide from the cartridge assembly. For example, the user can manually decouple the catheter from the catheter guide without decoupling the catheter guide from the cartridge assembly.

Although in FIG. 7, the sequence of steps to gain access to a blood vessel is described as activating an actuator to advance the needle followed by activating an actuator to advance the guidewire and subsequently activating an actuator to advance the catheter, it should be readily understood that the sequence of steps to gain access to a blood vessel using the system and methods described herein can be performed in any suitable permutations and combinations. For example, in some embodiments, one or more actuators can be activated to advance the needle, the catheter, and the guidewire simultaneously. Once the needle punctures the desired blood vessel (e.g., artery), the guidewire can be advanced distal to the needle to a desired position in the blood vessel. The catheter can then be advanced over the guidewire to the desired position in the blood vessel. In some embodiments, after advancing the guidewire but before advancing the catheter to the desired position in the blood vessel, the needle can be retracted slightly (e.g., moved proximal by a small distance) so that advancing the catheter may be atraumatic to the subject. Alternatively, one or more actuators can be activated to align the needle tip and the distal end of the catheter. The needle and the catheter can be advanced simultaneously to a desired blood vessel. Once the needle punctures the desired blood vessel, the guidewire can be advanced through the puncture to a desired position in the blood vessel. The catheter can then be further advanced to the desired position in the blood vessel. As discussed above, these are a few examples to illustrate various permutations and combinations for accessing a blood vessel using the systems and methods described herein.

In some embodiments, if the size of the blood vessel is large (e.g., central vein), a second catheter can be advanced over the first catheter in order to perform the medical procedure. Put differently, one or more actuators can advance the needle, the guidewire, and the catheter to a desired position in the desired blood vessel. Then, the needle and the guidewire can be retracted from the blood vessel. Another guidewire can be advanced (e.g., manually and/or autonomously) through the catheter already positioned in the desired location. A second catheter that is bigger in size than the already positioned catheter can be advanced through the guidewire. In this manner, the second larger catheter can be positioned through the first catheter in order to perform the medical procedure. In some embodiments, one or more dilators can be used before positioning either the first catheter (e.g., catheter advanced using actuator(s) in the manipulation device and/or cartridge assembly) and/or the second catheter (e.g., catheter that is larger than the first catheter and is advanced through the first catheter) during the medical procedure.

In some embodiments, method 700 as described herein can be performed autonomously and/or semi-autonomously. Accordingly, one or more steps of receiving user input (e.g., 712, 716, 720, 724) can be optional, and systems and devices described herein can be configured to automatically proceed from actuating one component to the next based on confirmation that a first step has been completed. Such confirmation can be determined via sensor data (e.g., via sensor(s) 106) and/or imaging data (e.g., via imaging device 536). In some embodiments, one or more steps may be performed without user input while other steps may be performed with user input.

Figure 8:
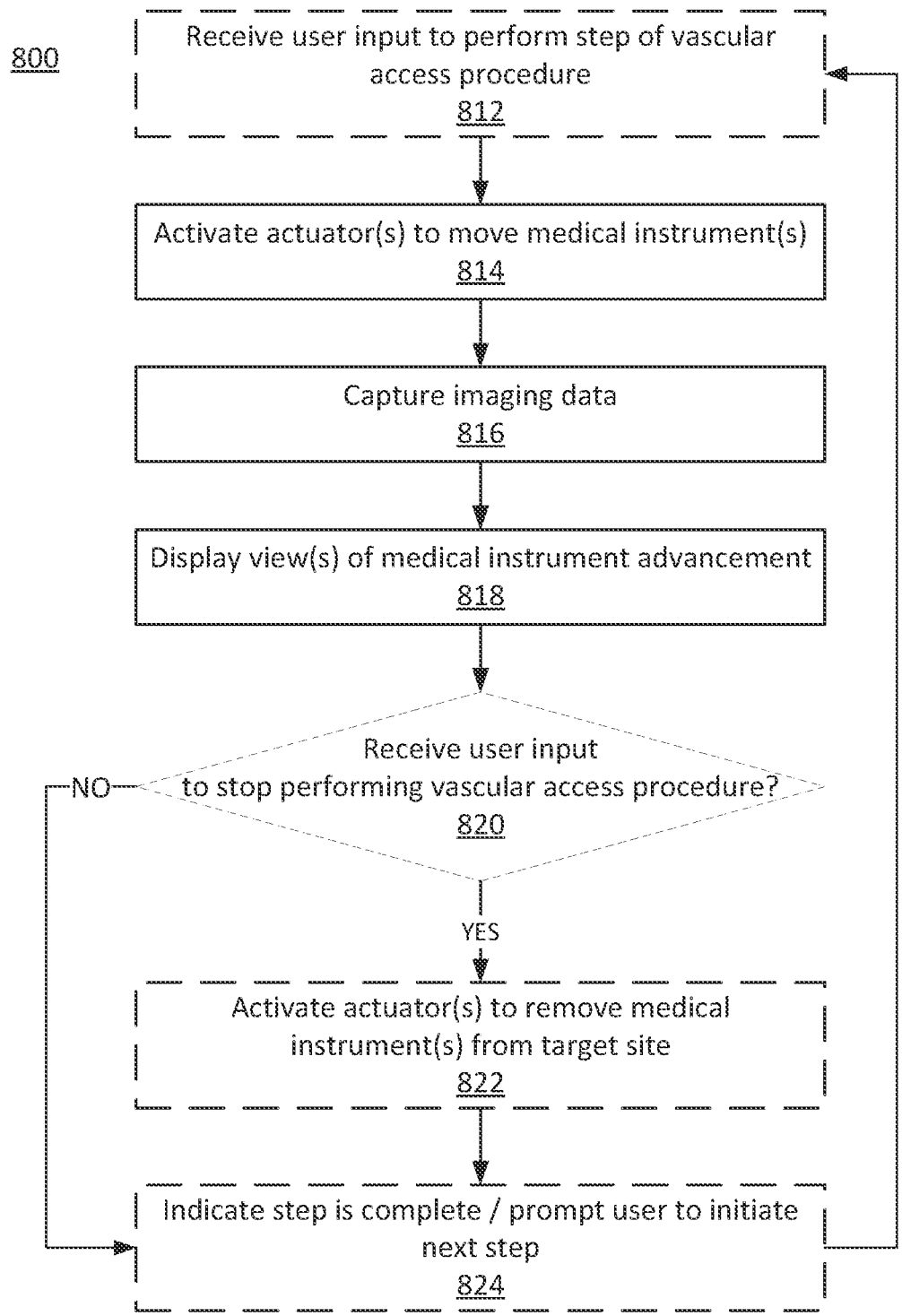
FIG. 8 is a flow diagram illustrating a method of using visual aid and/or sensor data to perform a vascular access procedure, in accordance with some embodiments.

FIG. 8 is a flow diagram illustrating a method 800 of using visual aid and/or sensor data to perform a medical procedure (e.g., using system 100 in FIG. 1), in accordance with some embodiments. At 812, the method 800 can include receiving user input to perform a step of the medical procedure (e.g., vascular access procedure). For example, the user input can include instructions to perform arterial insertion (e.g., step 712 in FIG. 7), advance a guidewire into a blood vessel (e.g., step 716 in FIG. 7), advance a catheter into a blood vessel (e.g., step 720 in FIG. 7), and/or retract a needle and the guidewire from the blood vessel (e.g., step 724 in FIG. 7).

At 814, the method 800 can include activating actuators to move medical instruments based on the user input. For example, activating actuators can include activating actuators within a robotic system (e.g., robotic system 202 in FIG. 2 and/or other robotic systems described herein) to move transport elements (e.g., transport element 414 in FIG. 4) and/or vertical adjustment elements (e.g., vertical adjustment element(s) 409 in FIG. 4) included in the robotic system based on the user input. This in turn can cause a robotic arm (e.g., robotic arm 220 in FIG. 2 and/or other robotic arms described herein), a manipulation device (e.g., manipulation device 230 in FIG. 2 and/or other manipulation devices described herein), and/or a cartridge assembly (e.g., cartridge assembly 240 in FIG. 2 and/or other cartridge assemblies described herein) to be positioned at a desired location from a target site (e.g., subject's body part such as arm). In some embodiments, activating actuators can include activating device actuators (e.g., device actuator(s) 534 in FIG. 5) to advance (e.g., steps 714, 718, and 722 in FIG. 7) and/or retract (e.g., step 726 in FIG. 7) the needle, the catheter, and/or the guidewire into/from a blood vessel based on the user input.

At 816, the method 800 can include capturing visual aid and/or sensor data as the step of the vascular access procedure is being performed. For example, the manipulation device can include an imaging device (e.g., imaging device 536 in FIG. 5) to capture visual aid (e.g., ultrasound images) of the needle, the catheter, and/or the guidewire (collectively device(s) 544 in FIG. 5) as the device(s) are being advanced into and/or retracted from the blood vessel. In some embodiments, the robotic system can be communicably coupled to a sensor (e.g., sensor(s) 106 in FIG. 1) such as a camera to capture images of the robotic system, the manipulation device, and/or the cartridge assembly as the step of the vascular access procedure is being performed.

At 818, the visual aid and/or the sensor data can be displayed on an I/O device (e.g., I/O device(s) 104 in FIG. 1 or user control 404a in FIG. 4). For example, ultrasound images and/or images from cameras can be displayed on a display. At 822, if a user input to stop performing the step of the medical procedure is received (e.g., at step 820), the method 800 can include activating the actuators to remove the medical instruments from the target site. For example, the needle, the catheter, and/or the guidewire can be retracted from the blood vessel by activating the device actuators. Additionally or alternatively, the robotic system, the manipulation device and/or the cartridge assembly can be moved away from the subject by activating the actuators coupled to the transport elements and/or the vertical adjustment elements. In some embodiments, the cartridge assembly can be detached from the manipulation device.

At 824, the method 800 can include indicating to the user that the step of the vascular access procedure is complete. For example, the display can output visual, audio, and/or haptic outputs to represent that the step of the medical procedure is complete. In some embodiments, the display can also prompt the user to initiate the next step thereby repeating the steps of method 800. If the user input to stop performing the step of the medical procedure is not received at step 820, the method 800 can include at 824 indicating to the user that the step of the vascular access procedure is complete and prompting the user to initiate the next step of the vascular access procedure.

Examples

Figure 9A:
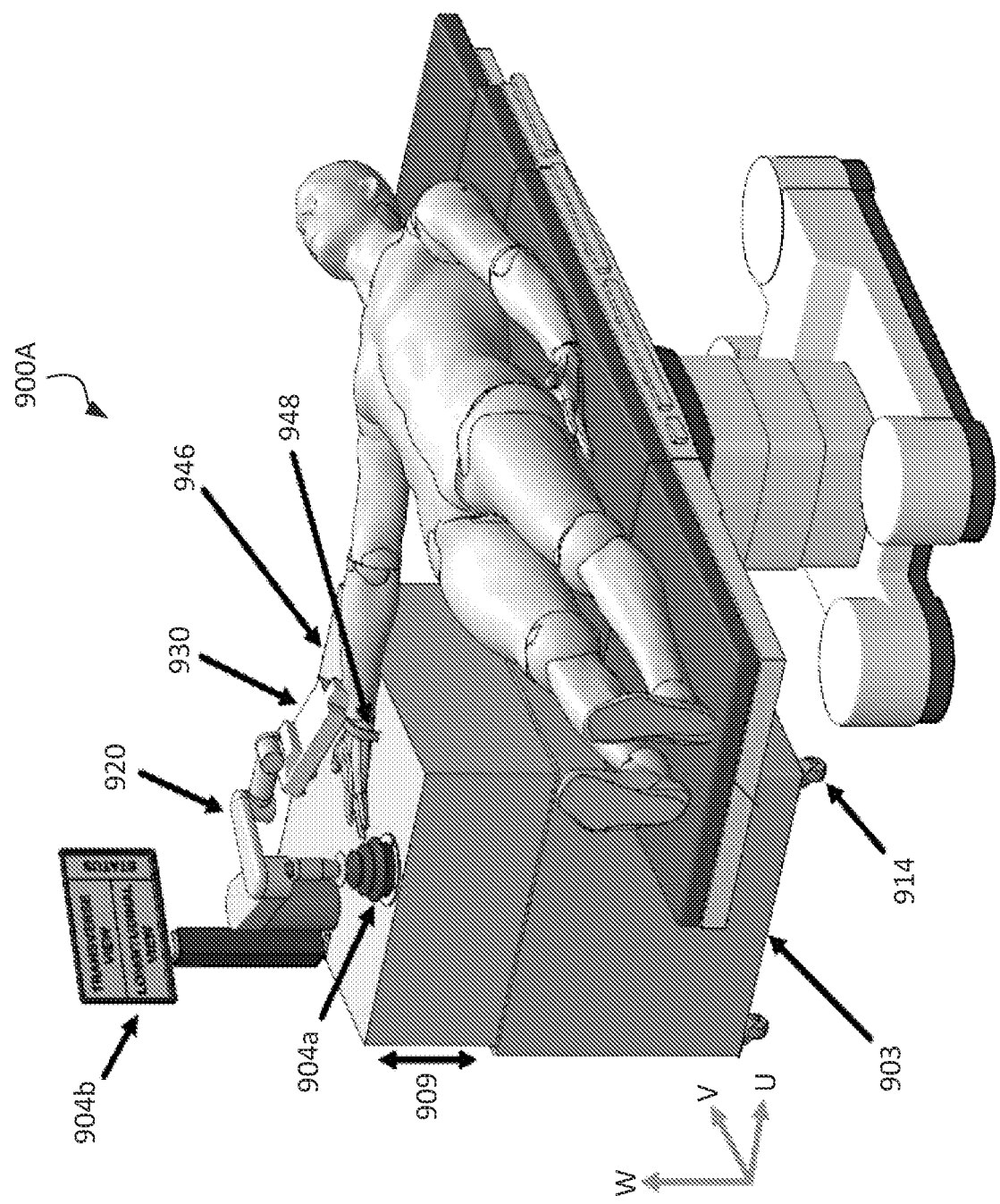
FIG. 9A illustrates a vascular access system, in accordance with some embodiments.

FIG. 9A illustrates a vascular access system 900A (e.g., structurally and/or functionally similar to system 100 in FIG. 1), in accordance with some embodiments. The vascular system can include a robotic system that can include a base 903 (e.g., structurally and/or functionally similar to base 203 in FIG. 2), robotic arm 920 (e.g., structurally and/or functionally similar to robotic arm 220 in FIG. 2), and manipulation device 930 (e.g., structurally and/or functionally similar to manipulation device 230 in FIG. 2).

The base 903 can be a movable base. For example, the base 903 can include transport elements 914 (e.g., structurally and/or functionally similar to transport elements 414 in FIG. 4). In some embodiments, the transport elements 914 can be swivel casters with lockable wheels. The swivel casters can provide the base 903 with three degrees of freedom. For example, the swivel casters can provide translations along the U coordinate axis and the V coordinate axis shown in FIG. 9A. Additionally, the swivel casters can provide rotation along the W coordinate axis shown in FIG. 9B. The planar and rotational movement can enable the base 903 to be positioned relative to a subject's (e.g., patient on whom the medical procedure is to be performed) arm. In some embodiments, a locking mechanism (e.g., locking mechanism 412 in FIG. 4) for the transport elements 914 can lock a position of the base 903 during the medical procedure. For example, in some embodiments, locks may be engaged automatically during a step of the medical procedure such as upon the base being positioned at an appropriate position relative to the arm of a patient on whom the medical procedure is to be performed.

In some embodiments, the base 903 can include vertical adjustment element(s) 909 (e.g., structurally and/or functionally similar to vertical adjustment element(s) 409 in FIG. 4) which can provide a fourth degree of freedom to the base 903. The vertical adjustment element(s) can raise and/or drop the base vertically, thereby providing the base 903 with a fourth degree of freedom. In some embodiments, the vertical adjustment element(s) 909 can lift a top surface 946 of the base 903 to position the robotic arm 920 at an appropriate height with respect to the patient on whom the medical procedure is to be performed. In some embodiments, the vertical adjustment element(s) 909 can be motorized. For example, the vertical adjustment element(s) 909 can include a ball screw actuator. A fail-safe brake can hold the position of the top surface 946 of the base 903. Linear rails with recirculating balls can constraint the movement of the base 903.

In some embodiments, the top surface 946 of the base 903 can be attached to, integrated with, and/or otherwise coupled to one or more I/O device(s). For example, a display 904b (e.g., structurally and/or functionally similar to display 404b in FIG. 4) can be mechanically coupled to the top surface 946 of the base via a display support. The display 904b can provide visual aid and/or visual feedback including longitudinal and traverse ultrasound views of a blood vessel of the subject. In some embodiments, the display 904b can provide state and status information on the task being performed during the medical procedure. Some examples of state information can include the state of the needle actuator, guidewire actuator, and/or catheter actuator during each step of the medical procedure as seen in Table 1.

TABLE 1

| Medical procedure Step | Description | Guidewire Actuator (motor) | Needle Actuator (motor) | Catheter Actuator (motor) |
|---|---|---|---|---|
| 1 | Insertion into blood vessel | Dynamic | Dynamic | Dynamic |
| 2 | Advance guidewire into the blood vessel | Dynamic | Static | Static |
| 3 | Advance catheter into the blood vessel | Static | Static | Dynamic |
| 4 | Retract needle and guidewire | Dynamic | Dynamic | Static |

In some embodiments, a user control 904a (e.g., structurally and/or functionally similar to user control 404a in FIG. 4) can be attached to and/or integrated with the top surface 946 of the base 903. For example, a joystick 904a as shown in FIG. 9A can be used to control the robotic system. For instance, the joystick 904a may control the three degrees of freedom (e.g., translation and rotation) and/or four degrees of freedom (e.g., translation, rotation, and/or vertical drop or raise) of the base 903. The joystick 904a can be any suitable type of joystick such as digital joysticks, paddle joysticks, analog joysticks, Pc analog joysticks, and/or the like.

Additionally or alternatively, a handheld pendant (e.g., handheld pendant 1104a in FIG. 11A further described below) can be used to control the robotic system. In addition to controlling the three and/or four degrees of freedom of the base 903, the handheld pendant can additionally control the needle actuator, guidewire actuator, and/or catheter actuator prior to, during, and/or after each step of the Seldinger technique based on the states shown in Table 1. For example, the handheld pendant can change the state of the needle actuator and the catheter actuator from dynamic to static after arterial insertion but before advancing the guidewire into the artery.

In some embodiments, the top surface 946 of the base 903 can be attached to, integrated with, and/or otherwise coupled to the robotic arm 920. In some embodiments, the top surface 946 of the base 903 can include an arm restraint 948 to constrict the arm of a subject during the medical procedure. The arm restraint 948 can be an elastic band that can restraint an arm of any size.

Figure 9B:
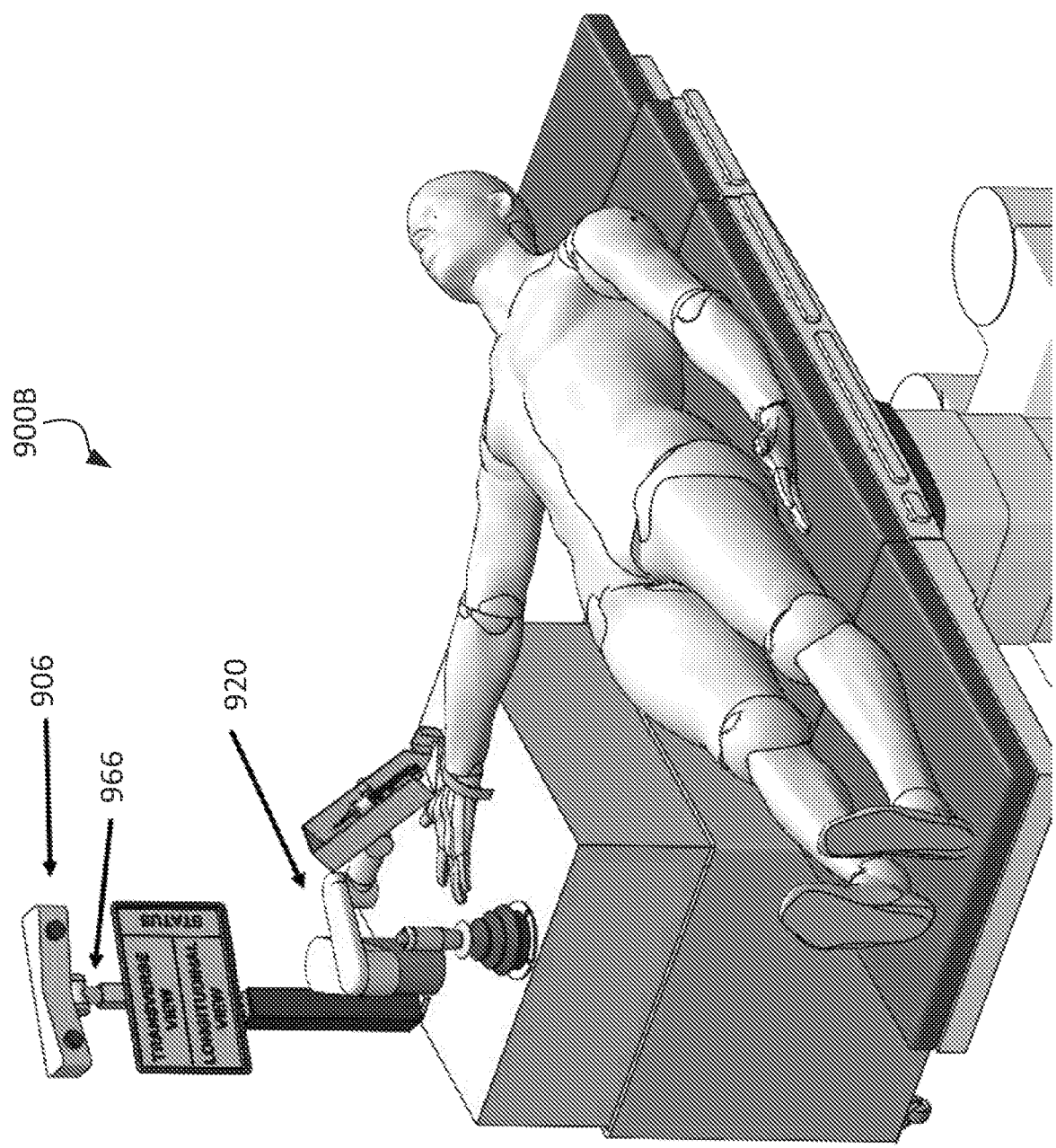
FIG. 9B illustrates a vascular access system, in accordance with some embodiments.

FIG. 9B illustrates a vascular access system 900B (e.g., structurally and/or functionally similar to system 100 in FIG. 1), in accordance with some embodiments. In addition to the components in system 900A, the system 900B additionally includes a sensor 906 (e.g., structurally and/or functionally similar to sensor 106 in FIG. 1). The sensor 906 can be coupled to a top surface of the base 903. The sensor 906 can be an image sensor and/or an image capturing device that can capture image data of at least a part of the robotic system, the manipulation data, and/or part of the subject as the robotic system performs the medical procedure on the subject. For example, the sensor 906 can be a three-dimensional vision system such as a stereo camera and/or a camera array. The sensor 906 can be mounted on a pan/tilt mechanism 966.

Figure 10:
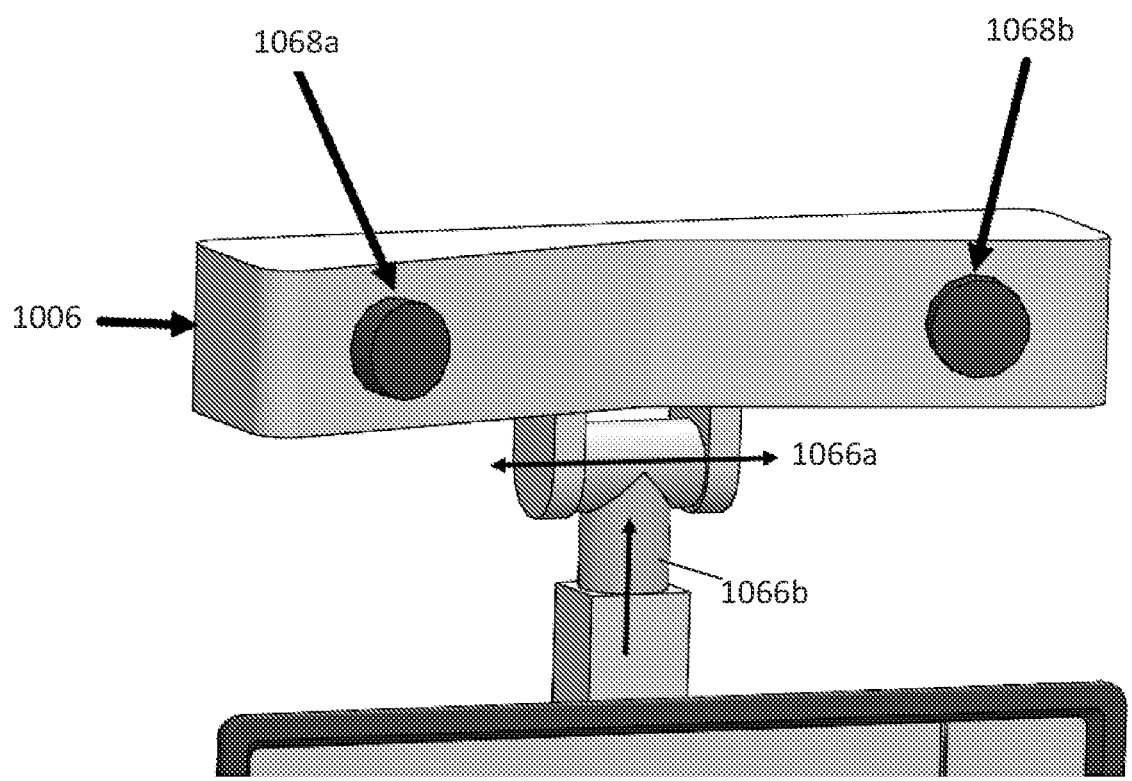
FIG. 10 illustrates an example stereo camera array to capture image data, in accordance with some embodiments.

FIG. 10 illustrates an example stereo camera array 1006 to capture image data, according to some embodiments. The stereo camera array 1006 can include one or more individual image sensors such as for example, right eye camera 1068a and left eye camera 1068b. The right eye camera 1068a and the left eye camera 1068b can capture images of the environment (e.g., at least a part of the robotic system, the manipulation data, and/or part of the subject as the robotic system performs the medical procedure on the subject). In some embodiments, the stereo camera array 1006 can be mounted on a pan/tilt mechanism including a tilt axis of rotation 1066a and a pan axis of rotation 1066b. The stereo camera 1006a can be tilted as desired along the tilt axis of rotation 1066a. The stereo camera 1006 can be panned and/or swiveled along the pan axis of rotation 1066b. In some embodiments, the pan/tilt mechanism and thereby the stereo camera array 1006 can be controlled by a user proximate to the stereo camera array 1006. Alternatively, the pan/tilt mechanism and thereby the stereo camera array 1006 can be controlled by a user remotely.

Referring back to FIG. 9A, the sensor 906 can be configured to be controlled remotely using one or more I/O devices. For instance, the sensor 906 can be controlled by an I/O device that is communicably coupled to the robotic system and/or base 903. A user controlling the sensor 906 can be at a location remote to the system 900B. For example, the sensor 906 can be controlled via an integrated computing device such as computers (e.g., desktops, personal computers, laptops etc.), tablets and e-readers (e.g., Apple iPad®, Samsung Galaxy® Tab, Microsoft Surface®, Amazon Kindle®, etc.), mobile devices and smart phones (e.g., Apple iPhone®, Samsung Galaxy®, Google Pixel®, etc.), etc. that is communicably coupled to the robotic system and/or base 903. In some embodiments, the user control 904a can enable a user in proximity and/or within the vicinity of the system 900B to control the sensor 906.

The sensor 906 can capture a view of the environment for the remote user. Controlling the pan/tilt mechanism can allow the sensor 906 to capture image data from various angles. A user can change the view of the environment as desired by controlling the pan/tilt mechanism. The image data can be used as feedback by the user to control the robotic system in order to perform the medical procedure. In some embodiments, instead of a user controlling the pan/tilt mechanism via an I/O device such as user control 904a, the entire system (e.g., system 900A in FIG. 9A and/or system 900B in FIG. 9B) can be autonomous. For instance, a control unit within the system can control the user control 904a and/or pan/tilt mechanism 966 by taking into account the feedback from image data and/or visual aid (e.g., ultrasound data) as the robotic system performs the medical procedure. Put differently, the system 900A and/or 900B can perform the medical procedure in an autonomous manner.

In some embodiments, the system may include an additional image sensor such as stereo camera (not shown in FIG. 9A and 9B) to enable precise motion of the robotic arm 920 and/or manipulation device 930. The additional image sensor can allow precise targeting and/or access of the vascular portion. For instance, the feedback from the additional image sensor can control the manipulation device 930 and/or the robotic arm 920 in a more precise manner. In some embodiments, proximity sensor(s) may be attached to, coupled to, and/or otherwise mounted on the base 903 to enable previse motion and targeting.

In some embodiments, when the manipulation device 930 contact the skin of the subject, the feedback can be switched from sensor 906 feedback to visual aid from an imaging device such as ultrasound array. For example, a user remote to the system can switch the feedback to ultrasound using an I/O device. As discussed above, in some embodiments, the robotic arm 920 can be motorized. The motorized arm can be controlled (e.g., via an I/O device) to achieve a desired view of a target vascular portion of the subject in the ultrasound array.

In some embodiments, the robotic arm 920 can include sensors to measure force and/or torque in order to perform the medical procedure in a safe manner. For instance, a needle penetration force that is greater than a threshold value can cause damage to the skin, blood vessel, and/or neighboring tissues. Accordingly, measuring the force and/or torque during the medical procedure can ensure the needle penetration force is below the threshold value. For example, for a 25 G needle the maximum penetration force that can be applied by the needle to puncture a forearm vein is 2.5 N. Similarly, maximum penetration force can be determined for 18 G needle, 22 G needle, etc. If the penetration force measured by the sensors exceed the identified maximum penetration value, in some embodiments, the system 900A and/or 900B can be automatically shutdown. For example, in response to the penetration force exceeding the penetration value a control unit (e.g., structurally and/or functionally similar to control unit 405 in FIG. 4) can automatically shutdown the system. In some embodiment, the measured force can also be an indicator of whether or not the needle may have penetrated into a tissue of the subject. For example, when the needle penetrates the tissue, the penetration force can drop. In such scenarios, a user can be notified via a display (e.g., structurally and/or functionally similar to display 404b in FIG. 4) that the needle has penetrated the tissue. In some embodiments, the robotic arm 920 can include collision sensing skin sensors to identify whether the manipulation device 930 is in contact with the skin of the subject prior to performing the medical procedure.

Figure 11A:
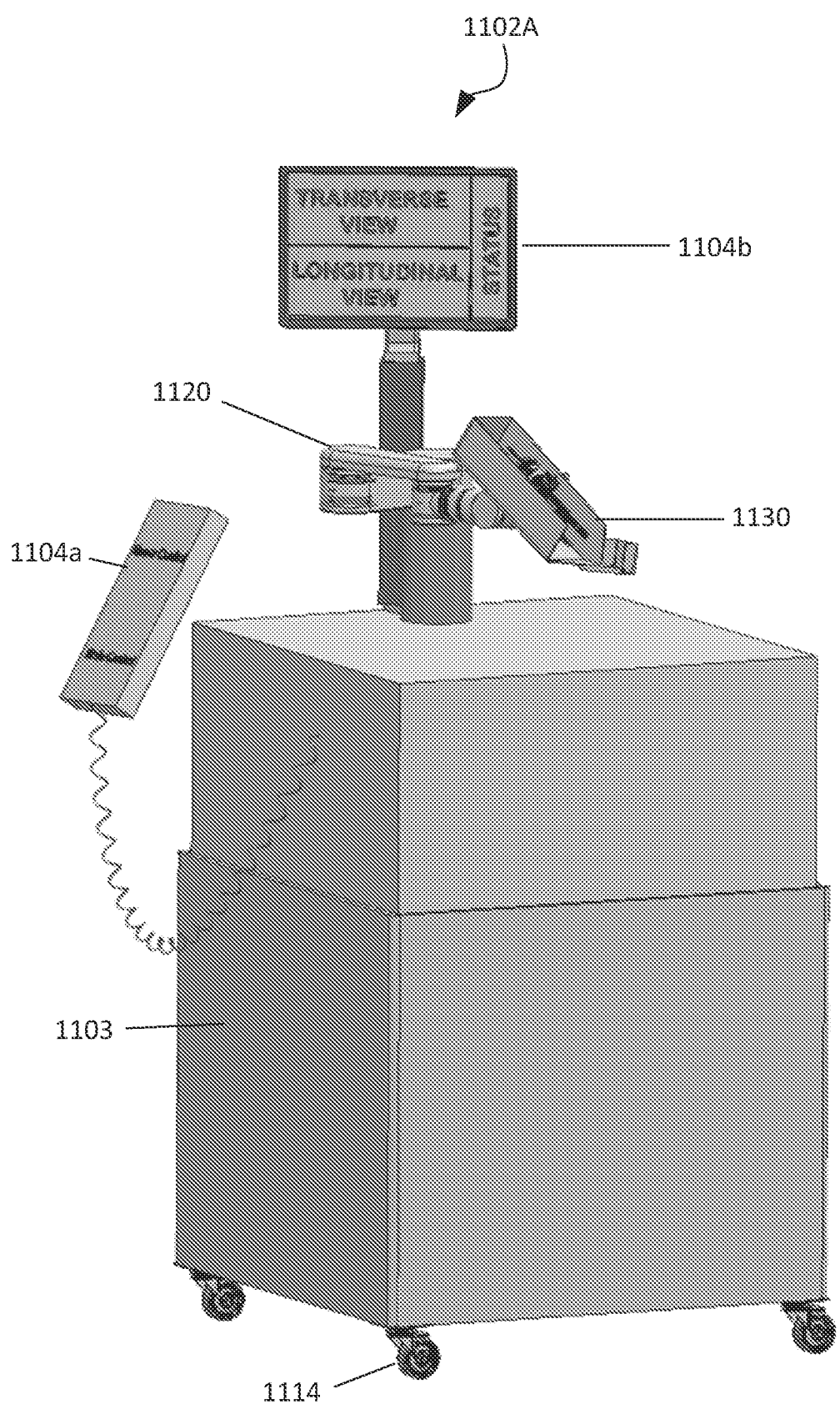
FIG. 11A illustrates an example robotic system, in accordance with some embodiments.

FIG. 11A illustrates a robotic system 1102A (e.g., structurally and/or functionally similar to robotic system 202 in FIG. 2), according to some embodiments. The robotic system 1102A includes a base 1103. A user control 1104a can be attached to, coupled to, and/or integrated with the base 1103. In some embodiments, the user control 1104a can be a handheld pendant. The handheld pendant 1104a can be coupled to the base 1103 via a spiral cord. As discussed above, the handheld pendant 1104a can control the linear motion, rotational motion, and/or vertical movement of the base 1103. Additionally, the handheld pendant 1104a can change the state of the system itself or otherwise one or more components of the system (e.g., needle actuator, catheter actuator, guidewire actuator, etc.) from one step of the medical procedure (e.g., the Seldinger technique) to the next step of the medical procedure. Some non-limiting examples of the state of some components for each step of the Seldinger technique is shown in table 1. For example, the handheld pendant 1104a can be used to change the state of the guidewire actuator from dynamic to static and the state of the catheter actuator from static to dynamic after advancing the guidewire into the artery of a subject but before advancing the catheter into the artery of the subject.

In some embodiments, a display 1104b can be attached to, coupled to, and/or integrated with the base 1103. The display 1104b can display visual aid (e.g., transverse view and longitudinal view of ultrasound images), image data (e.g., images captured from a sensor such as camera), status, and state of the task being performed. In some embodiments, a robotic arm 1120 can be attached to, coupled to, and/or integrated with the base 1103. In some embodiments, the robotic arm 1120 can be motorized. In some embodiments, an end segment of the robotic arm 1120 can be coupled to a manipulation device 1130. The manipulation device can be attached to a cartridge assembly.

Figure 11B:
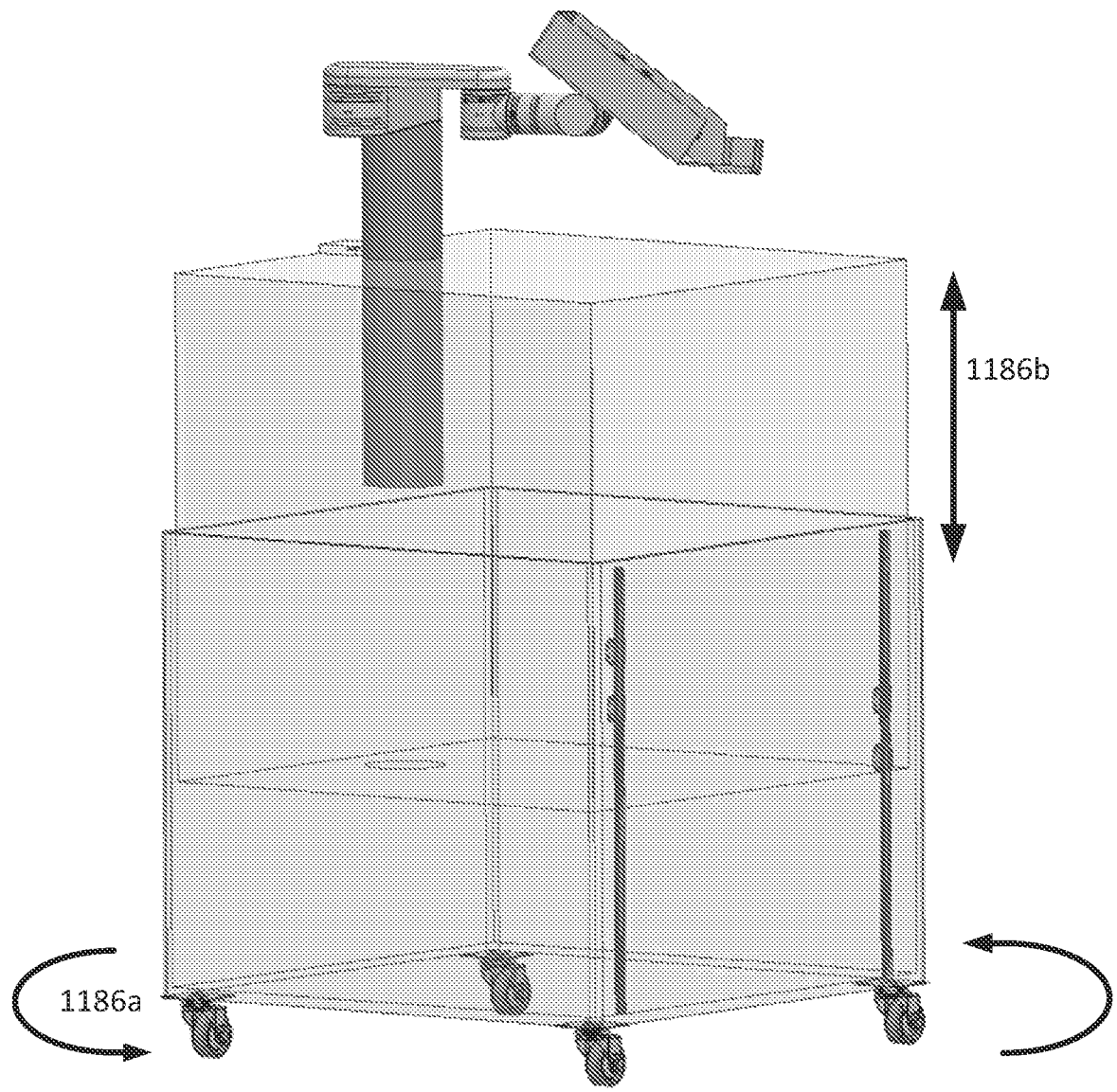
FIG. 11B illustrates rotational motion and vertical movement for a base, in accordance with some embodiments.

In some embodiments, the base 1103 can include transport elements 1114 such as swivel wheels. The transport elements 1114 can provide three degrees of freedom to the base 1103. FIG. 11B illustrates rotational motion and vertical movement for a base 1103, according to some embodiments. The transport elements 1114 can allow the base 1103 to rotate along 1186a. Additionally, the transport elements 1114 can allow the base 1103 to move linearly along two perpendicular axes, thereby providing three degrees of freedom. Additionally, the base 1103 can include vertical elements to raise and/or drop the base 1103 along 1186b. This can provide a fourth degree of freedom to the base.

Figure 12A:
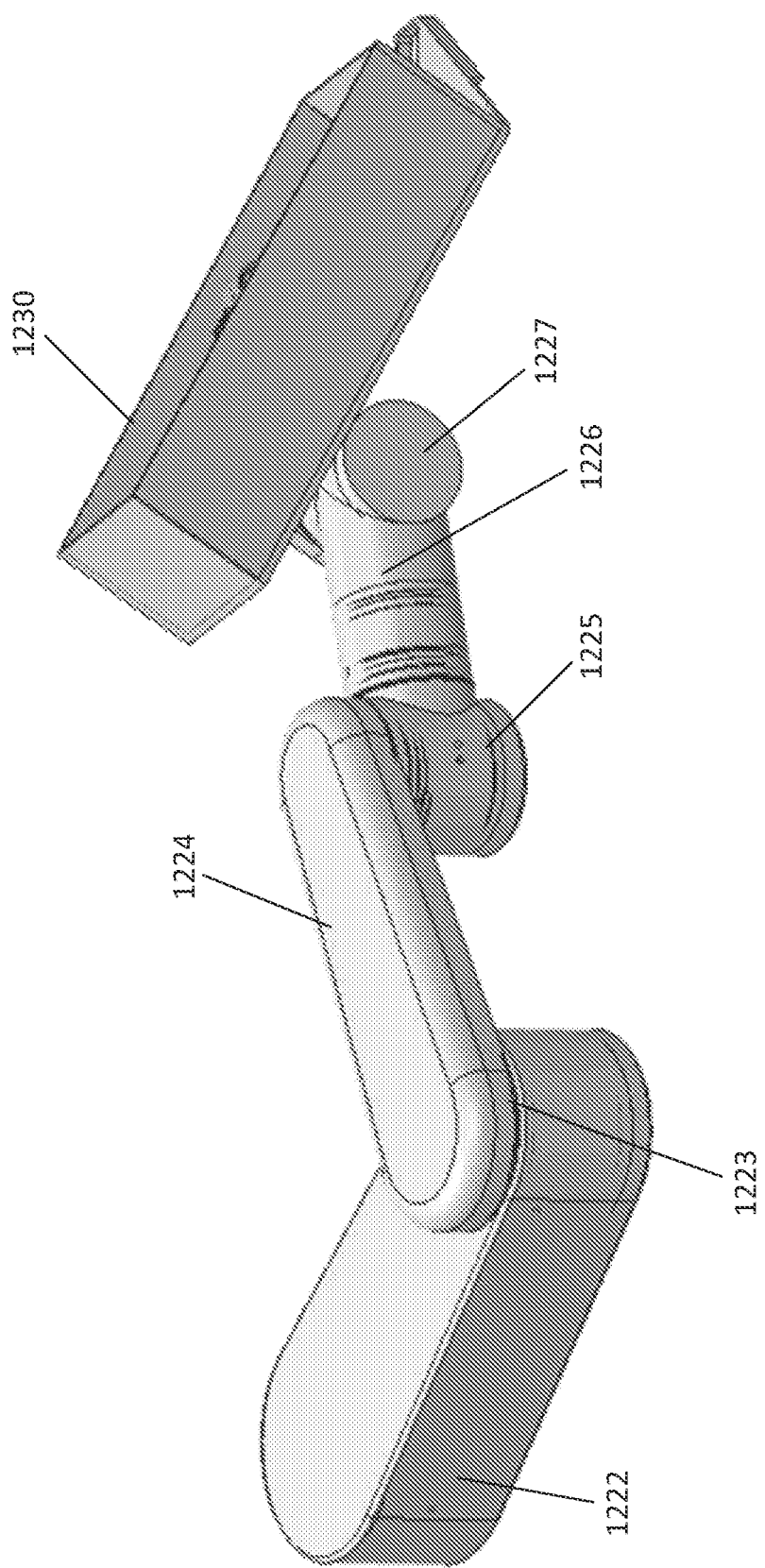
FIGS. 12A-12C illustrates a robotic arm, in accordance with some embodiments.
Figure 12B:
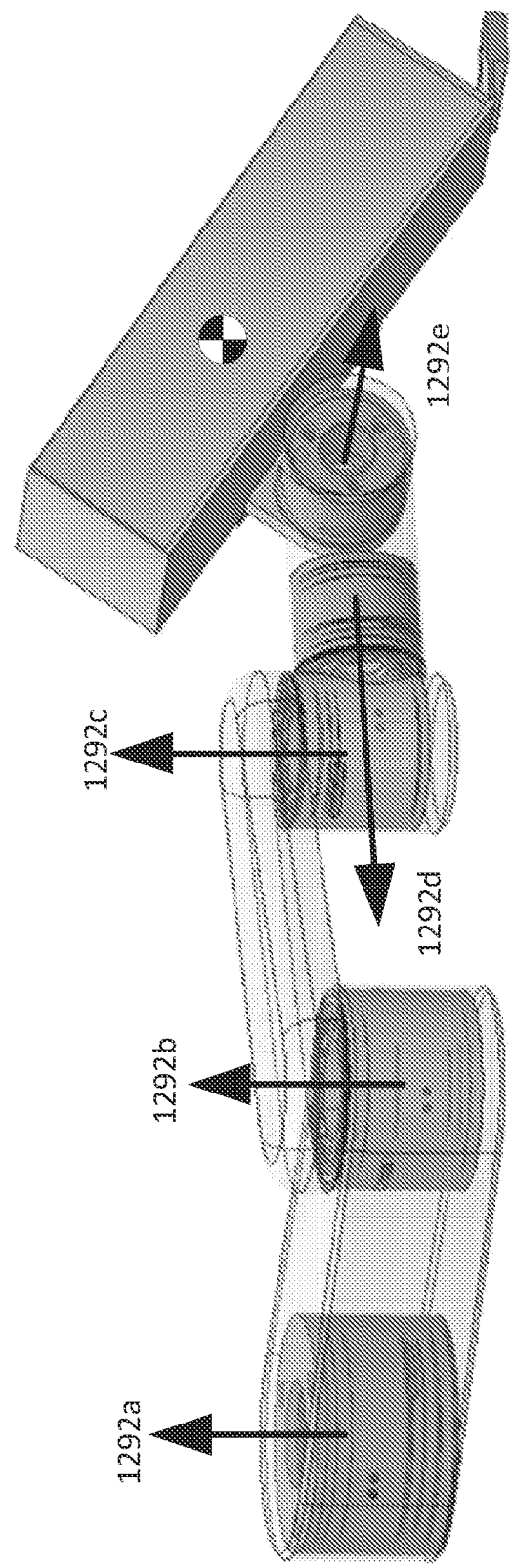
Figure 12C:
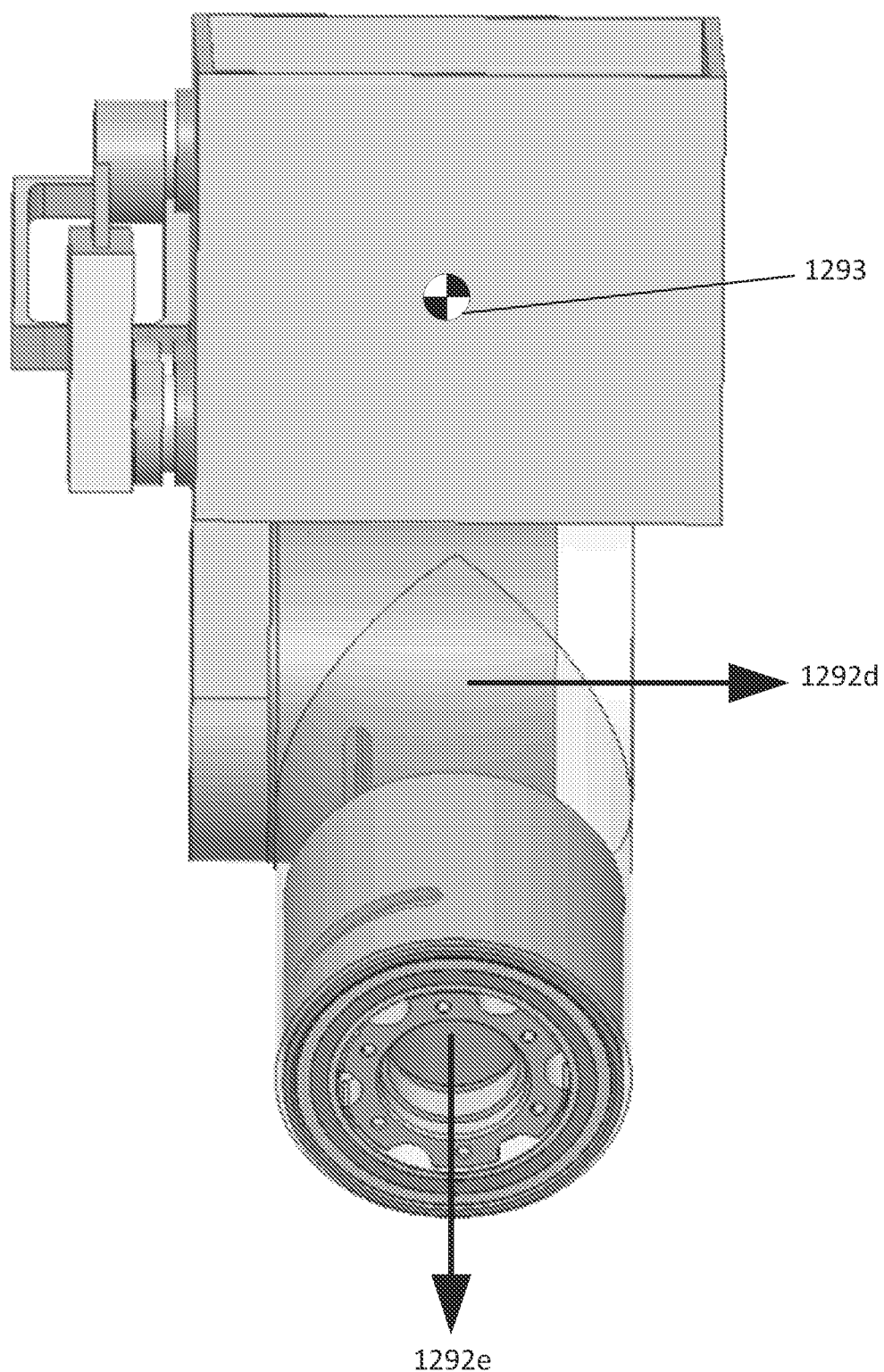

FIGS. 12A-12C illustrates a robotic arm (e.g., structurally and/or functionally similar to robotic arm 220 in FIG. 2 and/or robotic arm 320 in FIG.3), according to some embodiments. As seen in FIG. 12A, the robotic arm can include segment 1222 and segment 1224 coupled together via one or more joints 1223. Segment 1224 and segment 1226 can be coupled together via one or more joints 1225. In some embodiments, manipulation device 1230 (e.g., structurally and/or functionally similar to manipulation device 230 in FIG. 2) and segment 1226 can be coupled together via one or more joints 1227. Alternatively, the manipulation device 1230 can be integrated with segment 1226.

As seen in FIG. 12B, the robotic arm can have three proximal axes (axes not shown in FIG. 12B, 1292a, and 1292b). The first proximal axis (not shown in FIG. 12B) can be along an arm support integrated and/or coupled to the robotic arm that enables vertical translation of the robotic arm along the arm support. The second and third proximal axis can be 1292a and 1292b respectively. The three proximal axes can allow the system to be positioned in the three-dimensional space and can allow translation of the robotic arm along the three-dimensional space.

The robotic arm can have three distal axes (1292c, 1292d, and 1292e). The three distal axes can allow rotation of the robotic arm along the three-dimensional space (e.g., pitch, yaw, and roll). In some embodiments, axes 1292a, 1292b, and 1292c can comprise a planar Selective Compliance Articulating Robot Arm (SCARA) linkage. The selective compliance can refer to the relation of the robotic arm's stiffness in-plane vs. the robotic arm's stiffness out-of-plane. In some embodiments, axes 1292a, 1292b, and 1292c move in the X-Y plane. This can provide advantages such as an intuitive kinematic chain that can be easily understood. Furthermore, movement with the X-Y plane can restrain the motion of the robotic arm to a plane orthogonal to gravity. This in turn can eliminate the need for any counterbalancing or gravity compensation.

In some embodiments, axes 1292c, 1292d, and 1292e effectively comprise a three-axis gimbal capable of orienting the robotic arm about three orthogonal axes of rotation. As seen in FIG. 12C, axis 1292d can be oriented very close to the center of mass 1293 of the robotic arm thereby minimizing gravity torque and the need for a counterbalance. In a similar manner, axis 1292e can also be oriented very close to the center of mass 1293 of the robotic arm thereby minimizing gravity torque and the need for a counterbalance.

In some embodiments, rotational constraint of the robotic arm can be achieved using at least one cross-roller bearing. The cross-roller bearing can be capable of reacting to forces in the three linear degrees of freedom and torques in the two rotational degrees of freedom. Additionally, the cross-roller bearing can be free to rotate in the final rotational degree of freedom. In some embodiments, the joints along the axes 1292a-1292e can include the cross-roller bearings. Additionally, the joints along the axes 1292a-1292e can include failsafe brakes.

Figure 13A:
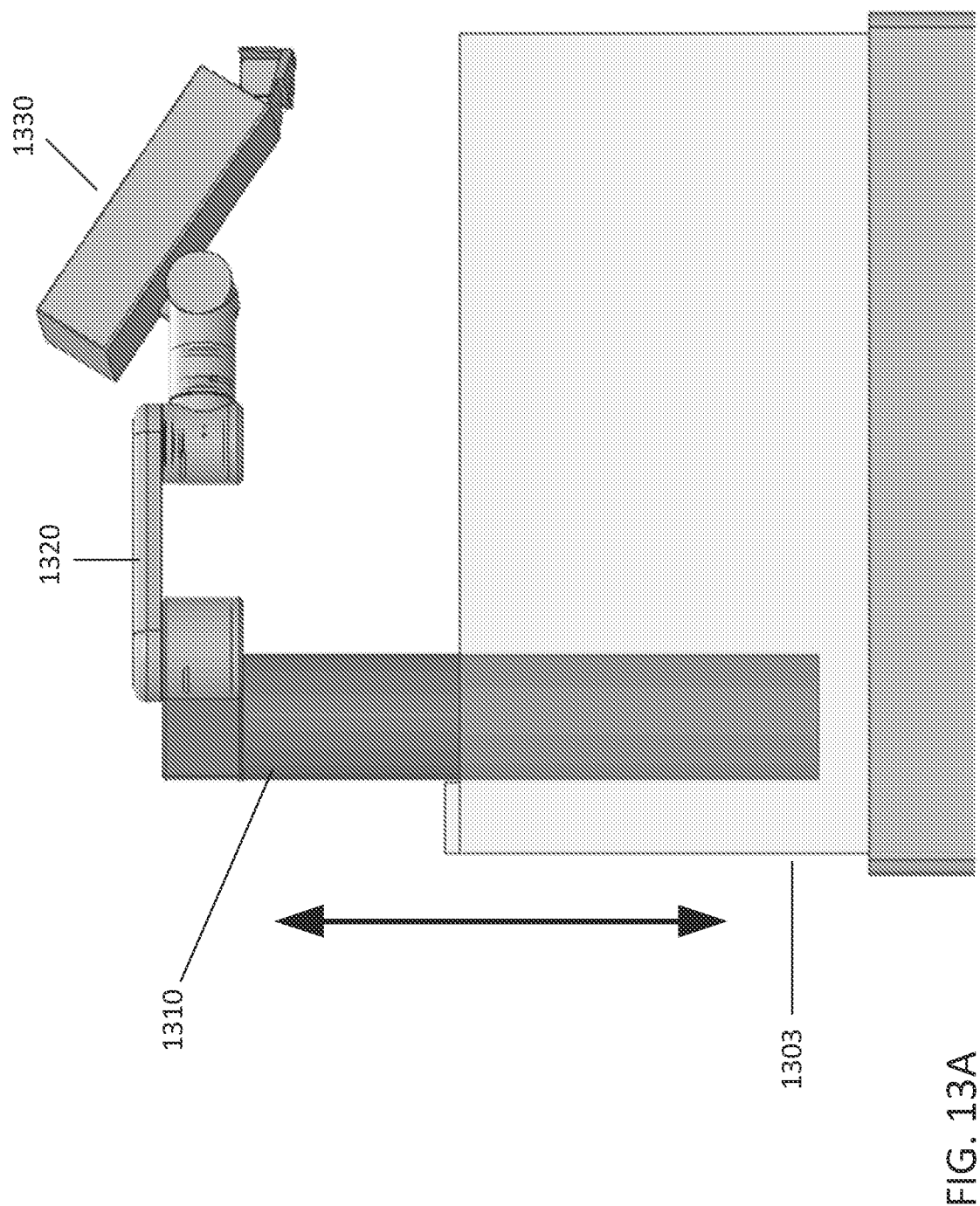
FIG. 13A illustrates a first proximal axis of the robotic arm along arm support that enables vertical translation of the robotic arm along the arm support, in accordance with some embodiments.

FIG. 13A illustrates a first proximal axis of the robotic arm 1320 (e.g., structurally and/or functionally similar to robotic arm 220 in FIG. 2 and/or robotic arm 320 in FIG.3) along arm support 1310 (e.g., structurally and/or functionally similar to arm support 210 in FIG. 2) that enables vertical translation of the robotic arm along the arm support 1310, in accordance with some embodiments. The robotic arm 1320 can be coupled to or otherwise attached to manipulation device 1330 (e.g., structurally and/or functionally similar to manipulation device 230 in FIG. 2).

Figure 13B:
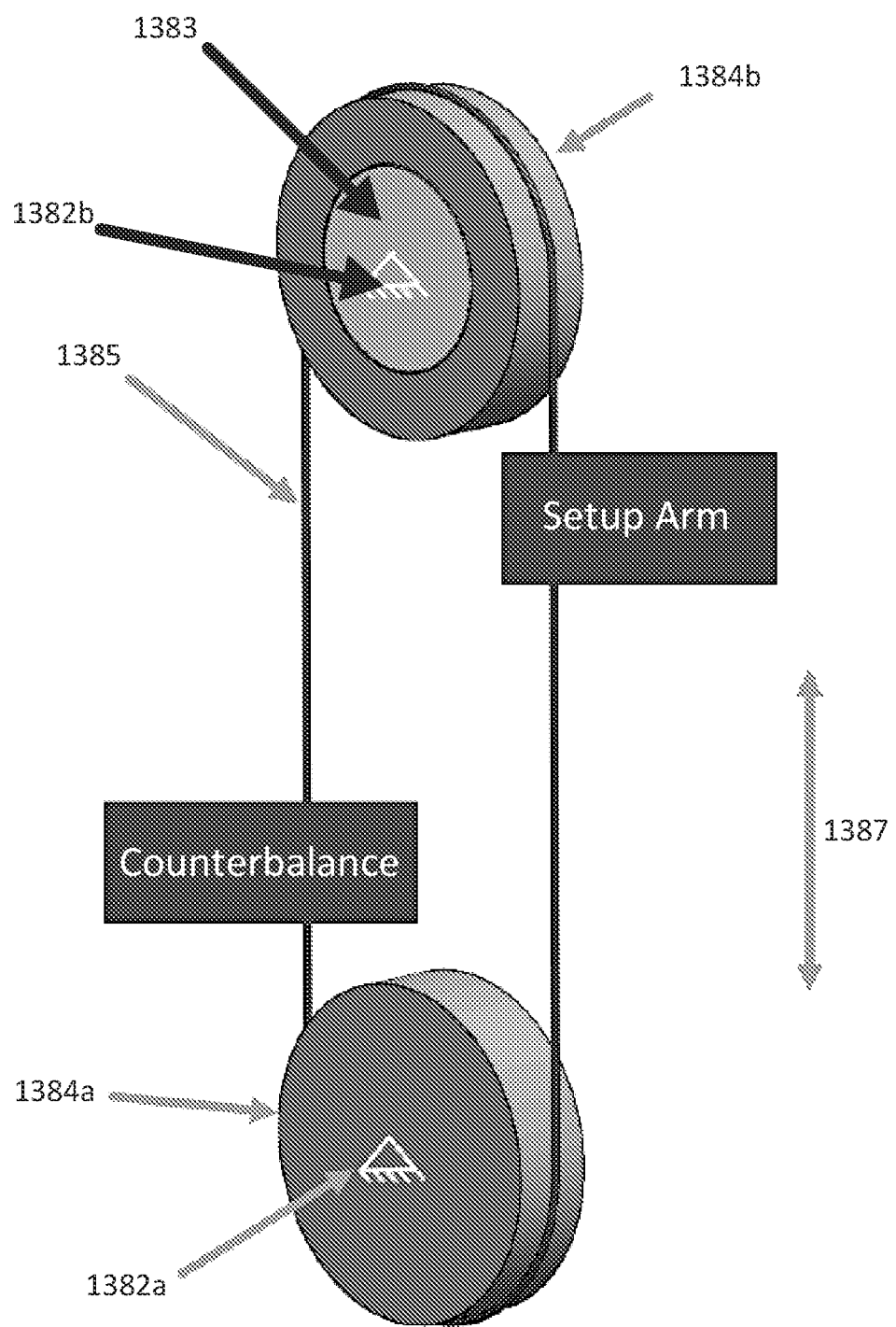
FIG. 13B illustrates a mass-over-pulley system that enables vertical translation of a robotic arm, in accordance with some embodiments.

In some embodiments, the arm support 1310 along which the robotic arm can move linearly in a vertical direction can be coupled to, attached to, or otherwise integrated with a base 1303 (e.g., structurally and/or functionally similar to base 203 in FIG. 2). The linear vertical translation provided by the first proximal axis can be counterbalanced with a mass-over-pulley system illustrated in FIG. 13B. The mass-over-pulley system can include an upper pulley 1348b and a lower pulley 1348a. The upper pulley 1384b can include a fail-safe brake 1383. The point of rotation of the upper pulley 1384b can be point of rotation 1382b and the point of rotation of the lower pulley 1384a can be point of rotation 1382a. A counterbalance can be connected with the robotic arm by a cable 1385 (e.g., wire rope and/or steel bands) over the upper pulley 1384b and the lower pulley 1384a.

In some embodiments, the mass of the counterbalance can be equal to the mass of the robotic arm, thereby balancing the moment load about the upper pulley 1384b. As the robotic arm is raised or lowered, the change in potential energy of the robotic arm can be opposite to the change in potential energy in the counterbalance. This can provide an energy-neutral means to passive balancing. The direction of motion 1387 can be vertical and parallel with gravity. This ensures a 1:1 potential energy transfer between the robotic arm and the counterbalance. The fail-safe brake 1383 can hold the position of the arm support 1310. This brake can be in a "hold" state when power is either off or lost, and in a "free" state when electrical voltage is applied to the fail-safe brake 1383. The robotic arm motion can be constrained to move vertically with a pair of linear recirculating bearing rail (not shown in FIGS. 13A and 13B).

Figure 14:
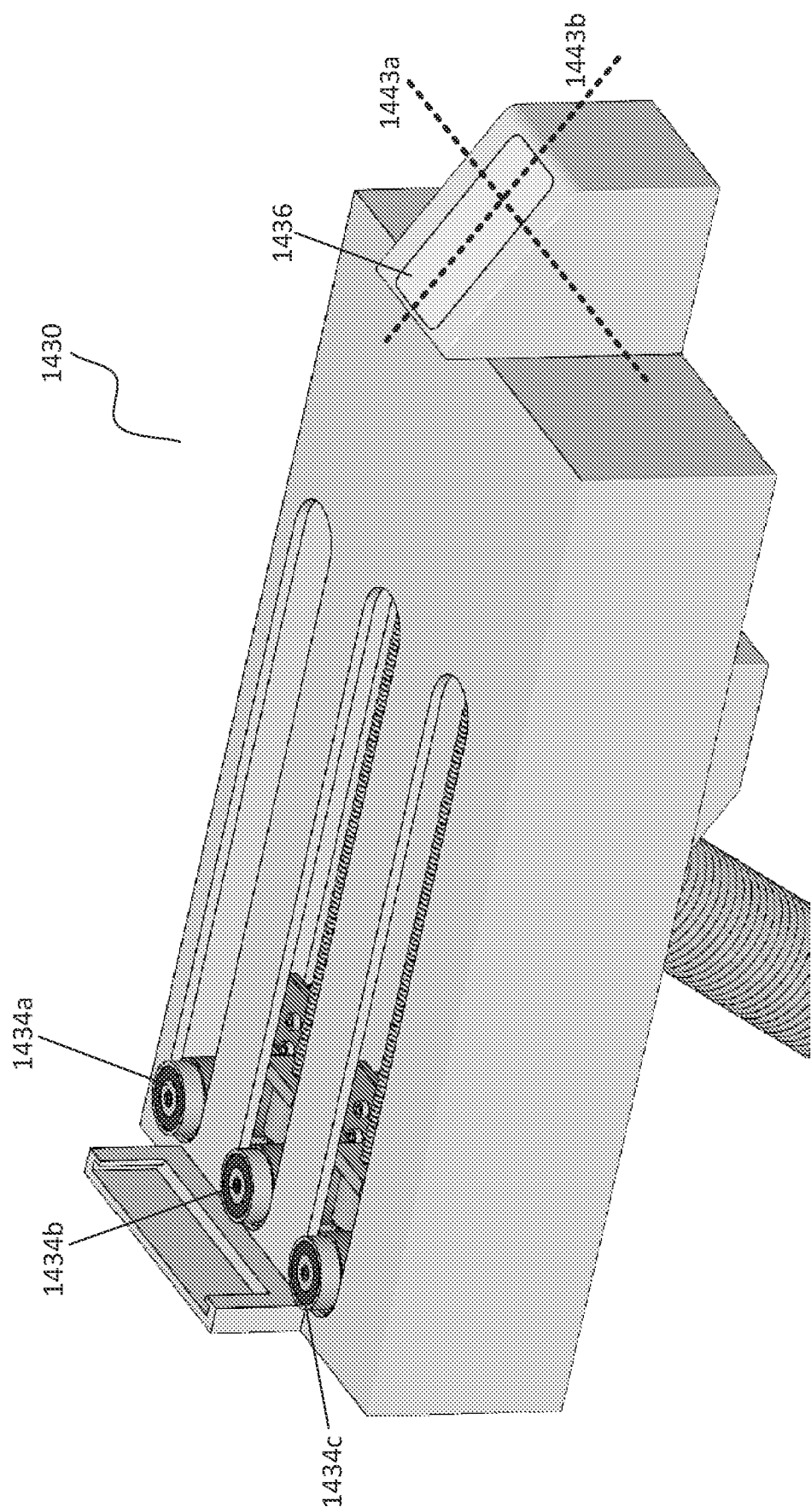
FIG. 14 illustrates a manipulation device, in accordance with some embodiments.

FIG. 14 illustrates a manipulation device 1430 (e.g., structurally and/or functionally similar to manipulation device 230 in FIG. 2), according to some embodiments. The manipulation device 1430 includes a catheter actuator 1434a (e.g., structurally and/or functionally similar to catheter actuator 534a in FIG. 5), a needle actuator 1434b (e.g., structurally and/or functionally similar to needle actuator 534b in FIG. 5), and guidewire actuator 1434c (e.g., structurally and/or functionally similar to guidewire actuator 534c in FIG. 5). The manipulation device 1430 can include an imaging device 1436 (e.g., structurally and/or functionally similar to imaging device 536 in FIG. 5) that can provide a user with a visual aid of a vascular portion (e.g., blood vessel) as the medical procedure is being performed.

Figure 15:
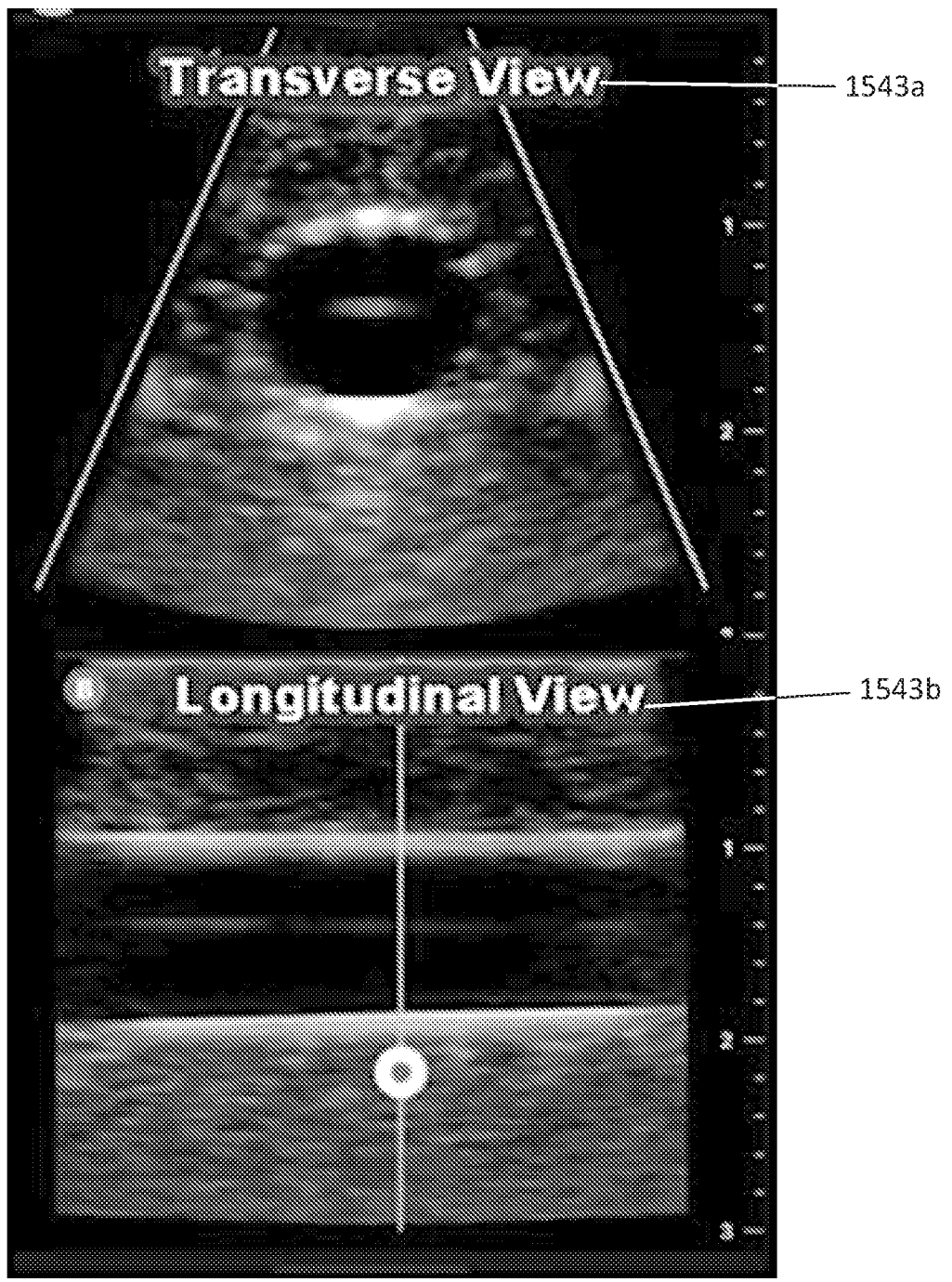
FIG. 15 illustrates a traverse view and a longitudinal view of a blood vessel as captured by an ultrasound imaging device, in accordance with some embodiments.

In some embodiments, the imaging device 1436 can be an ultrasound imaging device that captures a visual representation of a blood vessel. In some embodiments, the imaging device 1436 can be an ultrasound array located on the manipulation device 1430. The ultrasound array can provide two-dimensional ultrasound images along a longitudinal plane 1443b and a transverse plane 1443a. FIG. 15 illustrates a traverse view 1543a and a longitudinal view 1543b of a blood vessel as captured by an ultrasound imaging device (e.g., imaging device 1436 in FIG. 14).

As seen in FIG. 15, the transverse view 1543a of the blood vessel shows a radial cross section of the blood vessel while the longitudinal view 1543b of the blood vessel shows an axial cross section of the blood vessel. As discussed above, the ultrasound array can provide a visual aid of the movement of the needle, catheter, and/or guidewire into the blood vessel. Subsequent movement of the manipulation device can be controlled based on the feedback from the visual aid.

As the needle advances into the field of view of the ultrasound array, the tip of the needle may remain in a central longitudinal plane (e.g., longitudinal plane 1443b in FIG. 14) of the ultrasound array and the manipulation device because the ultrasound array and the manipulation device and/or the robotic arm are physically connected to each other. However, as the tip of the needle advances into the blood vessel, the transverse plane of the needle may not remain in the transverse plane (e.g., transverse plane 1443a in FIG. 14) of the ultrasound array.

In some embodiments, a position encoder on the needle actuator (e.g., needle actuator 534b in FIG. 5) and a limit switch can be used to determine the absolute position of the needle tip. The absolute position of the needle tip can be used to determine which transverse plane to display as a visual aid to the user.

Figure 16A:
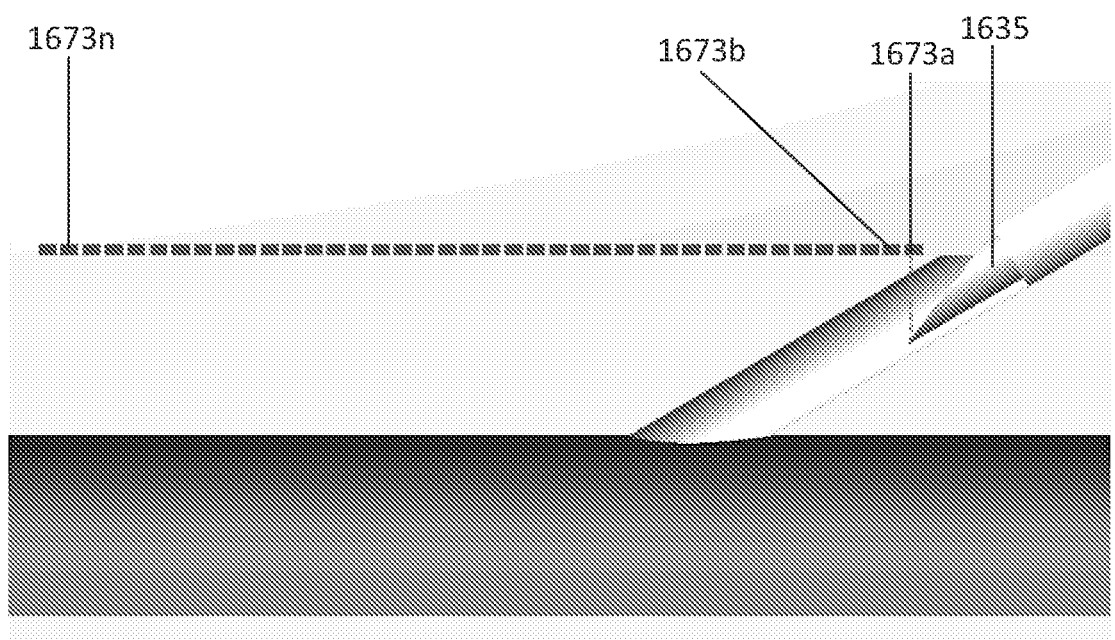
FIGS. 16A-16D illustrate a change in the active transverse elements of a two-dimensional ultrasound array as a tip of the needle advances into the blood vessel, in accordance with some embodiments.

FIGS. 16A-16D illustrate a change in the active transverse elements of the two-dimensional ultrasound array as the tip 1635 of the needle advances into the blood vessel, in accordance with some embodiments. The transverse elements of the two-dimensional ultrasound array are shown in FIG. 16A. The transverse elements include elements in a first row 1673a, second row 1673b, ... nth row 1673n. As seen in FIG. 16A, as the needle is inserted into the blood vessel, the tip 1635 of the needle is under the first row 1673a of the transverse elements of the two-dimensional ultrasound array.

Figure 16B:
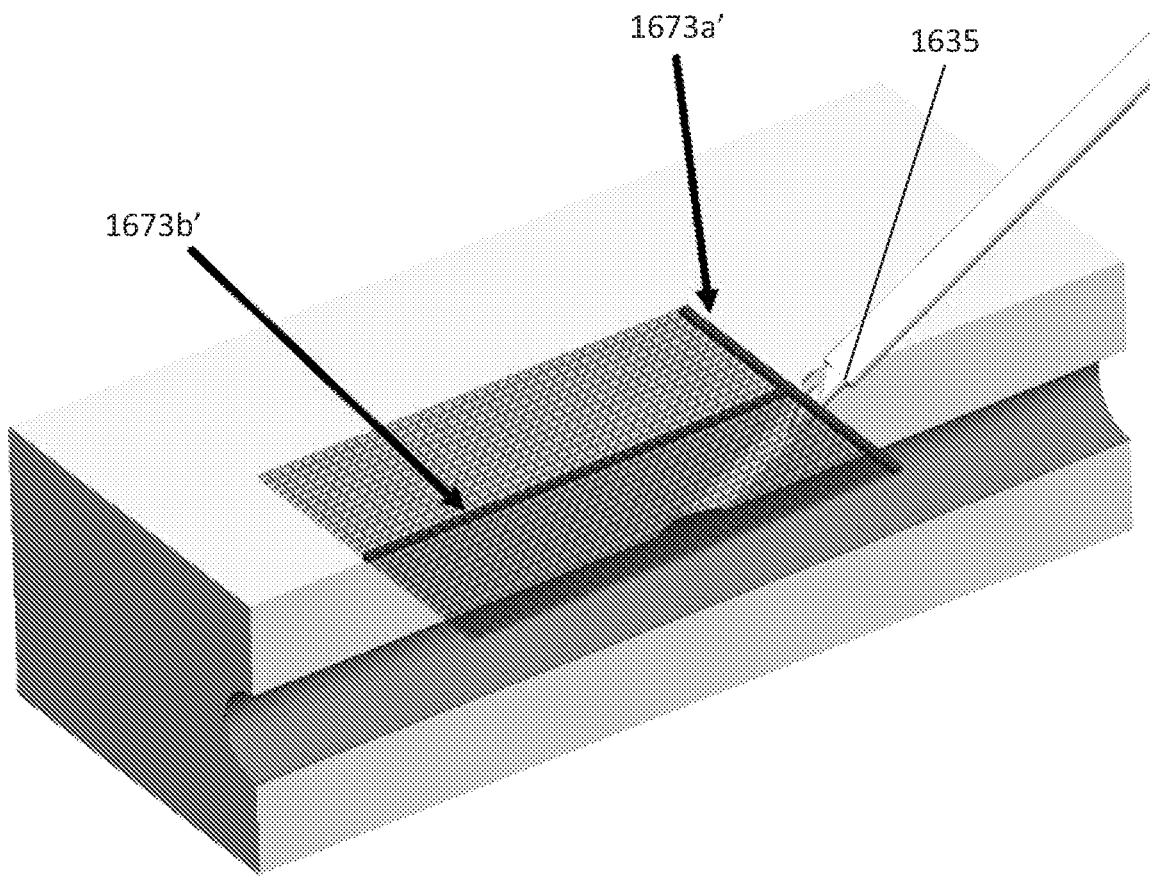
Figure 16C:
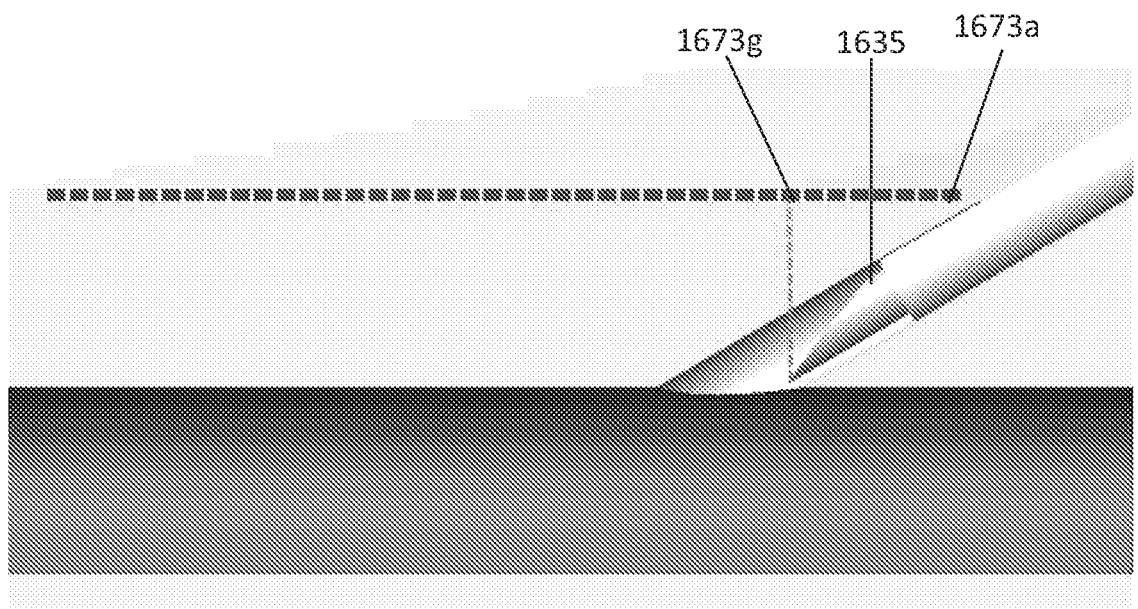

When the tip 1635 of the needle is under the first row 1673a, the transverse elements 1673a' and the longitudinal elements 1673b' of the two-dimensional ultrasound array seen in FIG. 16B become active. The transverse elements 1673a' and the longitudinal elements 1673b' emit and receive the ultrasound signals while the rest of the elements of the two-dimensional ultrasound array remain inactive.

Figure 16D:
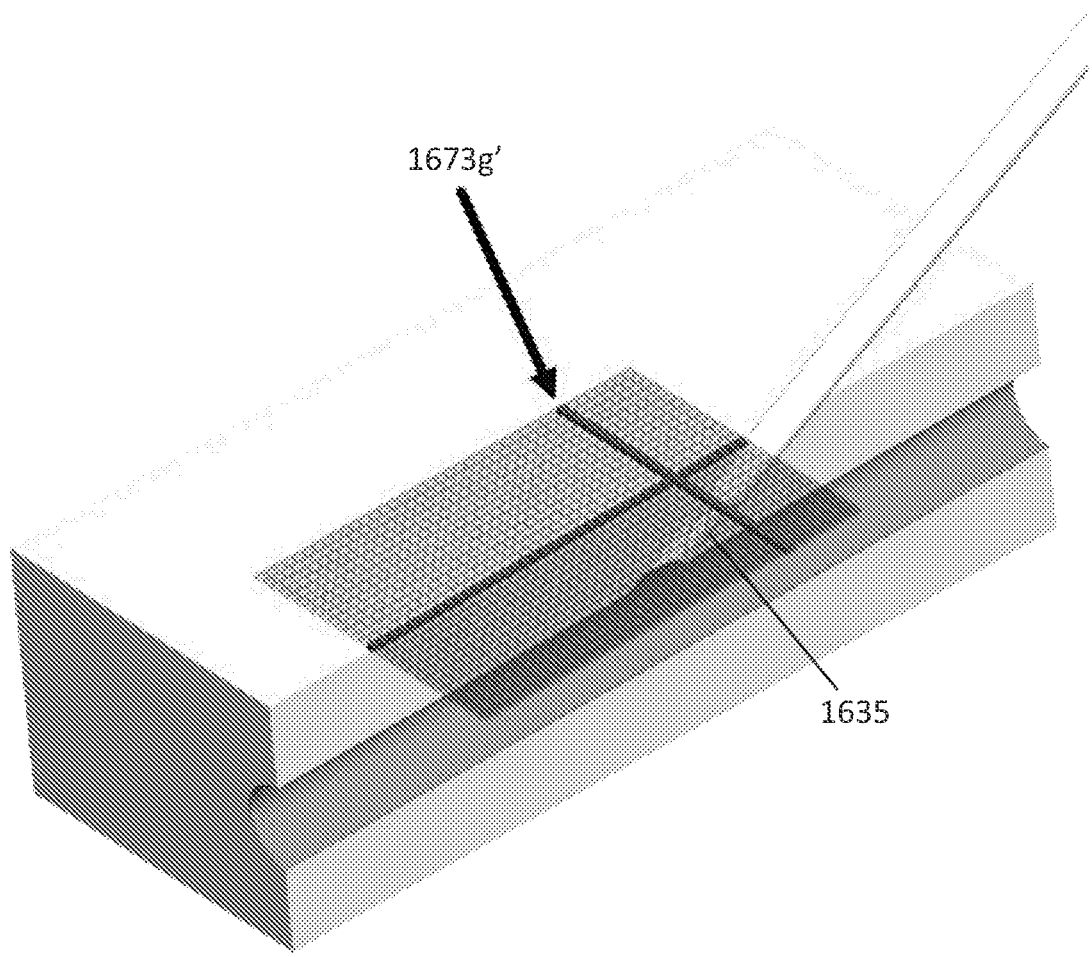

As the needle advances into the blood vessel, for example, as the tip 1635 of the needle advances from under the first row 1673a to under the seventh row 1673g of the transverse elements of the two-dimensional ultrasound array (shown in FIG. 16C), the row of the active transverse elements move. For example, as seen in FIG. 16D, the transverse elements 1673g' become active (i.e., emit and receive ultrasound signals) while the rest of the transverse elements remain inactive. However, the active longitudinal elements 1673b' remain the same. In this manner, the transverse plane is updated as the tip of the needle advances into the blood vessel.

Figure 17:
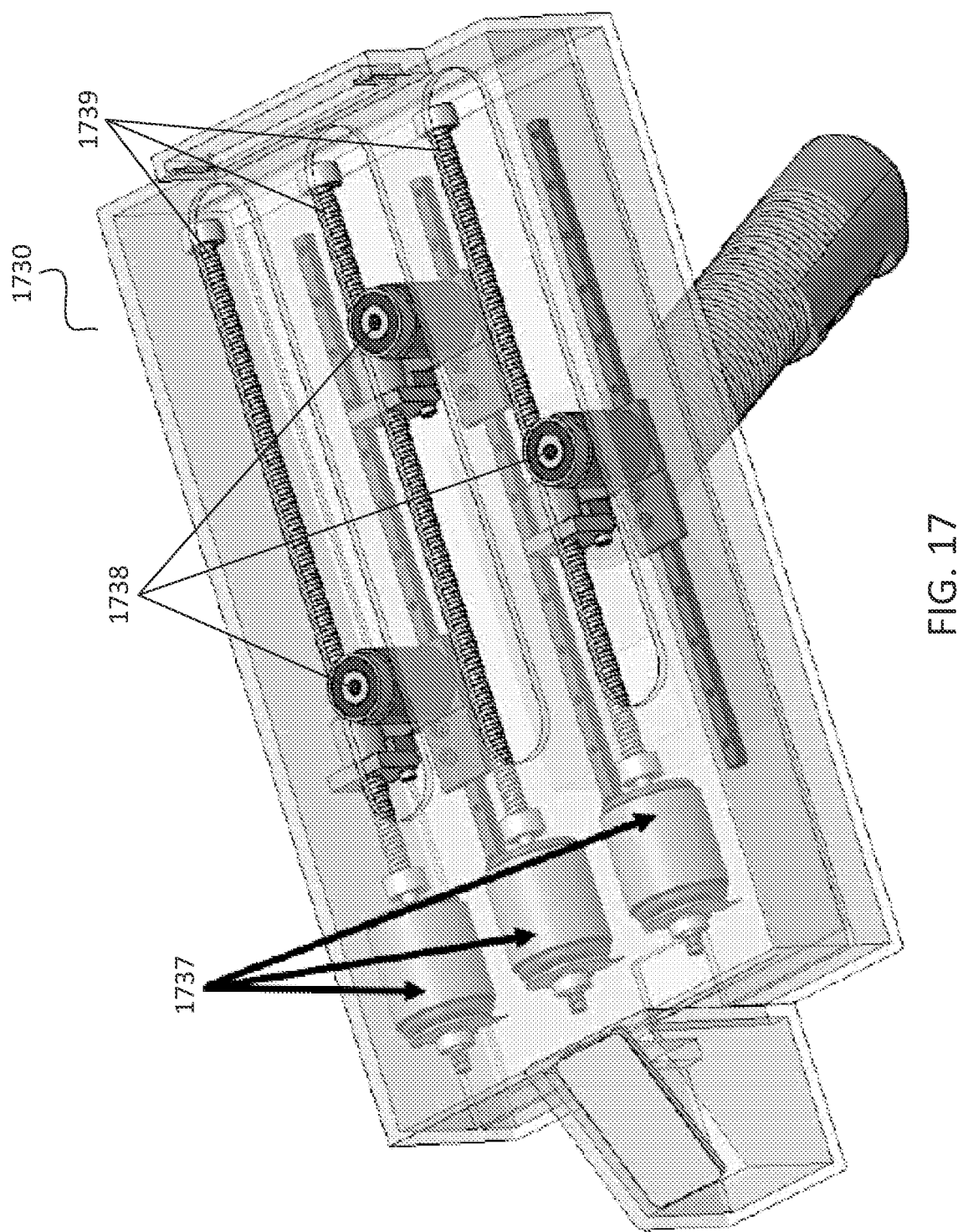
FIG. 17 illustrates a manipulation device, in accordance with some embodiments.

FIG. 17 illustrates a manipulation device 1730 (e.g., structurally and/or functionally similar to manipulation device 230 in FIG. 2 and/or manipulation device 530 in FIG. 5), according to some embodiments. As discussed above, the manipulation device 1730 can include a portion of one or more device actuator(s) that can be configured to actuate the needle, the catheter, and/or the guidewire. In some embodiments, the manipulation device 1730 can include linear actuators that include motors 1737, carriage blocks 1738, and ball screw 1739 to actuate the needle, the catheter, and/or the guidewire. As seen in FIG. 17, the manipulation device 1730 can include three linear actuators along three linear axes to actuator each of the needle, the catheter, and/or the guidewire.

Figure 18:
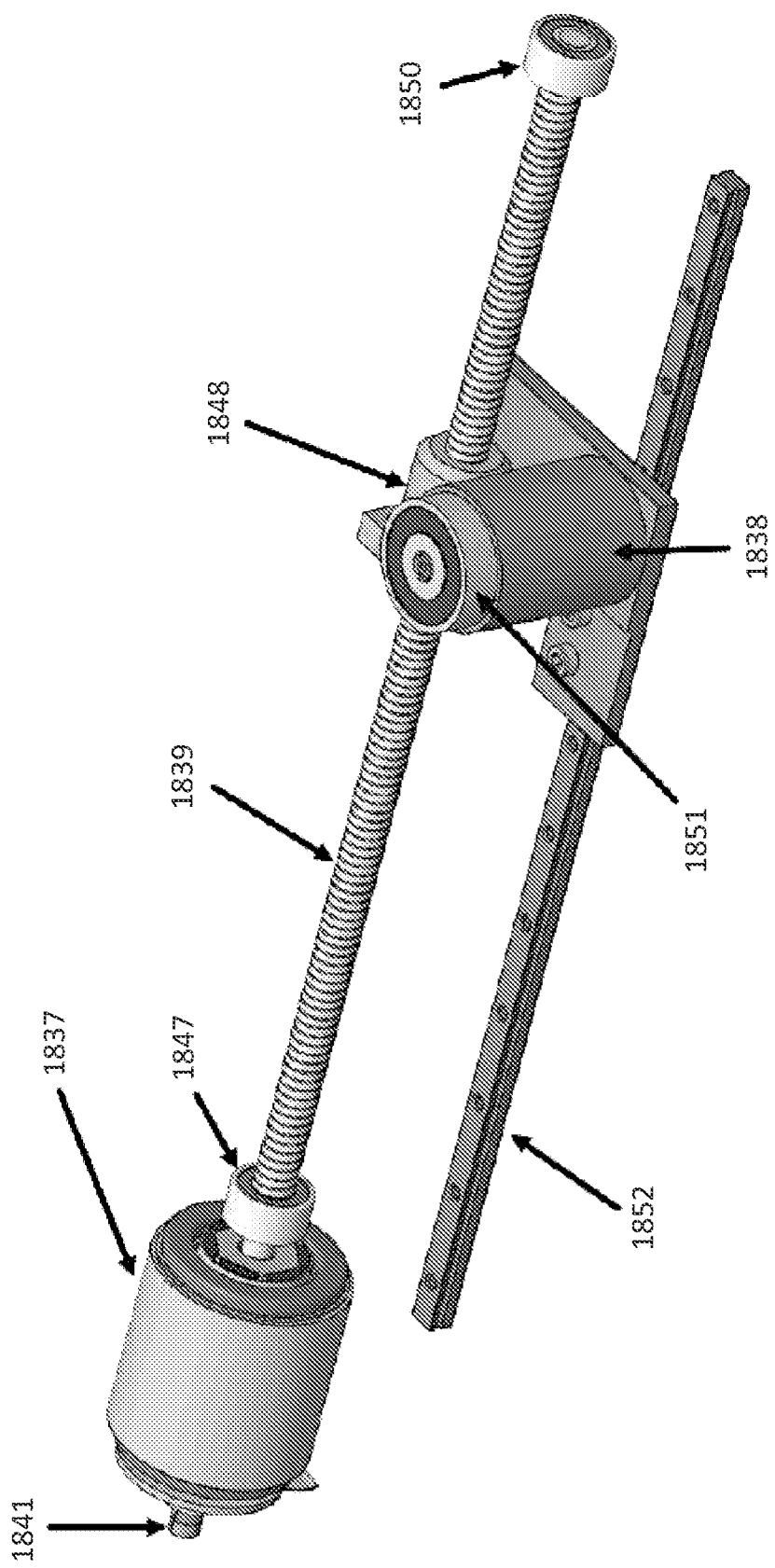
FIG. 18 is an illustration of a linear actuator within the manipulation device that can actuate the needle, the catheter, and/or the guidewire, in accordance with some embodiments.

FIG. 18 is an illustration of a linear actuator within the manipulation device (e.g., structurally and/or functionally similar to manipulation device 230 in FIG. 2 and/or manipulation device 530 in FIG. 5), that can actuate the needle, the catheter, and/or the guidewire, in accordance with some embodiments. As discussed above, the linear actuators can include a brushless DC motor 1837 fixed to a ball screw shaft 1839 supported by ball screw bearings 1847 and 1850. A magnetic encoder 1841 coupled to the brushless DC motor 1837 can sinusoidally commutate the brushless DC motor 1837. A linear circulating ball bearing 1852 can be coupled to a ball screw nut 1848 that is fixed on the ball screw shaft 1839. For instance, the linear circulating ball bearing 1852 can be coupled to the ball screw nut 1848 on the ball screw shaft 1839 via a carriage block 1838. As the ball screw shaft 1839 rotates (e.g., owing to the rotation of the motor's rotor), the ball screw nut 1848 translates as it is constrained by the linear circulating ball bearing 1852 through the carriage block 1838. The translation of the ball screw nut 1848 can in turn actuate the needle, the catheter, and/or the guidewire along a linear axis.

In some embodiments, following the insertion of each of the needle, the catheter, and/or the guidewire, a limit switch (not shown in FIG. 18) can be triggered. An absolute position of the carriage block 1838 can be determined using the limit switch that is triggered each time the linear actuator returns to its home position. In some embodiments, a permanent electromagnet 1851 can be fixed to the carriage block 1838. The permanent electromagnet 1851 in the carriage block 1838 can engage with a coupling element (e.g., puck) in the cartridge assembly, thereby coupling the cartridge assembly with the manipulation device.

Figure 19A:
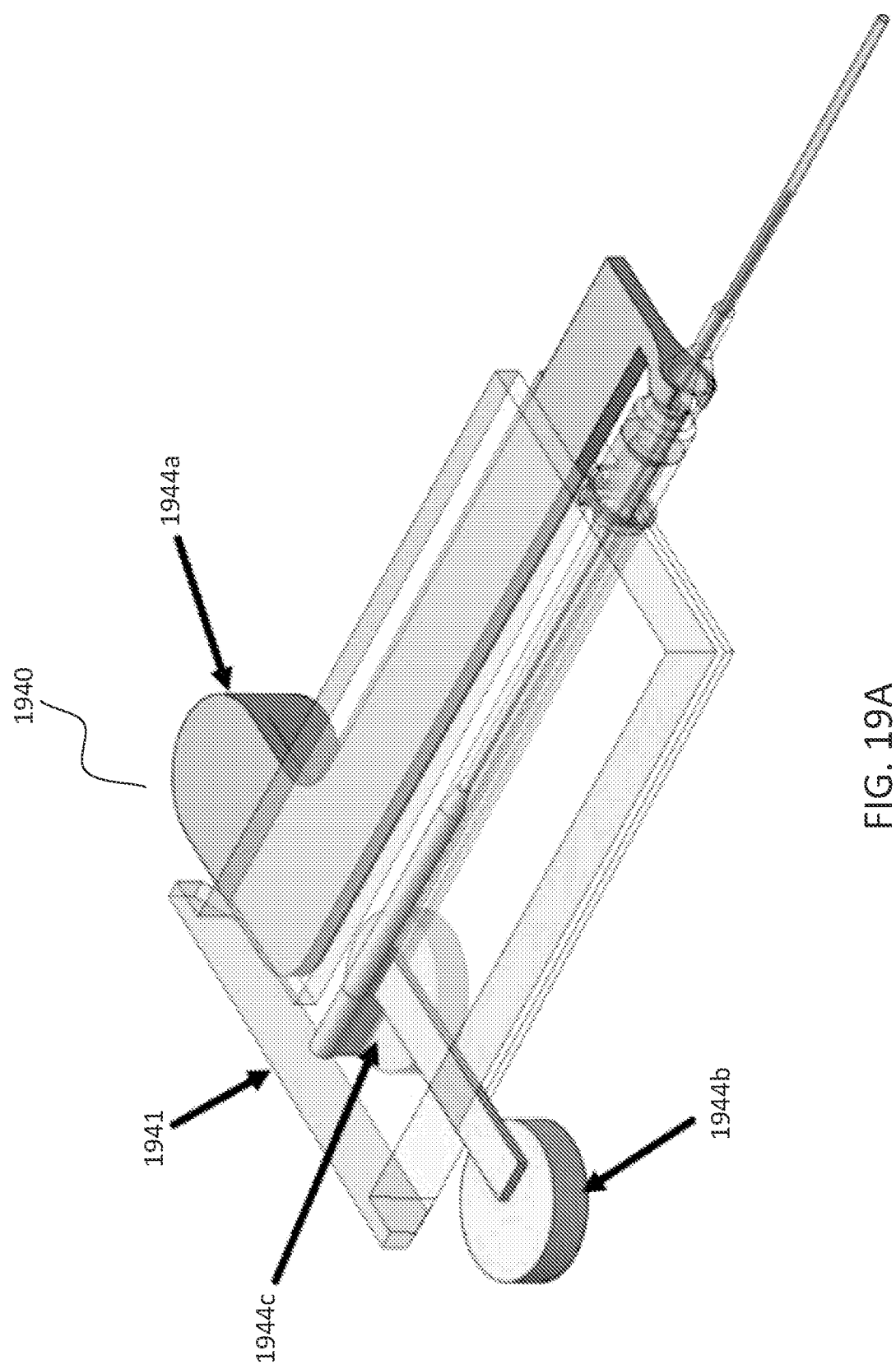
FIG. 19A illustrates a cartridge assembly, in accordance with some embodiments.
Figure 19B:
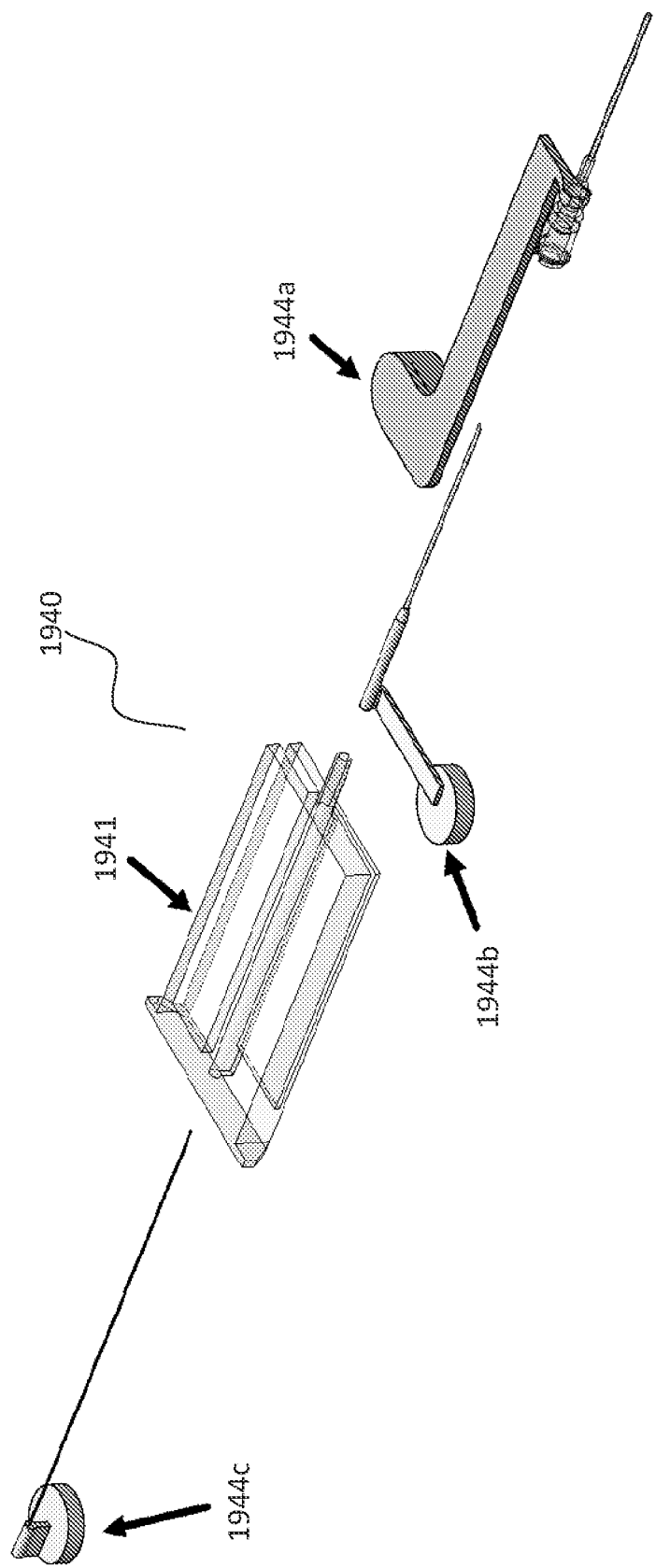
FIG. 19B is an exploded view of a cartridge assembly, in accordance with some embodiments.

FIG. 19A illustrates a cartridge assembly 1940 (e.g., structurally and/or functionally similar to cartridge assembly 540 in FIG. 5), in accordance with some embodiments. The cartridge assembly can include a catheter guide 1944a (e.g., structurally and/or functionally similar to catheter guide 544a in FIG. 5), a needle guide 1944b (e.g., structurally and/or functionally similar to needle guide 544b in FIG. 5), and a guidewire guide 1944c (e.g., structurally and/or functionally similar to guidewire guide 544c in FIG. 5) in a housing 1941. Each of the needle, catheter, and guidewire can be attached to a respective guide that guides them along the linear axis as they are actuated by the linear actuators in the manipulation device. The needle, catheter, and the guidewire can be moved along a respective linear axis relative to the static housing 1941. FIG. 19B is an exploded view of the cartridge assembly 1940 in FIG. 19A, in accordance with some embodiments.

Figure 20B:
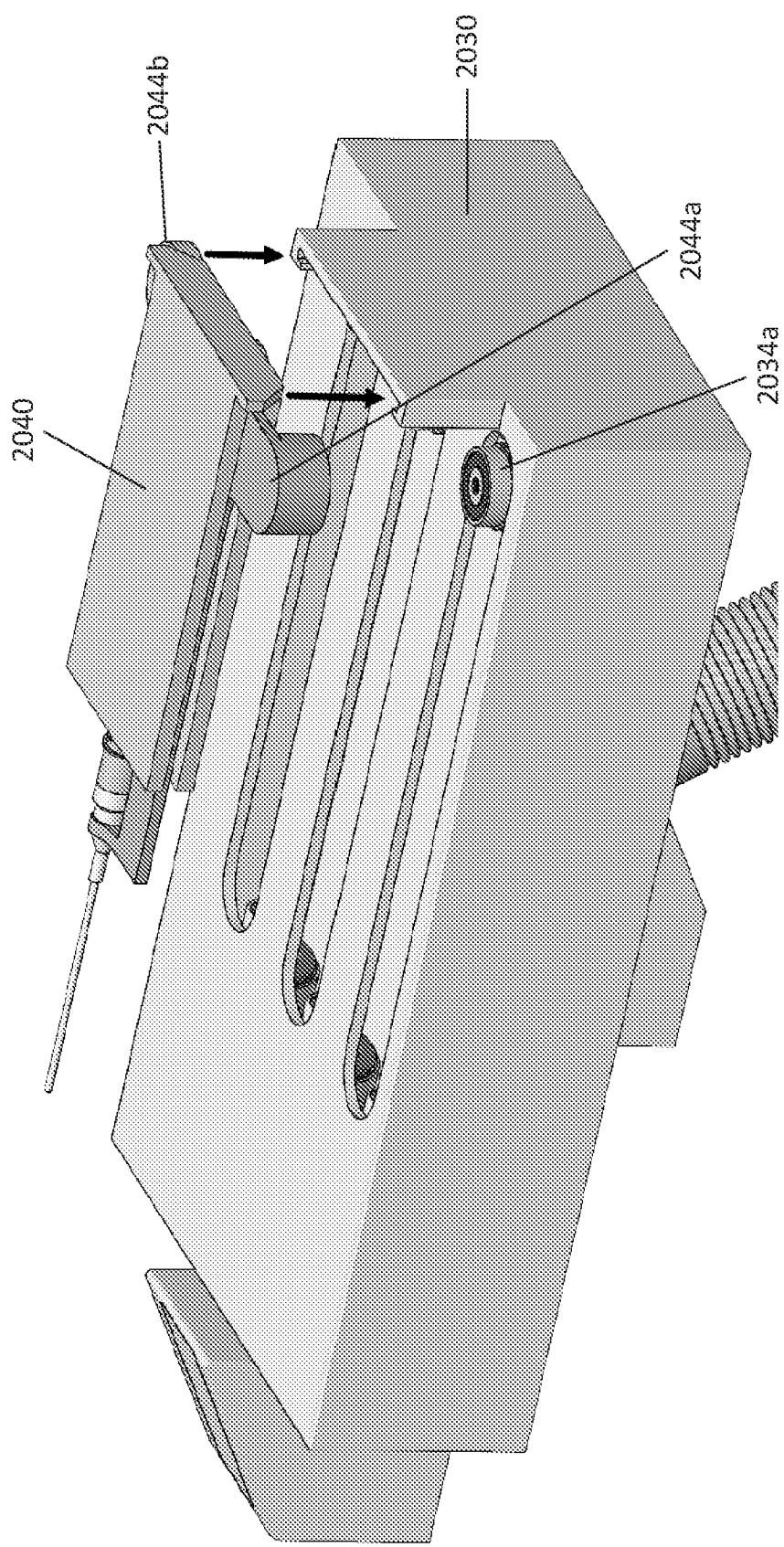

FIGS. 20A and 20B illustrate attaching and/or coupling a cartridge assembly 2040 (e.g., structurally and/or functionally similar to cartridge assembly 540 in FIG. 5) to a manipulation device 2030 (e.g., structurally and/or functionally similar to manipulation device 230 in FIG. 2 and/or manipulation device 530 in FIG. 5), according to some embodiments. The cartridge assembly 2040 can be attached to the manipulation device 2030 by placing the cartridge assembly 2040 normal to the surface of the linear actuators (e.g., linear actuator 2034a to actuate the catheter, linear actuator 2034b to actuate the needle in FIG. 20A) in the manipulation device 2030.

In some embodiments, one or more mechanical engagement features between the cartridge assembly 2040 and the manipulation device 2030 can mechanically couple the cartridge assembly 2040 to the manipulation device. For example, the housing of the cartridge assembly 2040 can include features such as tabs that fit within slots in the housing of the manipulation device 2030 as seen in FIG. 20B.

Additionally or alternatively, the catheter guide 2044a, the needle guide 2044b, and the guidewire guide 2044c can each include a coupling element such as a puck that comprises an injection molded plastic with an embedded steel disk. As discussed above, the carriage block in the linear actuators in the manipulation device 2030 can include a permanent electromagnet. The permanent electromagnet engages with a respective puck in the catheter guide, the needle guide, and the guidewire guide. The embedded steel disk in the puck can act as an armature to close the magnetic circuit in the permanent electromagnet, thereby engaging the cartridge assembly 2040 with the manipulation device 2030. This allows the pucks to be attached in both power-on and power-off scenarios, creating a fail-safe interface. Current can be applied to the permanent electromagnet in order to release the puck.

Figure 21A:
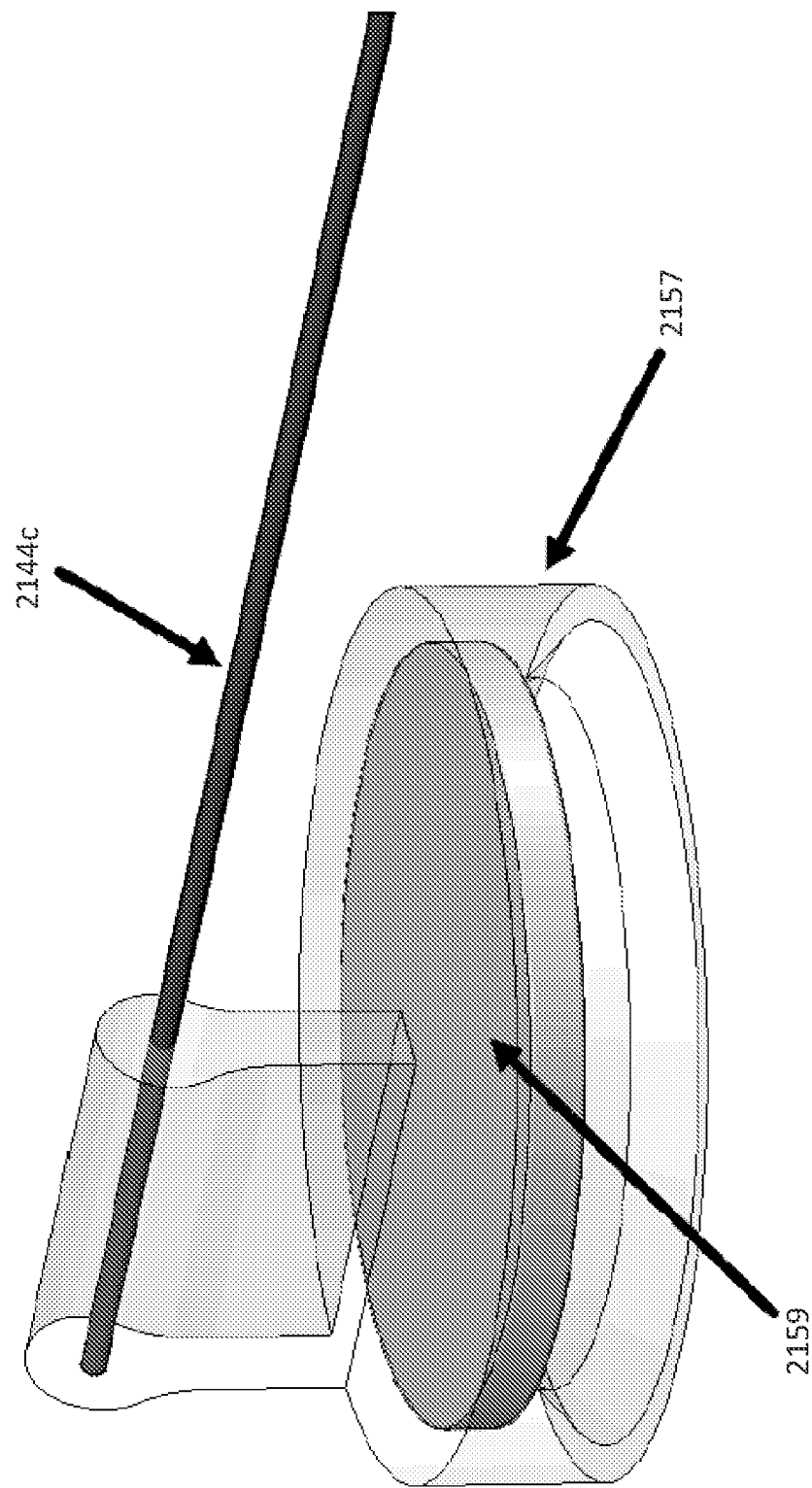
FIG. 21A illustrates a puck included in the cartridge assembly, in accordance with some embodiments.
Figure 21B:
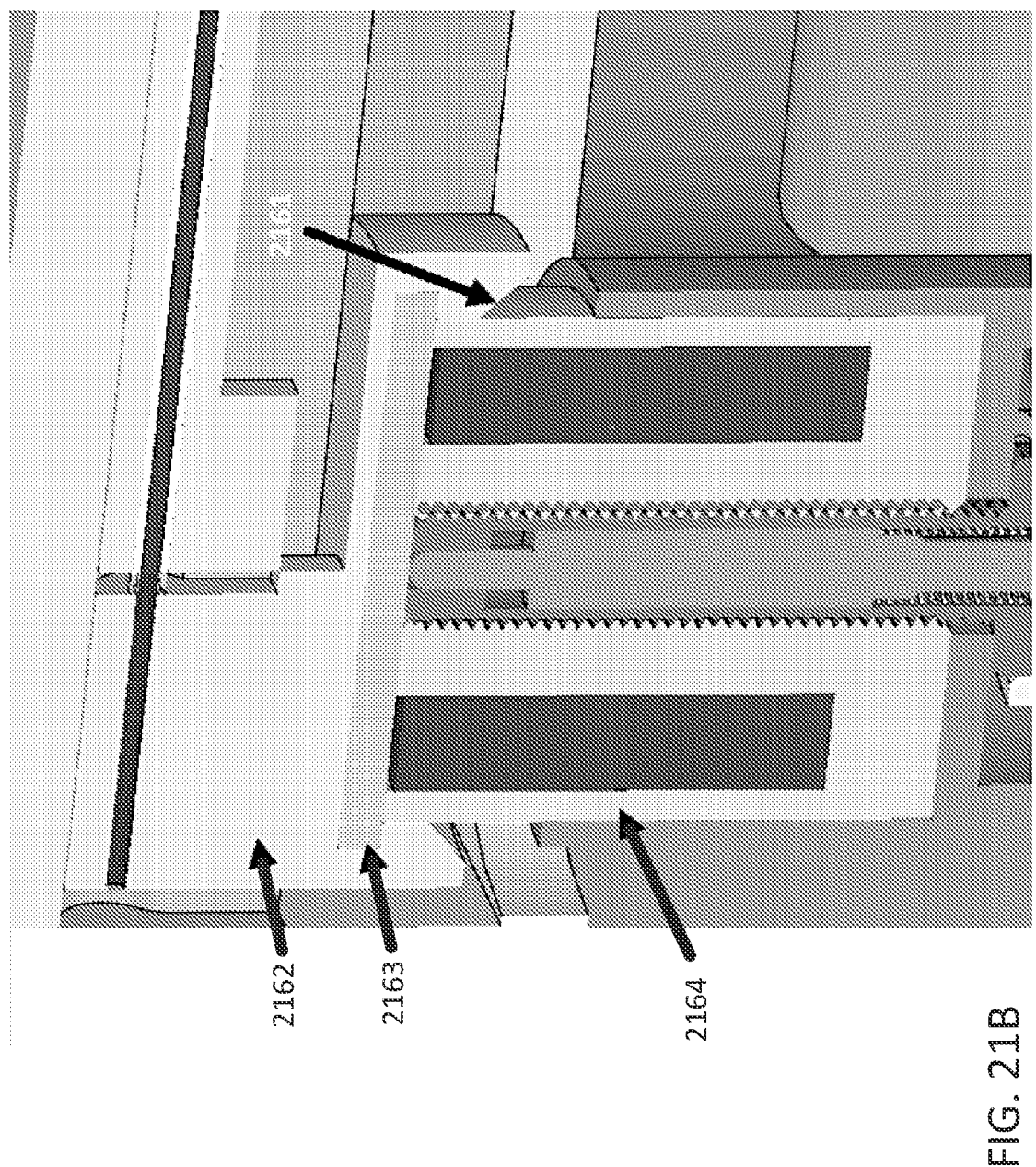
FIG. 21B illustrates a coupling between a manipulation device and a cartridge assembly, in accordance with some embodiments.

FIG. 21A illustrates a puck with injection molded plastic 2157 that includes an embedded steel disk 2159. A guidewire guide 2144c can be attached to the puck as seen in FIG. 21A. FIG. 21B illustrates a coupling between a manipulation device (e.g., structurally and/or functionally similar to manipulation device 230 in FIG. 2 and/or manipulation device 530 in FIG. 5) and a cartridge assembly (e.g., structurally and/or functionally similar to cartridge assembly 540 in FIG. 5), according to some embodiments. As seen in FIG. 21B, the puck 2162 that includes the embedded steel disk 2163 is magnetically engaged with the permanent electromagnet 2164. The lead-in chamber 2161 can aid in the kinematic alignment of the puck 2162 and the permanent electromagnet 2164.

Figure 22B:
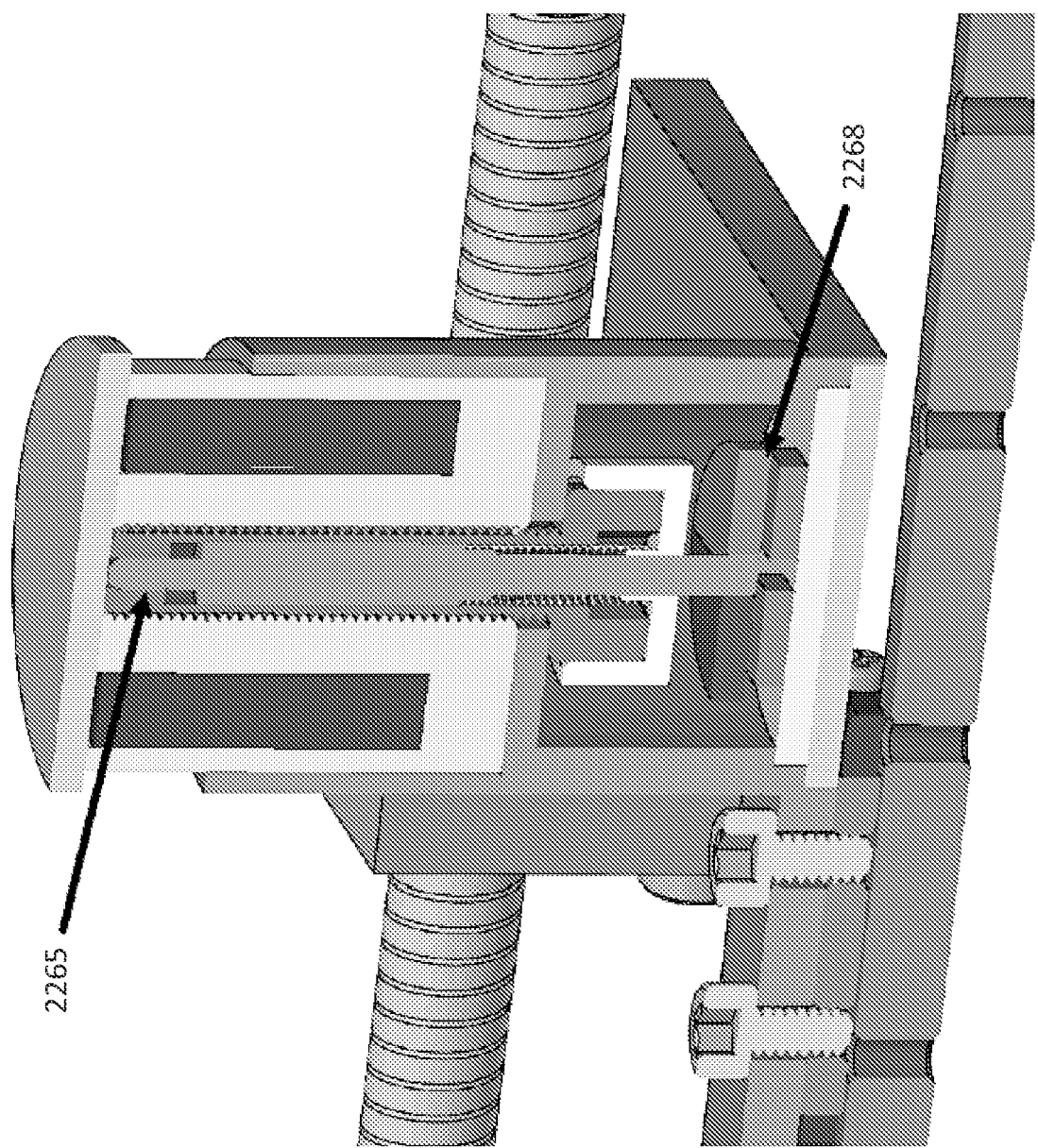

FIGS. 22A and 22B illustrate a mechanism to detect a coupling between a permanent electromagnet in a manipulation device (e.g., structurally and/or functionally similar to manipulation device 230 in FIG. 2 and/or manipulation device 530 in FIG. 5) and a puck in a cartridge assembly (e.g., structurally and/or functionally similar to cartridge assembly 540 in FIG. 5), according to some embodiments. A carriage block (e.g., structurally and/or functionally similar to carriage block 1738 in FIG. 17) can include a plunger 2265 in a threaded housing 2266. A compressed spring 2267 can aid to the up and down movement of the plunger 2265. The radially magnetized magnet 2268 (e.g., permanent magnet) can be positioned above 2x Hall Effect sensors 2269. In FIG. 22A, the plunger 2265 is in an "UP" position. When the magnet 2268 pulls in the magnetic portion (e.g., embedded steel disk) in the puck of the cartridge assembly, the plunger 2265 is forced down as shown in FIG. 22B. This moves the magnet 2268 closer to the 2x Hall Effect sensors 2269. The 2x Hall Effect sensors 2269 can measure the change in magnetic field intensity associated with the two positions of the plunger 2265.

Figure 23A:
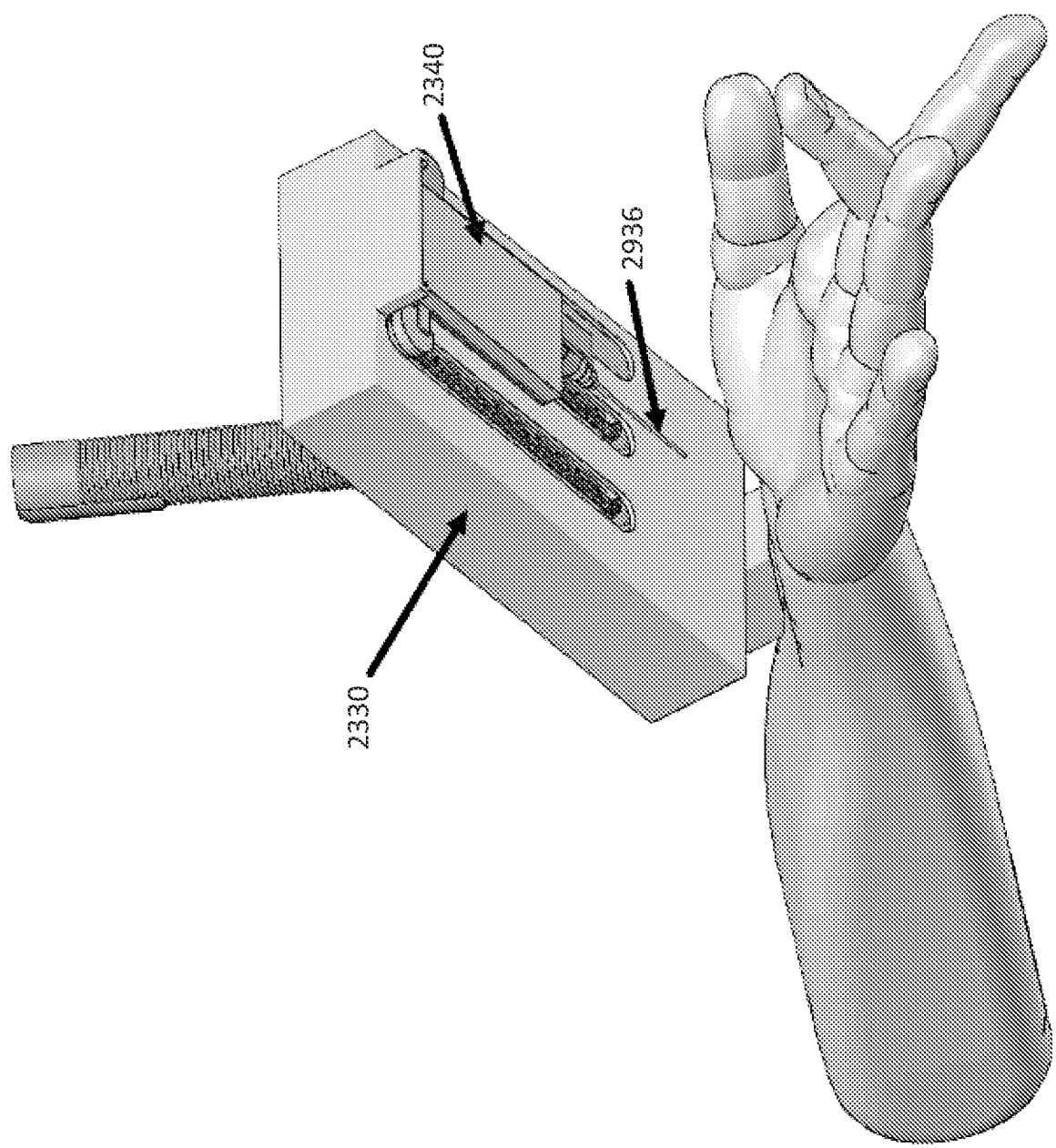
FIGS. 23A and 23B illustrate the anatomical positioning of the manipulation device with respect to a blood vessel, in accordance with some embodiments.
Figure 23B:
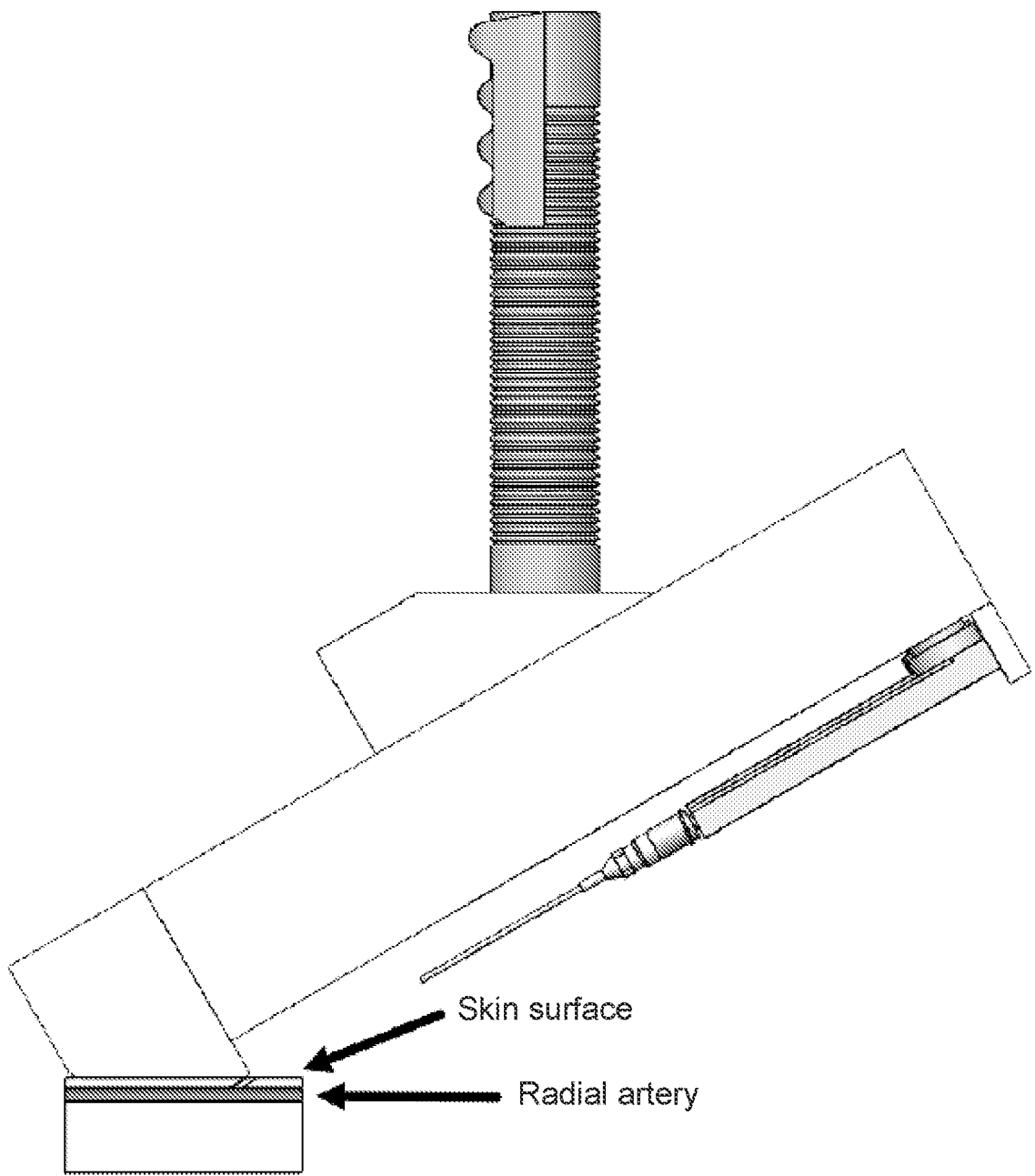

FIGS. 23A and 23B illustrate the anatomical positioning of the manipulation device 2330 with respect to a blood vessel, in accordance with some embodiments. As seen in FIGS. 23A an 23B, the manipulation device 2330 is positioned at an angle relative to the arm of a subject, and thereby at an angle relative to the blood vessel. For instance, the manipulation device can be at any suitable angle (e.g., angle between about 20 degrees to about 60 degrees) relative to the blood vessel. The cartridge 2340 can include the catheter along with needle and/or guidewire (e.g., 2936) to access the blood vessel based on the angle of the manipulation device 2330 relative to the arm of the subject.

FIGS. 24A-24F illustrate the steps of the Seldinger technique performed using the manipulation device (e.g., structurally and/or functionally similar to manipulation device 230 in FIG. 2 and/or manipulation device 530 in FIG. 5) and the cartridge assembly (e.g., structurally and/or functionally similar to cartridge assembly 540 in FIG. 5) described herein.

Figure 24A:
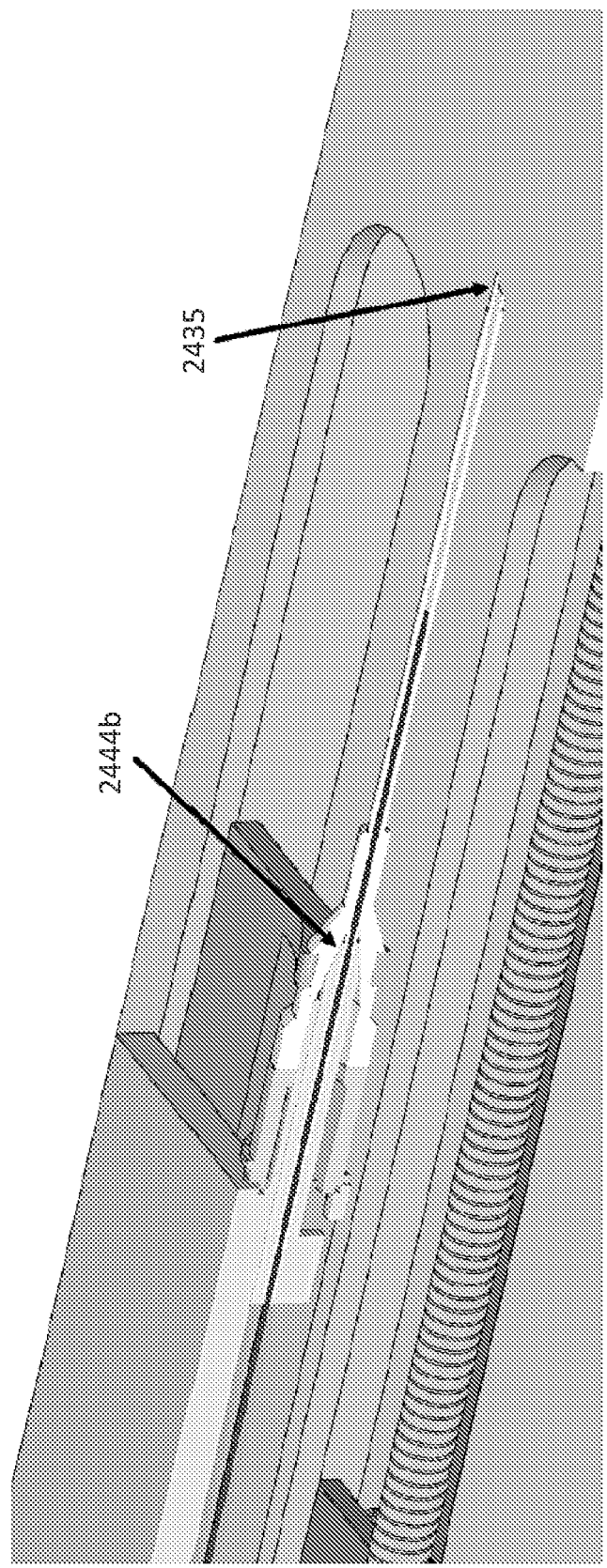
FIGS. 24A-24F illustrate the steps of the Seldinger technique performed using a manipulation device and a cartridge assembly, in accordance with some embodiments.
Figure 24B:
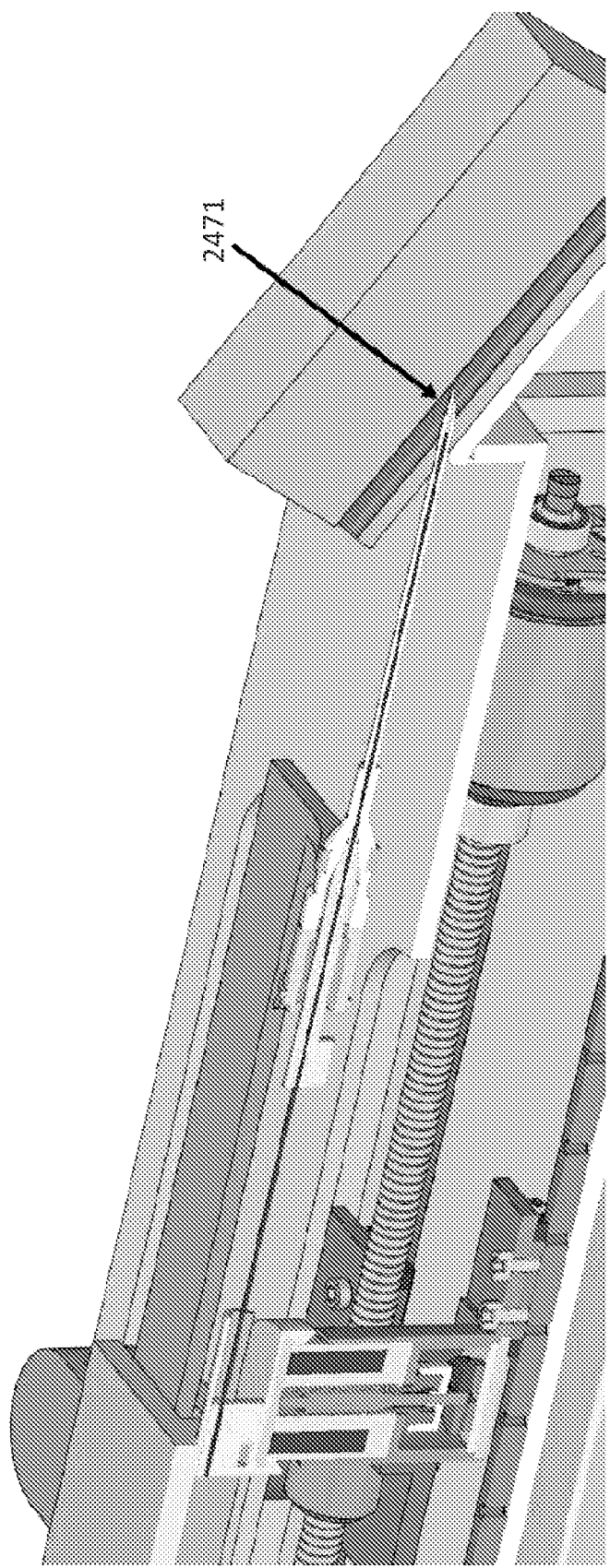

As shown in FIG. 24A, the first step involves aligning a needle end with a catheter tip. FIG. 24A shows a needle guide 2444b that is tangent to an internal catheter bore and a needle tip 2435 that is outside the catheter lumen. In FIG. 24B, the needle tip 2435 is inserted into an artery 2471. As discussed above, as the needle tip advances into the field of view of an imaging device such as an ultrasound array, the needle tip will remain the longitudinal plane as the ultrasound array. However, the transverse plane of the needle tip changes as the needle advances.

Figure 24C:
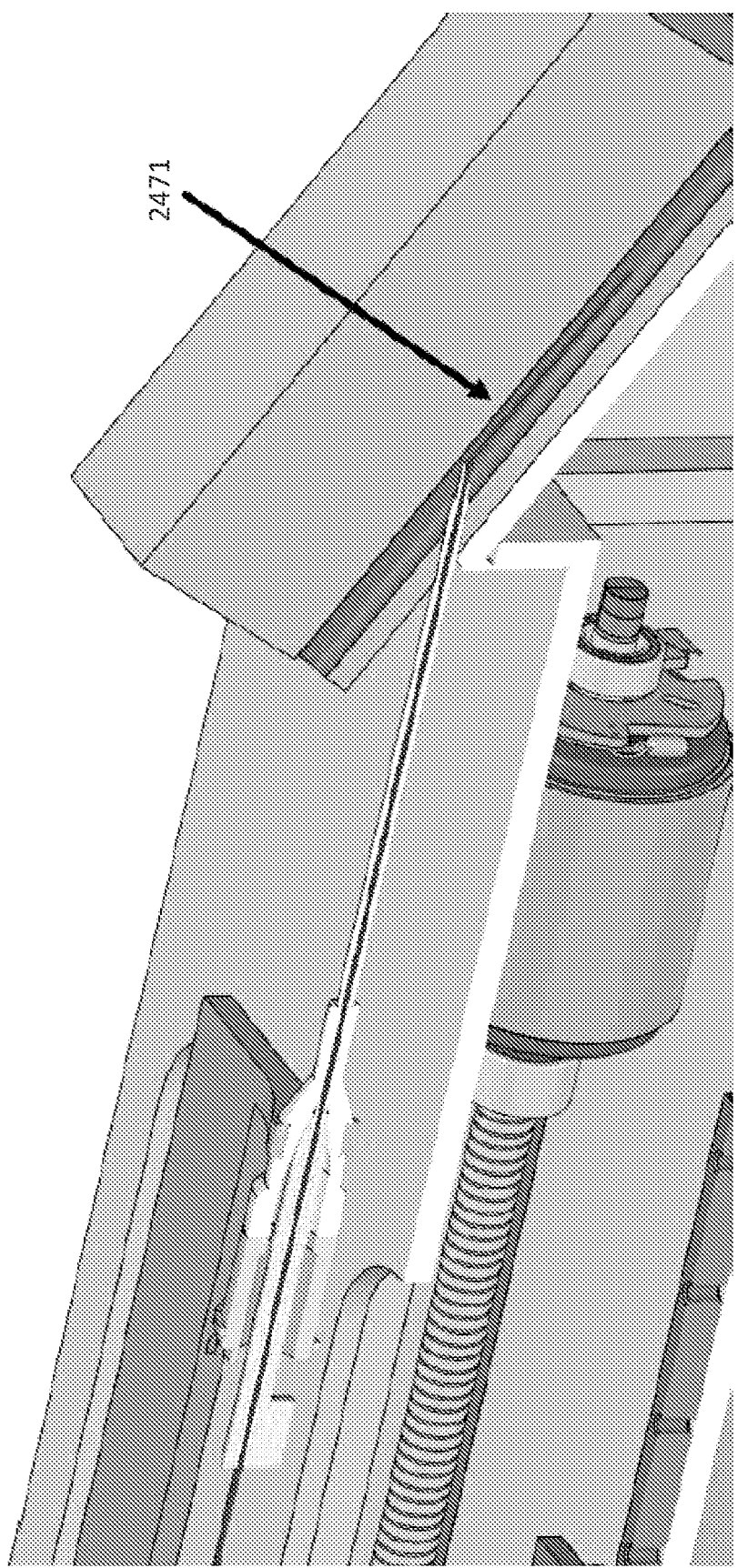

In FIG. 24C, the guidewire is advanced into the artery 2471. The needle guide and the catheter guide can be held stationary when the guidewire is inserted. If the guidewire is visible in an imaging device such as an ultrasound array, the transverse plane can be updated in a manner similar to the needle tip in order to visualize the guidewire.

Figure 24D:
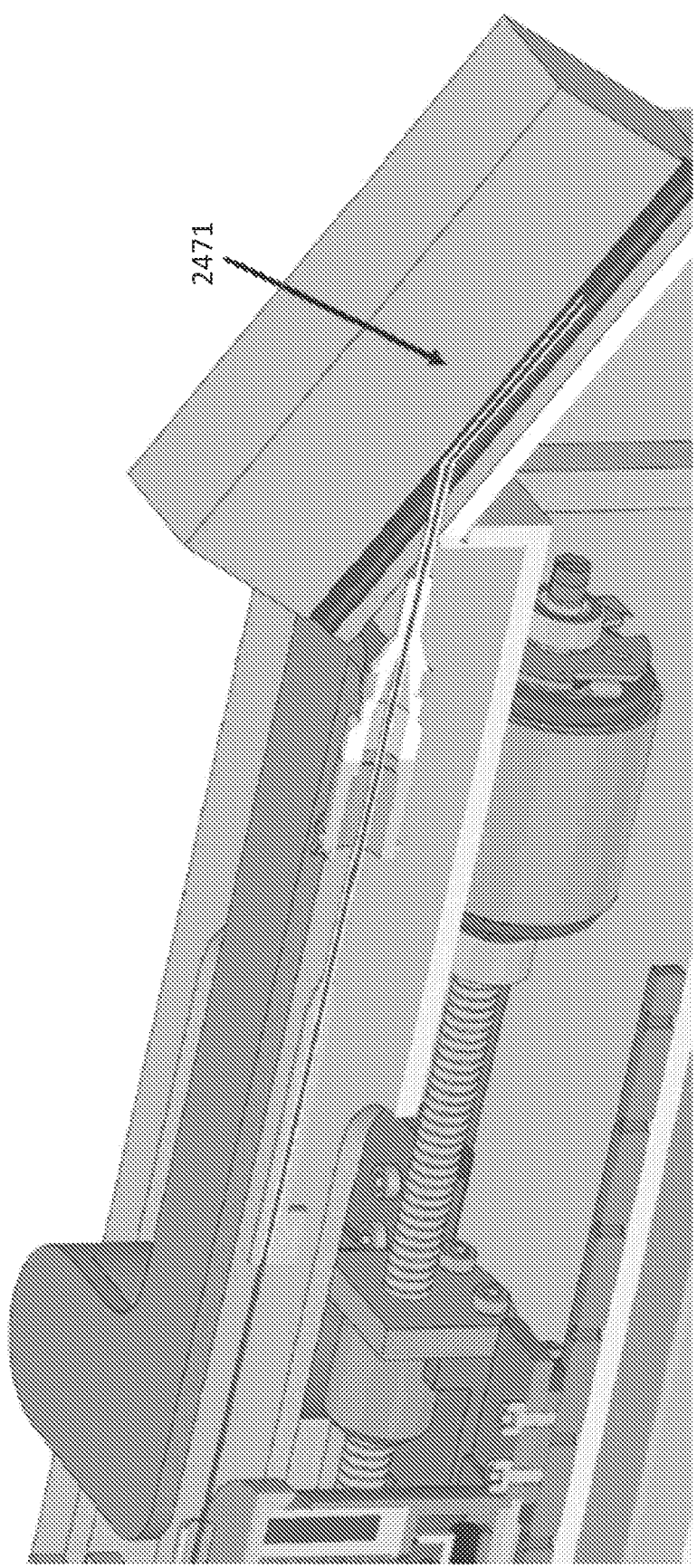
Figure 24E:
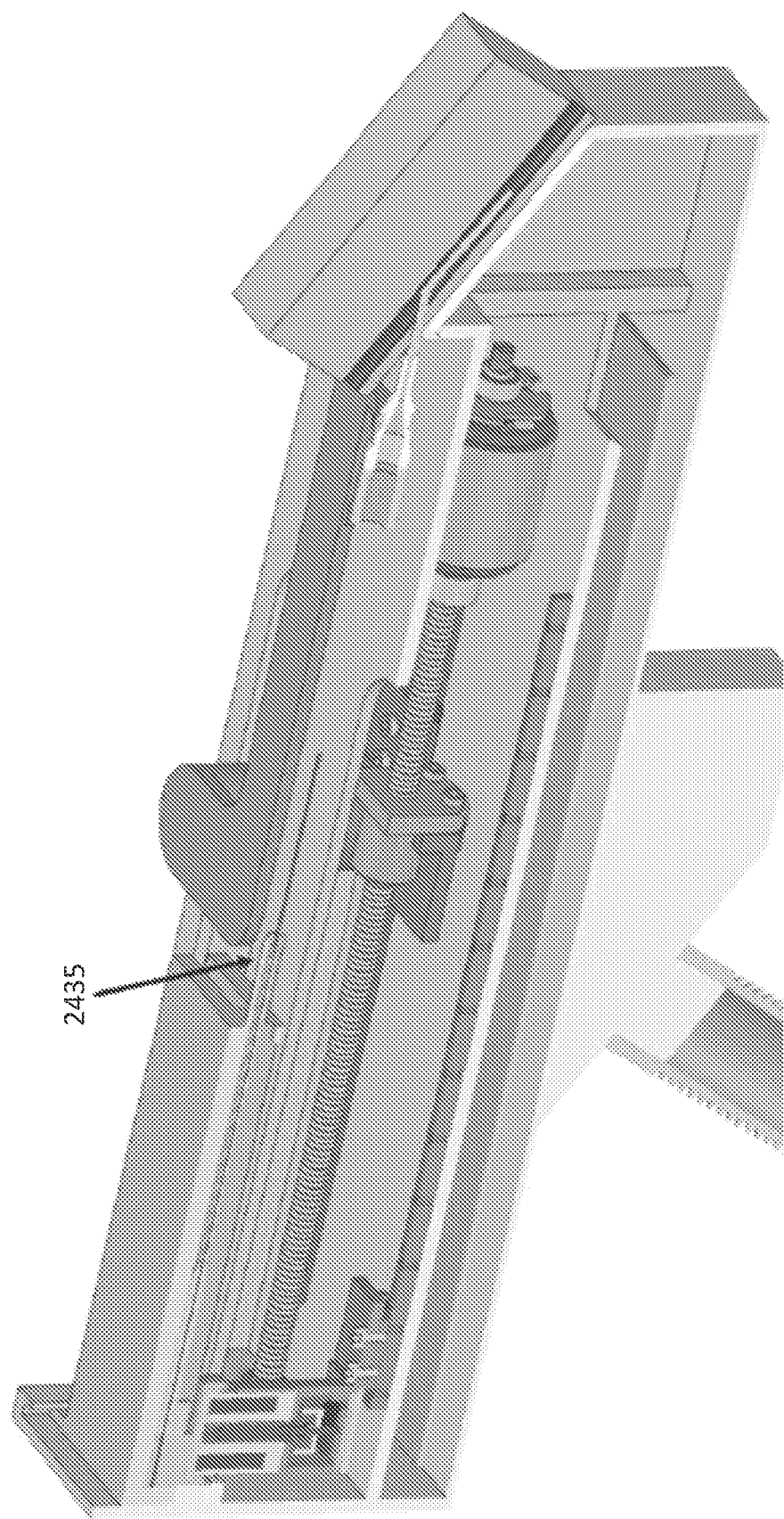
Figure 24F:
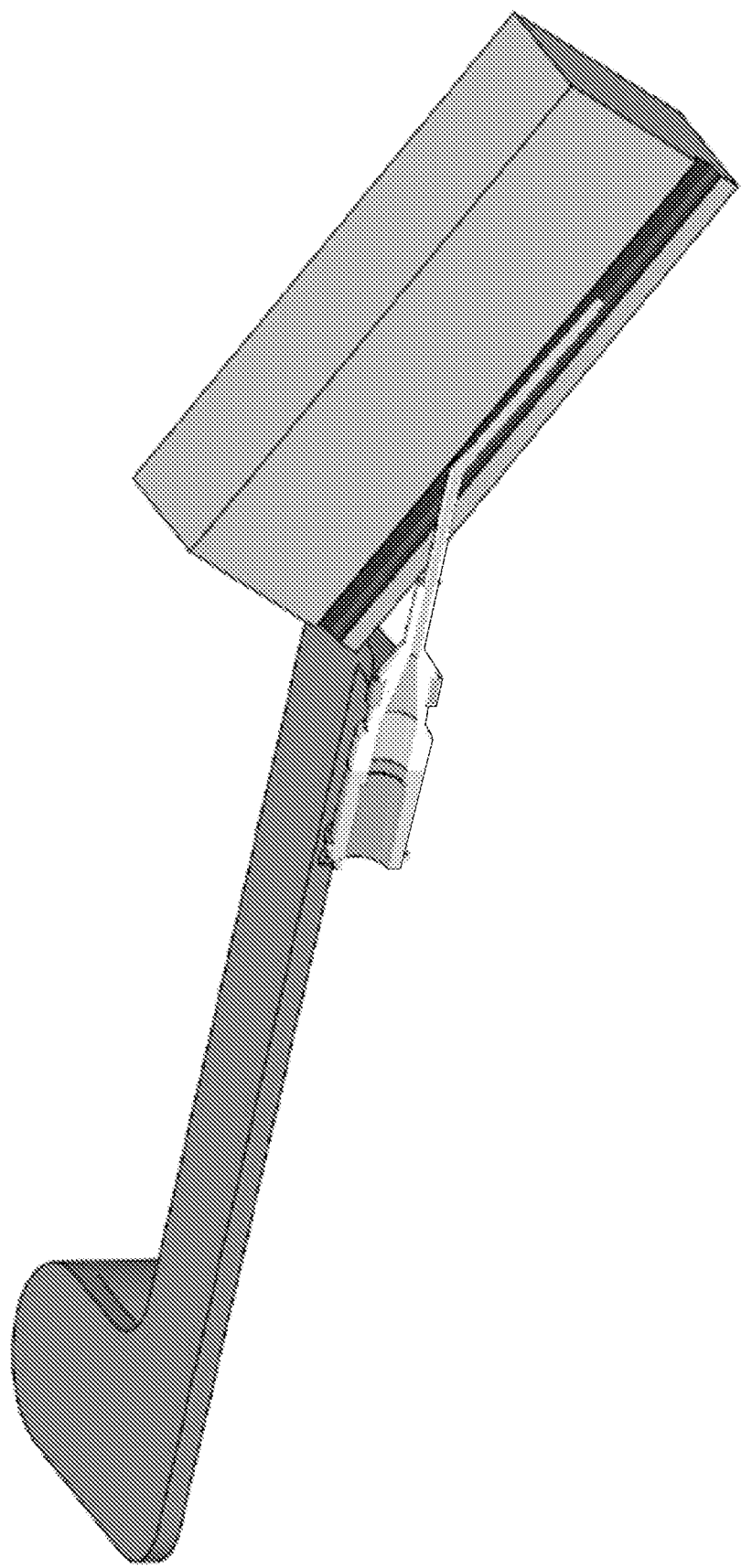

In FIG. 24D, the catheter is advanced into the artery 2471. In FIG. 24E, the needle and the guidewire are retracted. In FIG. 24F, the permanent electromagnet in the carriage block included in the linear actuator that actuates the catheter can be energized in order to release the catheter from the manipulation device. In some embodiments, the catheter may include a hole on the top of the catheter to prevent blood from coming out. As an alternative step to FIG. 24F, the user can manually detach the catheter from the catheter guide instead of energizing the permanent electromagnet. FIG. 25 is a table illustrating the states of the needle actuator, catheter actuator, and guidewire actuator for the Seldinger technique.

Figure 26:
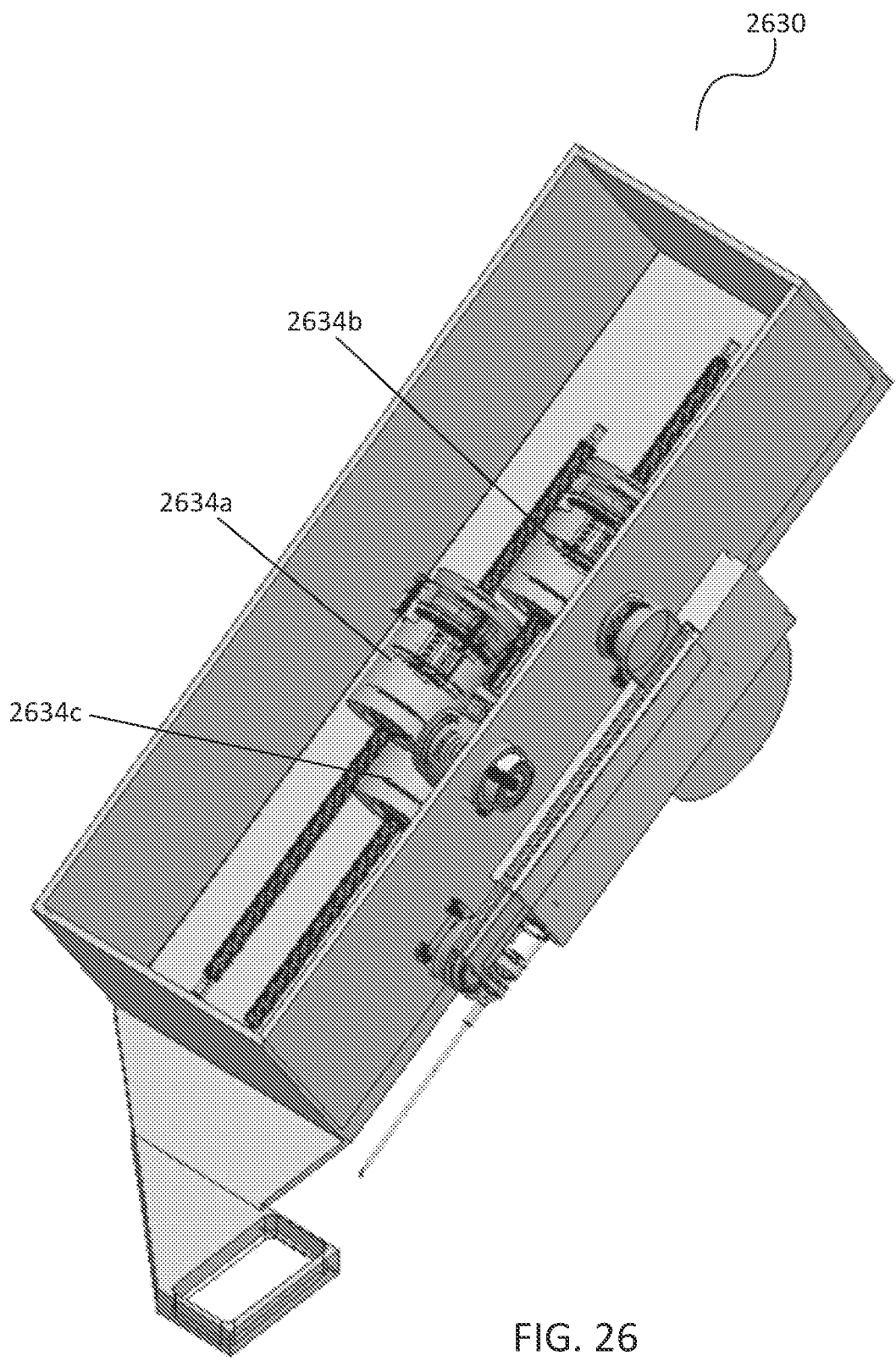
FIG. 26 illustrates another variation of a manipulation device, in accordance with some embodiments.
Figure 27A:
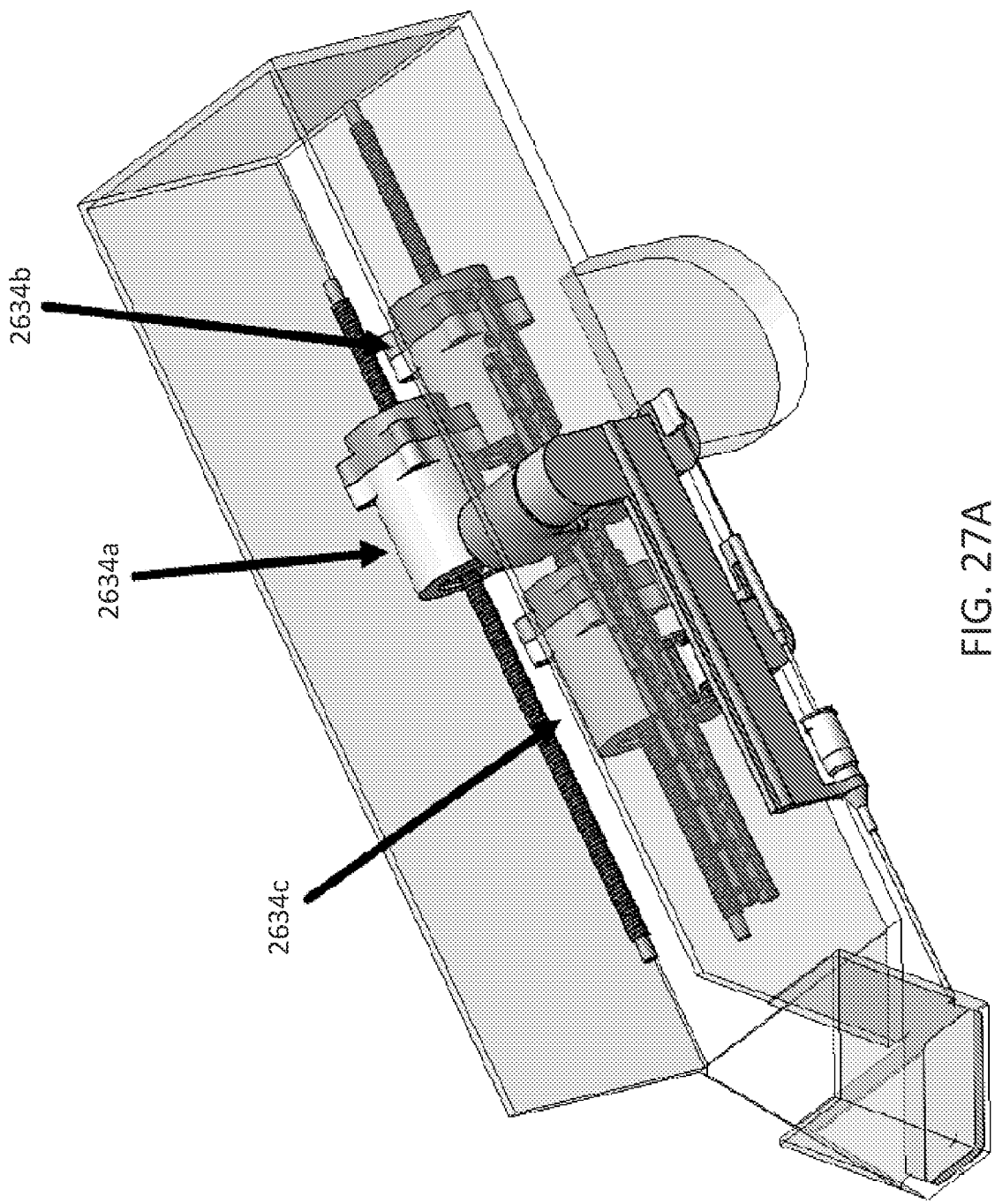
FIGS. 27A and 27B illustrate different views of the manipulation device shown in FIG. 26, in accordance with some embodiments.
Figure 27B:
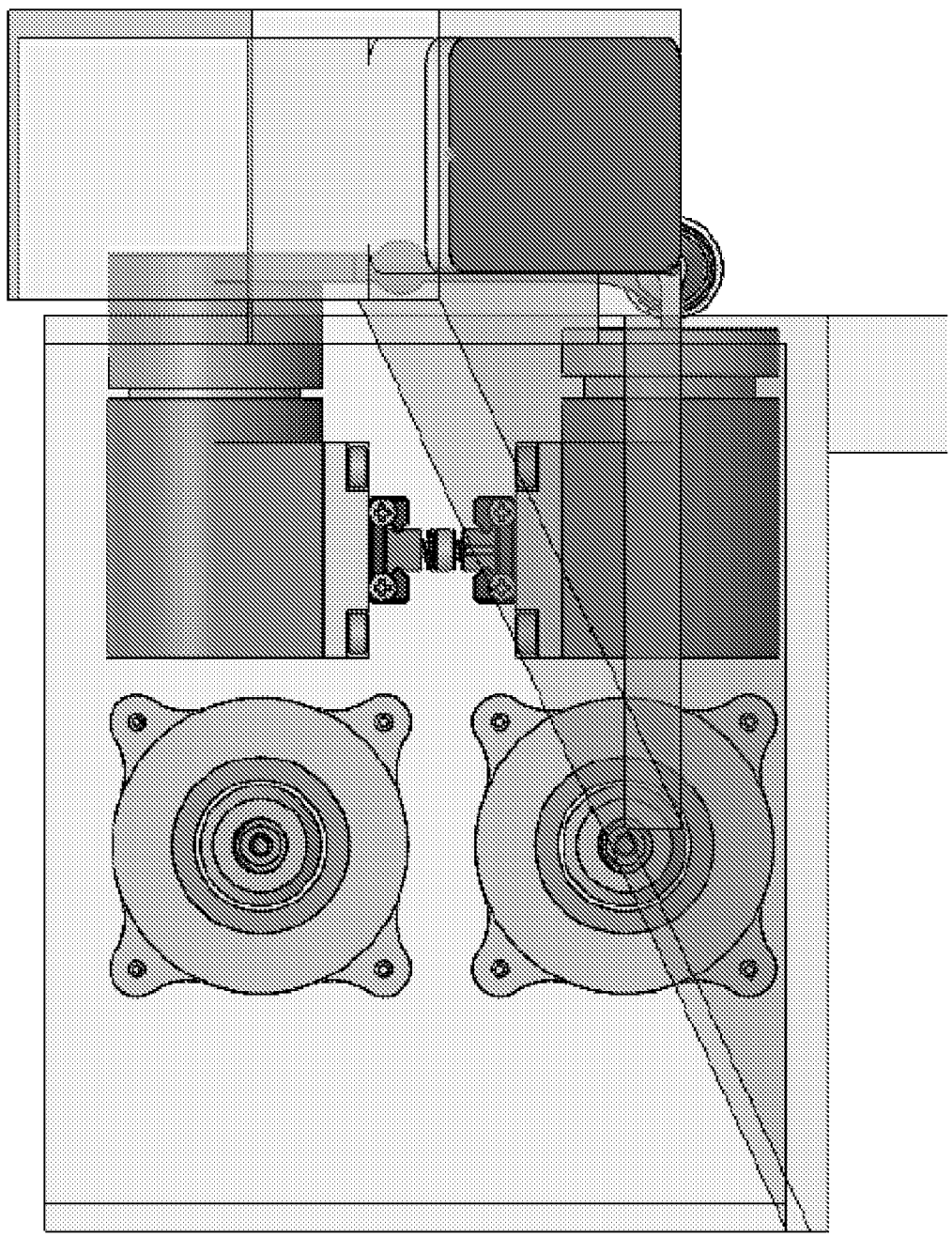

FIG. 26 illustrates another variation of a manipulation device 2630 (e.g., structurally and/or functionally similar to manipulation device 230 in FIG. 2 and/or manipulation device 530 in FIG. 5), in accordance with some embodiments. As seen in FIG. 26, the linear actuators (e.g., motors) for the guidewire and the needle, that is, motor 2634b and motor 2634c respectively, can be combined to be on a same ball screw shaft. The motor 2634a for the catheter is on a different ball screw shaft. Such an embodiment results in a more compact size, and allows the cartridge assembly to mount to a vertical face as opposed to the bottom face of the manipulation device 2630. Mounting the cartridge assembly to the vertical face gives the user better access to the cartridge assembly. FIGS. 27A and 27B illustrate different views of the manipulation device 2630 in FIG. 26, in accordance with some embodiments.

Figure 28:
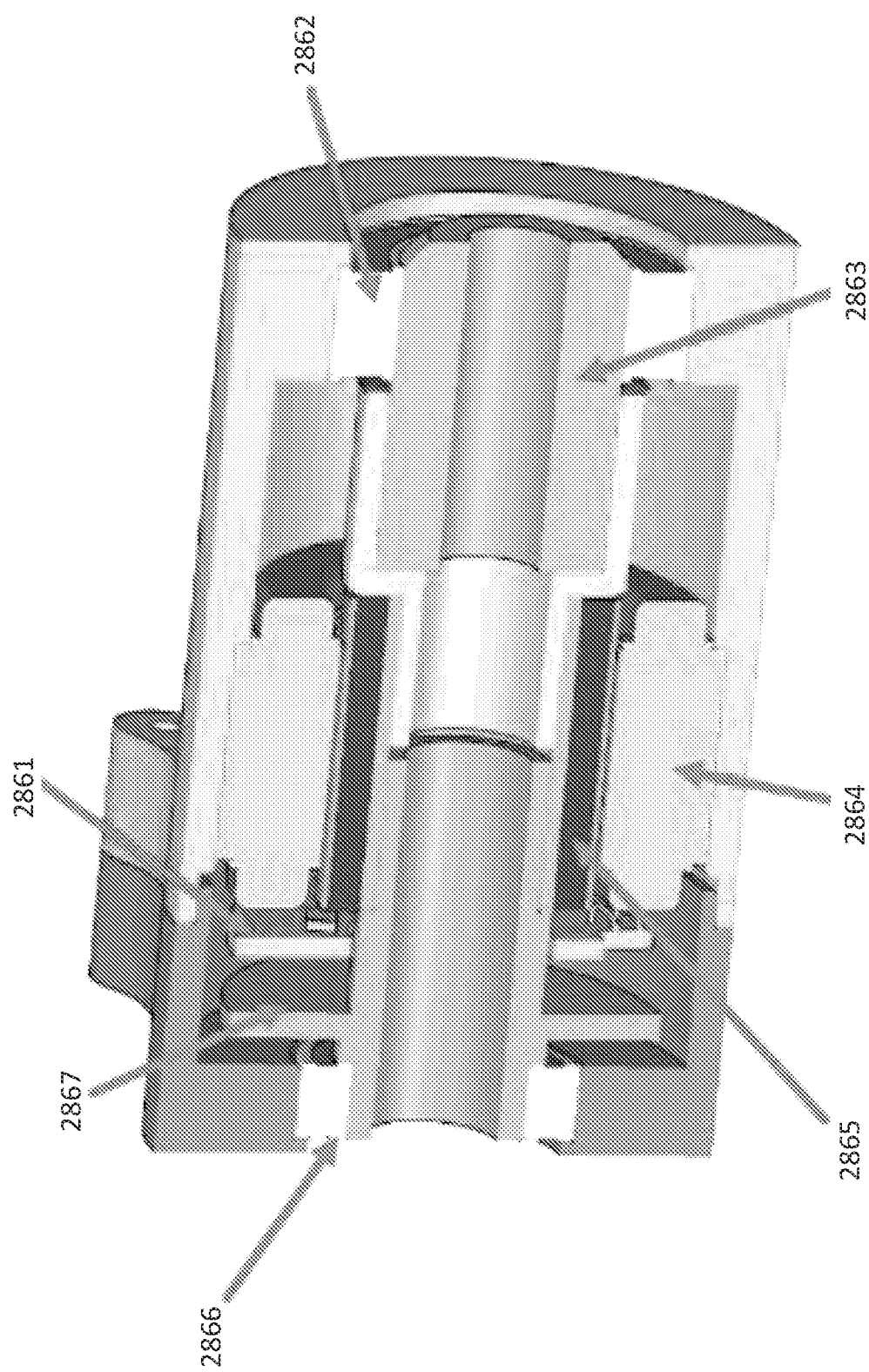
FIG. 28 is an illustration of a linear actuator within the manipulation device in FIG. 26 that can actuate the needle, the catheter, and/or the guidewire, in accordance with some embodiments.

FIG. 28 is an illustration of a linear actuator within the manipulation device 2630 in FIG. 26 (e.g., structurally and/or functionally similar to manipulation device 230 in FIG. 2 and/or manipulation device 530 in FIG. 5), that can actuate the needle, the catheter, and/or the guidewire, in accordance with some embodiments. The linear actuator includes a control unit 2861. The control unit 2861 can include motor protection algorithm, 3X Hall effect sensors, encoder chip, and optionally a thermistor. The actuator includes two radial bearings 2866 and 2862. The encoder disk 2867 is positioned to align with the 3X Hall effect sensors in the control unit 2861. The linear actuator also includes ball screw nut 2863, motor stator 2864, and motor rotor 2865. In contrast to the linear actuator(s) described above, the ball screw shaft is not fixed to the housing of the manipulation device and does not rotate. Instead, the ball screw nut 2863 mounted on the motor rotor 2865 rotates along with the motor rotor.

Figure 29A:
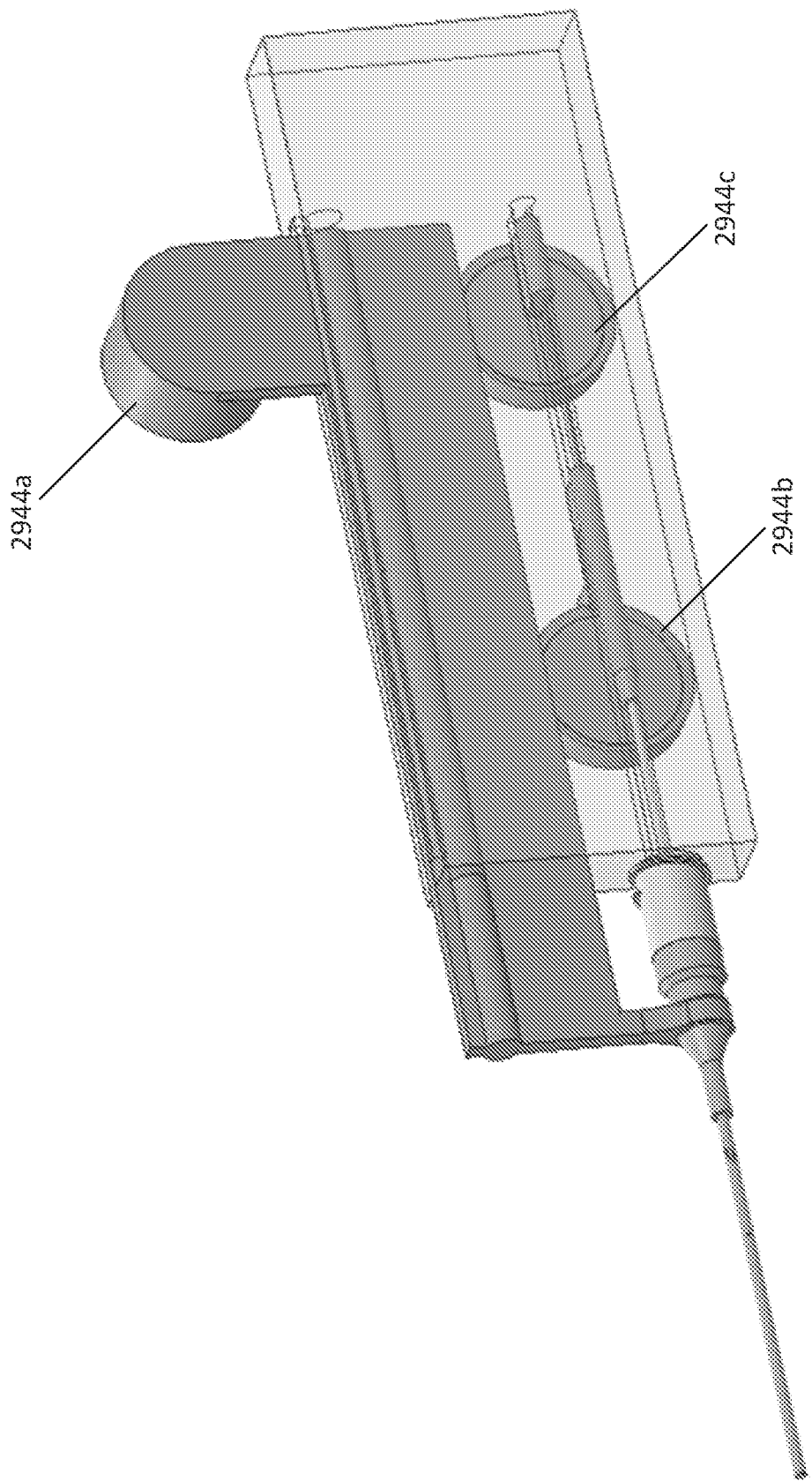
FIGS. 29A and 29B are an illustration of a cartridge assembly that attaches to the manipulation device in FIG. 26, in accordance with some embodiments.
Figure 29B:
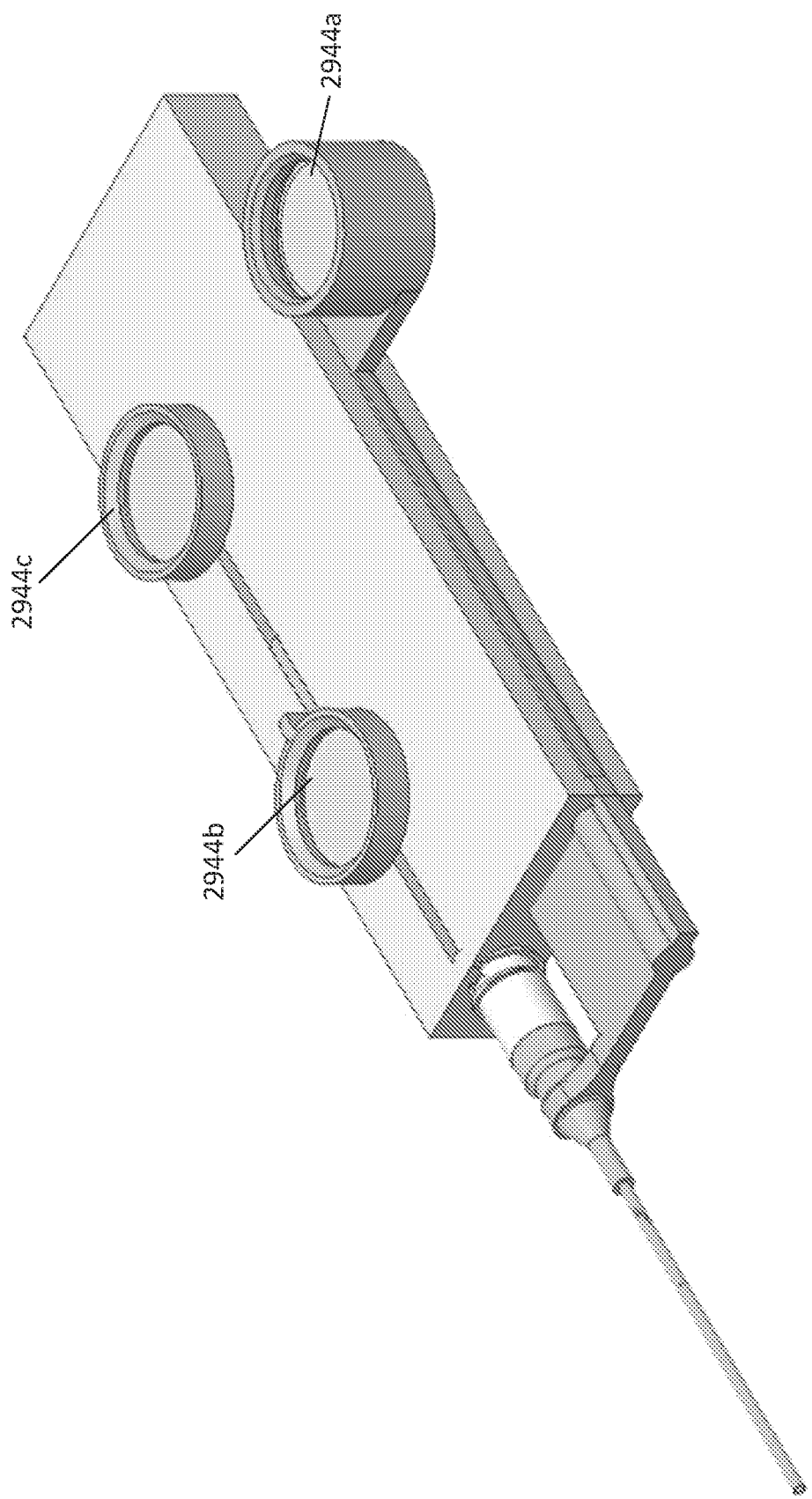

FIGS. 29A and 29B are an illustration of a cartridge assembly that attaches to the manipulation device in FIG. 26, in accordance with some embodiments. FIGS. 29A and 29B show the needle guide 2944b and the guidewire guide 2944c that guide the needle and guidewire respectively on a single linear axis. The catheter guide 2944a is on a separate linear axis. The cartridge assembly in FIGS. 29A and 29B are of a more compact size than that depicted in FIGS. 19A-19B.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Some embodiments and/or methods described herein can be performed by a different software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

The invention claimed is:

1. An apparatus, comprising:
   a cartridge including:
      a guidewire, a needle, and a catheter that are coaxially disposed with respect to each other; and
      a plurality of guides coupled to the guidewire, the needle, and the catheter;
   a manipulation device including:
      a plurality of actuators each configured to couple to a different guide member of the plurality of guides, the plurality of actuators including:
         a first linear actuator configured to linearly advance and retract a first guide of the plurality of guides to move the guidewire;
         a second linear actuator configured to linearly advance and retract a second guide of the plurality of guide to move the guide needle; and a third linear actuator configured to linearly advance and retract a third guide of the plurality of guides to move the catheter; and a plurality of shafts supporting the first linear actuator, the second linear actuator, and the third linear actuator; and a control unit operatively coupled to the manipulation device, the control unit configured to control the plurality of actuators to selectively move the needle, the guidewire, and the catheter to gain access via the catheter to a target vessel of a patient.

2. The apparatus of claim 1, wherein the plurality of shafts include:
a first shaft supporting the first linear actuator and the second linear actuator; and
a second shaft supporting the third linear actuator.

3. The apparatus of claim 1, wherein the plurality of shafts include:
a first shaft supporting the first linear actuator;
a second shaft supporting the second linear actuator; and
a third shaft supporting the third linear actuator.

4. An apparatus, comprising:
a cartridge including:
a guidewire, a needle, and a catheter that are coaxially disposed with respect to each other; and
a plurality of guides coupled to the guidewire, the needle, and the catheter;
a manipulation device including:
a plurality of actuators each configured to couple to a different guide member of the plurality of guides, the plurality of actuators being configured to linearly advance and retract the plurality of guides to move the needle, the guidewire, and the catheter; and
a plurality of recessed portions, each recessed portion of the plurality of recessed portions being configured to receive a respective guide member of the plurality of guides;
and
a control unit operatively coupled to the manipulation device, the control unit configured to control the plurality of actuators to selectively move the needle, the guidewire, and the catheter to gain access via the catheter to a target vessel of a patient.

5. An apparatus, comprising:
a cartridge including:
a guidewire, a needle, and a catheter that are coaxially disposed with respect to each other; and
a plurality of guides coupled to the guidewire, the needle, and the catheter;
a manipulation device including a plurality of actuators each configured to couple to a different guide member of the plurality of guides, the plurality of actuators being configured to linearly advance and retract the plurality of guides to move the needle, the guidewire, and the catheter, each actuator of the plurality of actuators includes a magnet configured to magnetically couple that actuator with a respective one of the plurality of guides; and
a control unit operatively coupled to the manipulation device, the control unit configured to control the plurality of actuators to selectively move the needle, the guidewire, and the catheter to gain access via the catheter to a target vessel of a patient.

6. The apparatus of claim 5, wherein each guide of the plurality of guides include a magnetic portion configured to magnetically couple to the magnet of the respective actuator coupled to that guide.

7. The apparatus of claim 6, wherein each actuator of the plurality of actuators includes a sensor configured to detect a coupling between the magnet of that actuator with the respective coupling element.

8. The apparatus of claim 1, wherein the cartridge is configured to store the guidewire in a linear state.

9. An apparatus, comprising:
a cartridge configured to couple to a manipulation device of a robotic system for providing access to a target vessel of a patient, the cartridge including:
a housing;
a guidewire disposable at least partially within the housing and configured to couple to a first linear actuator of the manipulation device that is moveable along a first axis to advance the guidewire;
a first guide coupled the guidewire, the first guide configured to couple to the first linear actuator via a first coupling element, the first coupling element includes a first magnetic portion configured to engage with a magnet of the first linear actuator;
a needle disposable at least partially within the housing and configured to couple to a second linear actuator of the manipulation device that is moveable along a second axis to advance the needle;
a second guide coupled to the needle, the second guide configured to couple to the second linear actuator via a second coupling element, the second coupling element includes a second magnetic portion configured to engage with a magnet of the second linear actuator;
a catheter configured to couple to a third linear actuator of the manipulation device that is moveable along a third axis to advance the catheter; and
a third guide releasably coupled to the catheter, the third guide configured to couple to the third linear actuator via a third coupling element, the third coupling element includes a third magnetic portion configured to engage with a magnet of the third linear actuator,
the guidewire, the needle, and the catheter being arranged coaxially with the guidewire being disposed within a lumen of the needle and the needle being disposed within a lumen of the catheter.

10. An apparatus, comprising:
a cartridge configured to couple to a manipulation device of a robotic system for providing access to a target vessel of a patient, the cartridge including:
a housing including features configured to fit in slots in the manipulation device to mechanically couple the housing to the manipulation device;
a guidewire disposable at least partially within the housing and configured to couple to a first linear actuator of the manipulation device that is moveable along a first axis to advance the guidewire and to a first guide configured to couple to the first linear actuator;
a needle disposable at least partially within the housing and configured to couple to a second linear actuator of the manipulation device that is moveable along a second axis to advance the needle and to a second guide configured to couple to the second linear actuator;
and
a catheter configured to couple to a third linear actuator of the manipulation device that is moveable along a third axis to advance the catheter and to releasably coupled to a third guide configured to couple to the third linear actuator, the guidewire, the needle, and the catheter being arranged coaxially with the guidewire being disposed within a lumen of the needle and the needle being disposed within a lumen of the catheter.

11. The apparatus of claim 9, wherein the cartridge is configured to store the guidewire in a linear state.

12. The apparatus of claim 9, further comprising a plurality of shafts supporting the first linear actuator, the second linear actuator, and the third linear actuator.

13. The apparatus of claim 1, wherein the cartridge is configured to store the guidewire in a linear state.

14. The apparatus of claim 1, wherein:
the first guide includes a first coupling element configured to couple the first guide to the first linear actuator,
the second guide includes a second coupling element configured to couple the third guide to the third linear actuator, and
the third guide includes a third coupling element configured to couple the third guide to the third linear actuator.

15. The apparatus of claim 1, wherein the cartridge includes features configured to fit in slots in the manipulation device to mechanically couple the cartridge to the manipulation device.

\* \* \* \* \*

UNITED STATES PATENT AND TRADEMARK OFFICE
CERTIFICATE OF CORRECTION

| | | |
|---|---|---|
| PATENT NO. | : 11,678,944 B1 | Page 1 of 1 |
| APPLICATION NO. | : 17/893534 | |
| DATED | : June 20, 2023 | |
| INVENTOR(S) | : Jonathan Azevedo et al. | |

It is certified that error appears in the above-identified patent and that said Letters Patent is hereby corrected as shown below:

On the Title Page

Please insert after item (22):
--Related U.S. Application Data
Division of application No. 17/700,391, filed on Mar. 21, 2022.
Provisional application No. 63/236,537, filed on Aug. 24, 2021.--

Signed and Sealed this
Twenty-fifth Day of July, 2023

Katherine Kelly Vidal
*Director of the United States Patent and Trademark Office*